US009738725B2

(12) United States Patent
Hallahan et al.

(10) Patent No.: US 9,738,725 B2

(45) Date of Patent: Aug. 22, 2017

(54) ANTIBODIES TO TIP-1

(71) Applicant: The Washington University, St. Louis, MO (US)

(72) Inventors: Dennis E. Hallahan, St. Louis, MO (US); Heping Yan, St. Louis, MO (US)

(73) Assignees: WASHINGTON UNIVERSITY, St. Louis, MO (US); VANDERBILT UNIVERSITY, Nashville, TN (US)

(*) Notice: Subject to any disclaimer, the term of this patent is extended or adjusted under 35 U.S.C. 154(b) by 560 days.

(21) Appl. No.: 14/166,251

(22) Filed: Jan. 28, 2014

(65) Prior Publication Data

US 2014/0316186 A1 Oct. 23, 2014

Related U.S. Application Data

(63) Continuation-in-part of application No. PCT/US2012/048856, filed on Jul. 30, 2012.

(60) Provisional application No. 61/513,333, filed on Jul. 29, 2011.

(51) Int. Cl.

| | |
|---|---|
| ***A61K 38/00*** | (2006.01) |
| ***A61K 39/00*** | (2006.01) |
| ***A61K 39/395*** | (2006.01) |
| ***A61K 49/00*** | (2006.01) |
| ***A61K 51/10*** | (2006.01) |
| ***C07K 16/18*** | (2006.01) |
| ***C07K 16/30*** | (2006.01) |
| ***A61N 5/10*** | (2006.01) |
| ***A61B 90/00*** | (2016.01) |

(52) U.S. Cl.

CPC ............ *C07K 16/30* (2013.01); *A61B 90/361* (2016.02); *A61K 39/3955* (2013.01); *A61K 49/0058* (2013.01); *A61K 51/1045* (2013.01); *A61K 51/1066* (2013.01); *A61K 51/1093* (2013.01); *A61N 5/10* (2013.01); *C07K 16/18* (2013.01); *C07K 16/3053* (2013.01); *A61N 2005/1098* (2013.01); *C07K 2317/34* (2013.01); *C07K 2317/622* (2013.01); *C07K 2317/73* (2013.01); *C07K 2317/94* (2013.01)

(58) Field of Classification Search

CPC .. A61K 38/00; A61K 39/395; A61K 49/0058; A61K 51/1045; A61K 2039/505; C07K 16/18; C07K 16/30; C07K 16/3053

See application file for complete search history.

(56) References Cited

U.S. PATENT DOCUMENTS

| | | | |
|---|---|---|---|
| 4,281,061 | A | 7/1981 | Zuk |
| 4,515,165 | A | 5/1985 | Carroll |
| 4,670,386 | A | 6/1987 | Sugaar |
| 5,223,409 | A | 6/1993 | Ladner et al. |
| 5,264,563 | A | 11/1993 | Huse |
| 5,277,892 | A | 1/1994 | Rhodes |
| 5,328,840 | A | 7/1994 | Coller |
| 5,334,369 | A | 8/1994 | Halushka et al. |
| 5,382,680 | A | 1/1995 | Abraham et al. |
| 5,516,881 | A | 5/1996 | Lee et al. |
| 5,614,535 | A | 3/1997 | Juraszyk |
| 5,645,815 | A | 7/1997 | Dean |
| 5,759,542 | A | 6/1998 | Gurewich |
| 5,776,427 | A | 7/1998 | Thorpe |
| 5,830,856 | A | 11/1998 | Dean |
| 5,855,866 | A | 1/1999 | Thorpe |
| 5,863,538 | A | 1/1999 | Thorpe |
| 5,889,169 | A | 3/1999 | Beach |
| 5,922,545 | A | 7/1999 | Mattheakis et al. |
| 5,962,424 | A | 10/1999 | Hallahan et al. |
| 5,965,132 | A | 10/1999 | Thorpe |
| 5,977,313 | A | 11/1999 | Heath |
| 6,004,554 | A | 12/1999 | Thorpe |
| 6,033,847 | A | 3/2000 | Sherr |
| 6,051,230 | A | 4/2000 | Thorpe |
| 6,068,829 | A | 5/2000 | Ruoslahti |
| 6,107,059 | A | 8/2000 | Hart |
| 6,156,511 | A | 12/2000 | Schatz |
| 6,156,736 | A | 12/2000 | Weichselbaum |
| 6,159,443 | A | 12/2000 | Hallahan |
| 6,174,687 | B1 | 1/2001 | Rajotte |
| 6,232,287 | B1 | 5/2001 | Ruoslahti et al. |
| 6,261,535 | B1 | 7/2001 | Thorpe |
| 6,277,974 | B1 | 8/2001 | Lo et al. |
| 6,316,208 | B1 | 11/2001 | Roberts |
| 6,383,470 | B1 | 5/2002 | Fritzsch |
| 6,403,383 | B1 | 6/2002 | Casterlin |
| 6,576,239 | B1 | 6/2003 | Ruoslahti |
| 6,605,712 | B1 | 8/2003 | Weichselbaum |
| 6,630,570 | B1 | 10/2003 | Licha et al. |

(Continued)

FOREIGN PATENT DOCUMENTS

| | | | |
|---|---|---|---|
| EP | 0723156 | A2 | 7/1996 |
| EP | 0723156 | A3 | 4/1998 |

(Continued)

OTHER PUBLICATIONS

Bendig, M.M. Humanization of roden monoclonal antibodies by CDR grafting. Methods: A companion to methods in enzymology, 1995, vol. 8, p. 83-93.*

Casset, F. et al. A peptide mimetic of an anti-CD4 monoclonal antibody by rationale design. Biochem. Biophys. Res. Comm., 2003, vol. 307, p. 198-205.*

MacCallum, R.M., et al. Antibody-antigen interactions: contact analysis and binding site topography. J. Mol. Biol., 1996, vol. 262, p. 732-745.*

Paul, Fundamental Immunology, 3rd Edition, 1993, pp. 292-295.*

Rudikoff, S., et al. Single amino acid substitution altering antigen-binding specificity. Proc. Natl. Acad. Sci. USA, 1982, vol. 79, p. 1979-1983.*

Vajdos, F.F., et al. Comprehensive functional maps of the antigen-binding site of an anti-ErbB2 antibody obtained with shotgun scanning mutagensis. J. Mol. Biol., 2002, vol. 320, p. 415-428.*

(Continued)

*Primary Examiner* — Robert Landsman

*Assistant Examiner* — Bruce D Hissong

(74) *Attorney, Agent, or Firm* — Polsinelli PC

(57) ABSTRACT

The present invention is directed towards isolated antibodies that bind to GRP78 and TIP-1.

8 Claims, 47 Drawing Sheets

(41 of 47 Drawing Sheet(s) Filed in Color)

(56) References Cited

U.S. PATENT DOCUMENTS

| | | | |
|---|---|---|---|
| 6,673,545 | B2 | 1/2004 | Faris et al. |
| 7,018,615 | B2 | 3/2006 | Ruoslahti |
| 7,018,618 | B2 | 3/2006 | Lewis et al. |
| 7,049,140 | B1 | 5/2006 | Hallahan |
| 7,056,506 | B2 | 6/2006 | Varner |
| 7,122,361 | B2 | 10/2006 | Liu et al. |
| 7,138,238 | B2 | 11/2006 | Vodyanoy |
| 7,230,083 | B2 | 6/2007 | Jonak et al. |
| 7,230,088 | B2 | 6/2007 | Rajagopalan et al. |
| 7,306,925 | B2 | 12/2007 | Hallahan |
| 7,402,392 | B2 | 7/2008 | Hallahan |
| 7,906,102 | B2 | 3/2011 | Hallahan |
| 7,968,675 | B2 | 6/2011 | Hallahan |
| 8,012,945 | B2 | 9/2011 | Hallahan et al. |
| 8,101,157 | B2 | 1/2012 | Hallahan |
| 8,388,932 | B2 | 3/2013 | Hallahan et al. |
| 8,617,521 | B2 | 12/2013 | Hallahan et al. |
| 8,765,097 | B2 | 7/2014 | Hallahan et al. |
| 2002/0086288 | A1 | 7/2002 | Bird et al. |
| 2002/0164663 | A1 | 11/2002 | Fuqua et al. |
| 2003/0027159 | A1 | 2/2003 | Ward et al. |
| 2003/0083261 | A1 | 5/2003 | Yu et al. |
| 2003/0157025 | A1 | 8/2003 | Unger et al. |
| 2003/0157482 | A1 | 8/2003 | Keesee |
| 2004/0191249 | A1 | 9/2004 | Hallahan et al. |
| 2006/0046271 | A1 | 3/2006 | Hallahan |
| 2006/0104898 | A1 | 5/2006 | Hallahan |
| 2007/0065361 | A1 | 3/2007 | Hallahan |
| 2007/0081993 | A1 | 4/2007 | Kufer et al. |
| 2008/0118978 | A1 | 5/2008 | Sato et al. |
| 2008/0187488 | A1 | 8/2008 | Hallahan et al. |
| 2008/0206130 | A1 | 8/2008 | Hallahan et al. |
| 2008/0305111 | A1 | 12/2008 | Evans et al. |
| 2010/0039023 | A1 | 2/2010 | Rogojevic et al. |
| 2010/0041074 | A1 | 2/2010 | Kimura |
| 2010/0111852 | A1 | 5/2010 | Yoshida |
| 2010/0111959 | A1 | 5/2010 | Swanson et al. |
| 2010/0135905 | A1 | 6/2010 | Hallahan et al. |
| 2011/0213293 | A1 | 9/2011 | Hallahan et al. |
| 2012/0041303 | A1 | 2/2012 | Hallahan et al. |
| 2012/0089017 | A1 | 4/2012 | Hallahan et al. |
| 2013/0251628 | A1 | 9/2013 | Hallahan et al. |

FOREIGN PATENT DOCUMENTS

| | | | |
|---|---|---|---|
| EP | 1217377 | B1 | 6/2002 |
| WO | 9220796 | A2 | 11/1992 |
| WO | 9314791 | A2 | 8/1993 |
| WO | 9534315 | A1 | 12/1995 |
| WO | 9810795 | A3 | 3/1998 |
| WO | 9904238 | A2 | 1/1999 |
| WO | 0066182 | A1 | 11/2000 |
| WO | 0109611 | A2 | 2/2001 |
| WO | 0109611 | A3 | 7/2001 |
| WO | 2005042780 | A1 | 5/2005 |
| WO | 2006028993 | A2 | 3/2006 |
| WO | 2007011680 | A2 | 1/2007 |
| WO | 2013019730 | A1 | 2/2013 |
| WO | 2013049830 | A2 | 4/2013 |

OTHER PUBLICATIONS

Wu, H., et al. Humanization of a murine monoclonal antibody by simultaneous optimization of framework and CDR residues. J. Mol. Biol., 1999, vol. 294, p. 151-162.*

International Preliminary Report on Patentability from related WIPO Patent Application No. PCT/US2006/027283, dated Jan. 16, 2008, 4 pages.

International Preliminary Report on Patentability from related WIPO Patent Application No. PCT/US2012/058329, dated Apr. 10, 2014, 5 pages.

International Search Report from related WIPO Patent Application No. PCT/US2006/027283, dated Mar. 13, 2007, 2 pages.

International Search Report from related WIPO Patent Application No. PCT/US2005/031367 dated Oct. 11, 2007, 1 page.

International Search Report from WIPO Patent Application No. PCT/US04/034719 dated Jan. 26, 2005, 1 page.

International Search Report from WIPO Patent Application No. PCT/US2012/048856, dated Jan. 4, 2013, 6 pages.

International Search Report from WIPO Patent Application No. PCT/US2012/058329, dated Jan. 8, 2013, 2 pages.

Interview Summary from related U.S. Appl. No. 12/111,693, dated Dec. 22, 2010, 2 pages.

Ito, T. et al., "Preclinical Assessments of 90Y-labeled C110 Anti-Carcinoembryonic Antigen Immunotoxin: A Therapeutic Immunoconjugate for Human Colon Cancer," Cancer Res., Jan. 1, 1991, pp. 255-260, vol. 51.

Jahroudi, N. et al., "Ionizing irradiation increases transcription of the von Willebrand factor gene in endothelial cells," Blood, Nov. 15, 19966, pp. 3801-3814, vol. 88, No. 10.

Jain, R., "Barriers to Drug Delivery in Solid Tumors," Scientific American, Jul. 1994, pp. 58-65, vol. 271.

Johnson, T. et al., "Therapy of B-cell lymphomas with monoclonal antibodies and radioimmunoconjugates: the Seattle experience," Ann. Hematol., 2000 pp. 175-182, vol. 79.

Kastan, M. et al., "ATM kinase modulation for screening and therapies," Database HCAPLUS on STN, 2000, Abstract WO00/47760, Accession No. 2000:573954, Registry No. 288259-02-9 for SEQ ID No. 8 and SEQ ID No. 10 and Registry No. 288259-18-7 for SEQ ID No. 13, 1 page.

Kelley, M. et al., "CDKN2 in HPV-Positive and HPV-Negative Cervical-Carcinoma Cell Lines," Int. J. Cancer, 1995 pp. 226-230, vol. 63.

Khleif, S. et al., "Inhibition of cyclin D-CDK4/CDK6 activity is associated with an E2F-mediated induction of cyclin kinase inhibitor activity," PNAS, Apr. 1996, pp. 4350-4354, vol. 93.

Kim, J. et al., "Absence of p15INK4B and p16INK4A Gene Alterations in Primary Cervical Carcinoma Tissues and Cell Lines with Human Papillomavirus Infection," Gynecologic Oncology, 1998, pp. 75-79, vol. 70, Article No. GO985041.

Kim, Y. et al., "Underexpression of Cyclin-Dependent Kinase (CDK) Inhibitors in Cervical Carcinoma," Gynecologic Oncology, 1998, pp. 38-45, vol. 71, Article No. GO985134.

Klaes, R. et al., "Overexpression of p16INK4A as a Specific Marker for Dysplastic and Neoplastic Epthelial Cells of the Cervis Uteri," Int. J. Cancer, 2001, pp. 276-284, vol. 92.

Koivunen, E. et al., "Isolation of a Highly Specific Ligand for the alpha5beta1 Integrin from a Phage Display Library," J. Cell Biol., 1994, pp. 373-380, vol. 124.

Koivunen, E. et al., "Selection of Peptides Binding to the alpha5beta1 Integrin from Phage Display Library," J. Bio. Chem., Sep. 25, 1993, pp. 20205-20210, vol. 268, No. 27.

Krauer, K. et al., "Antitumor Effect of 2'-Deoxy-5-fluorouridine Conjugates against a Murine Thymoma and Colon Carcinoma Xenografts," Cancer Res., Jan. 1, 1992, pp. 132-137, vol. 52.

Kurnik, B. et al., "Prospective study of atrial natriuretic peptide for the prevention of radio-contrast-induced nephropathy," Database HCAPLUS on STN, Abstract, Am. J. Kidney Disease, 1998, Accession No. 1998:248017, Registry No. 95896-08-5 for atrial natriuetic peptide-25, for SEQ ID No. 11, 1 page.

Lieberman, H. et al., "A human homolog of the Schizosaccharomyces pombe rad9+ checkpoint control gene," PNAS, Nov. 1996, pp. 13890-13895, vol. 93.

Liggett, W. et al., "Role of the p16 Tumor Suppressor Gene in Cancer," J. Clin. Onocl., Mar. 1998, pp. 1197-1206, vol. 16, No. 3.

Llovet, J. et al., "Arterial embolisation or chemoembolisation versus symptomatic treatment in patients with unresectable hepatocellular carcinoma: a randomised controlled trial," Lancet, May 18, 2002, pp. 1734-1739, vol. 359.

Mao, C. et al., "Evaluation of a new p16INK4a ELISA test and a high-risk HPV DNA test for cervical cancer screening: Results from proof-of-concept study," Int. J. Cancer, 2007, pp. 2435-2438, vol. 120.

Martin, F., et al., "Targeted Retroviral Infection of Tumor Cells by Receptor Cooperation," J. Virology, Feb. 2003, pp. 2753-2756, vol. 77, No. 4.

(56) References Cited

OTHER PUBLICATIONS

Mauceri, H. et al., "Tumor Necrosis Factor alpha (TNF-alpha) Gene Therapy Targeted by Ionizing Radiation Selectively Damages Tumor Vasculature," Cancer Res., Oct. 1, 1996, pp. 4311-4314, vol. 56.
McCabe, J., "The effects of detergents on the enzyme-linked immunosorbent assay (ELISA) of blood group substances," J. Immunol., Methods, Apr. 1988, pp. 129-135, vol. 108, No. 1 [Abstract Only].
Milde-Langosch, K. et al., "P16/MTS1 and pRB expression in endometrial carcinomas," Virchows Arch, 1999, pp. 23-28, vol. 434.
Milde-Langosch, K. et al., "p16/MTS1 Inactivation in Ovarian Carcinomas: High Frequency of Reduced Protein Expression Associated With Hyper-Methylation or Mutation in Endometrioid and Mucinous Tumors," Int. J. Cancer (Pred. Oncol.), 1998, pp. 61-65, vol. 79.
Molema, G. et al., "Tumor Vascular Endothelium: Barrier or Target in Tumor Directed Drug Delivery and Immunotherapy," Pharm. Res., 1997, pp. 2-10, vol. 14, No. 1.
Munro, S. et al., "An Hsp70-like Protein in the ER: Identity with the 78 kd Glucose-Regulated Protein and Immunoglobulin Heavy Chain Binding Protein," Cell, Jul. 18, 1986, pp. 291-300, vol. 46, Cell Press.
Myung, N. et al., "Loss of p16 and p27 is associated with progression of Human gastric cancer," Cancer Letters, 2000, pp. 129-136, vol. 153.
Nakao, Y. et al., "Induction of p16 during immortalization by HPV 16 and 18 and not during malignant transformation," British J. Cancer, 1997, pp. 1410-1416, vol. 75, No. 10.
Notice of Allowance from related U.S. Appl. No. 10/689,006, dated Jul. 24, 2007, 6 pages.
Notice of Allowance from related U.S. Appl. No. 11/592,451, dated Sep. 12, 2011, 5 pages.
Notice of Allowance from related U.S. Appl. No. 11/953,780, dated Apr. 29, 2011, 5 pages.
Notice of Allowance from related U.S. Appl. No. 13/766,310, dated Feb. 19, 2014, 7 pages.
Notice of Allowance, with Examiner-Initiated Interview Summary, from related U.S. Appl. No. 13/018,747, dated Nov. 6, 2012, 8 pages.
Notice of Allowance, with Examiner-Initiated Interview Summary, from related U.S. Appl. No. 11/183,325, dated Oct. 28, 2010, 9 pages.
Notice of Allowance, with Interview Summary, from related U.S. Appl. No. 12/111,693, dated Feb. 22, 2011, 10 pages.
Nuovo, G. et al., "In situ detection of the hypermethylation-induced inactivation of the p16 gene as an early event in oncogenesis," PNAS, Oct. 26, 1999, pp. 12754-12759, vol. 96, No. 22.
O'Brien, P. et al., "Antibody Phage Display: Methods and Protocols," E-Streams, Dec. 2002, pp. 1-2, vol. 5, No. 12.
Office Action (Advisory) from related U.S. Appl. No. 11/592,451, dated Feb. 28, 2011, 3 pages.
Office Action from related U.S. Appl. No. 10/689,006, dated Jan. 19, 2007, 6 pages.
Office Action from related U.S. Appl. No. 11/183,325, dated Jun. 8, 2010, 11 pages.
Office Action from related U.S. Appl. No. 11/592,451 dated Mar. 24, 2011, 18 pages.
Office Action from related U.S. Appl. No. 11/592,451, dated May 13, 2010, 11 pages.
Office Action from related U.S. Appl. No. 11/592,451, dated Nov. 18, 2010, 17 pages.
Arap, W. et al., "Cancer Treatment by Targeted Drug Delivery to Tumor Vasculature in a Mouse Model," Science, Jan. 16, 1998, pp. 377-380, vol. 279.
Baillie, C.T. et al., "Tumor vasculature—a potential therapeutic agent," British J. Can., 1995, pp. 257-267, vol. 72.
Barry, M. et al., "Toward cell-targeting gene therapy vectors: Selection of cell-binding peptides from random peptide-presenting phage libraries," Nature Medicine, Mar. 3, 1996, pp. 299-305, vol. 2, No. 3.
Bender, H. et al., "External Beam Radiation Enhances Antibody Mediated Radiocytotoxicity in Human Glioma Cells in Vitro," Anticancer Res., 1997, pp. 1797-1802, vol. 17.
Bhakdi, S., "Removal of SDS From Proteins for Immunochemical Analyses: A Simple Method Utilizing Ultracentrifugation in Sucrose Density Gradients Containing Non-Ionic Detergent," J. Biochem. Biophys. Methods, 1980, pp. 79-90, vol. 2.
Bird, R. et al., "Single-Chain Antigen-Binding Proteins," Science, New Series, Oct. 21, 1988, pp. 423-426, vol. 242, No. 4877.
Boothman, D. et al., "Induction of Tissue-type Plasminogen Activator by Ionizing Radiation in Human Malignant Melanoma Cells," Cancer Res., 1991, pp. 5587-5595, vol. 51.
Brach, M. et al, "Ionizing Radiation Induces Expression of Interleukin 6 by Human Fibroblasts Involving Activation of Nuclear Factor-kB," J. Biolog. Chem., Apr. 25, 1993, pp. 8466-8472, vol. 268, No. 12.
Burg, M. et al., "NG2 Proteoglycan-binding Peptides Target Tumor Neovasculature," Cancer Res., Jun. 15, 1999, pp. 2869-2874, vol. 59.
Cai, X. et al, "Anti-melanoma antibodies from melanoma patients immunized with genetically modified autologous tumor cells: Selection of specific antibodies from single-chain Fv fusion phage libraries," PNAS, Jul. 1995, pp. 6537-6541, vol. 92.
Castellano, M. et al., "CDKN2A/p16 Is Inactivated in Most Melanoma Cell Lines," Cancer Res, 1997, pp. 4868-4875, vol. 57.
Chen, C. et al., "Reactivity of Synthetic Peptide Analogs of Adhesive Proteins in Regard to the Interaction of Human Endothelial Cells With Extracellular Matrix," Blood, May 15, 1991, pp. 2200-2206, vol. 77, No. 10.
Cheresh, D. et al., "Human endothelial cells synthesize and express an Arg-Gly-Asp-directed adhesion receptor involved in attachment to fibrinogen and von Willebrand factor," PNAS, Sep. 1987, pp. 6471-6475, vol. 84.
Croce, C. et al., "Cloning of human RAD54 gene homolog and its diagnostic and therapeutic uses," Database HCAPLUS on STN, 1998, Abstract EP0844305, Accession No. 1998:365000, Registry No. 208601-90-5 for human rad54 for SEQ ID No. 12, 1 page.
Dai, C. et al., "p16INK4a Expression Begins Early in Human Colon Neoplasia and Correlates Inversely With Markers of Cell Proliferation," Gastroenterology, 2000, pp. 929-942, vol. 119.
De Bree, R. et al., "Selection of monoclonal antibody E48 IgG or U36 IgG for adjuvant radioimmunotherapy in head and neck cancer patients," British J. Cancer, 1997, pp. 1049-1060, vol. 75, No. 7.
Dimitriadis, G., "Effect of Detergents on Antibody-Antigen Interaction," Anal. Biochem., 1979, pp. 445-451, vol. 98.
Dolganov, G., "The human RAD50 and Septin-2 genes and their roles in myelodysplastic diseases and their diagnostic and therapeutic uses," Database HCAPLUS on STN, 1997, Abstract WO97/27284, Accession No. 1997:513697, Registry No. 194813-18-8 for human clone B15.2, for SEQ ID No. 8, 1 page.
Edmonds, S., "Antibody-Targeted Chemotherapy with Mylotarg Shows Promise for Many Adults with Deadly Form of Leukemia," American Society of Clinical Oncology 36th Annual Meeting, May 21, 2000, New Orleans, Louisana.
Ellerby, H. et al., "Anti-cancer activity of targeted pro-apoptotic peptides," Nature Medicine, Sep. 1999, pp. 1032-1038, vol. 5, No. 9.
Evan, G. et al., "Isolation of Monoclonal Antibodies Specific for Human c-myc Proto-Oncogene Product," Mol. Cell . Biol., Dec. 1985, pp. 3610-3616, vol. 5, No. 12.
Figini, M. et al., "Panning Phage Antibody Libraries on Cells: Isolation of Human Fab Fragments against Ovarian Carcinoma Using Guided Selection," Cancer Res., Mar. 1, 1998, pp. 991-996, vol. 58.
Fox, S. et al., "Markers of tumor angiogenesis: clinical applications in prognosis and anti-angiogenic therapy," Investigational New Drugs, 1997, pp. 15-28, vol. 15.

(56) References Cited

OTHER PUBLICATIONS

Geradts, J. et al., "Frequent Loss of KAI1 Expression in Squamous and Lymphoid Neoplasms," Am. J. Path., Jun. 1999, pp. 1665-1671, vol. 154, No. 6.
Geradts, J. et al., "Immunohistochemical Detection of the Cyclin-dependent Kinase Inhibitor 2/Multiple Tumor Suppressor Gene 1 (CDKN2/MTS1) Product p16INK4A in Archival Human Solid Tumors: Correlation with Retinoblastoma Protein Expression," Cancer Res., 1995, pp. 6006-6011, vol. 55.
Goldman, C. et al., "Targeted Gene Delivery to Kaposi's Sarcoma Cells via the Fibroblast Growth Factor Receptor," Cancer Res., Apr. 15, 1997, pp. 1447-1451, vol. 57.
Gump, J. et al., "Phosphorylation of p16INK4A Correlates with Cdk4 Association," J. Biol. Chem., Feb. 28, 2003, pp. 6619-6622, vol. 278, No. 9.
Hallahan, D. et al., "Ionizing Radiation Mediates Expression of Cell Adhesion Molecules in Distinct Histological Patterns within the Lung," Cancer Res., Jun. 1, 1997, pp. 2096-2099, vol. 57.
Hallahan, D. et al., "Cell Adhesion Molecules Mediate Radiation-induced Leukocyte Adhesion to the Vascular Endothelium," Cancer Res., Nov. 15, 1996, pp. 5150-5155, vol. 56.
Hallahan, D. et al., "c-jun and Egr-1 Participate in DNA Synthesis and Cell Survival in Response to Ionizing Radiation Exposure," J. Bio. Chem., Dec. 22, 1995, pp. 30303-30309, vol. 270, No. 51.
Hallahan, D. et al., "E-selectin gene induction by ionizing radiation is independent of cytokine induction," Biochem. Biophys. Res. Commun., Dec. 26, 1995, pp. 784-795, vol. 217, No. 3.
Hallahan, D. et al., "Integrin-mediated targeting of drug delivery to irradiated tumor blood vessels," Cancer Cell, Jan. 2003, pp. 63-74, vol. 3.
Hallahan, D. et al., "Intercellular adhesion molecule 1 knockout abrogates radiation induced pulmonary inflammation," PNAS, Jun. 1997, pp. 6432-6437, vol. 94.
Hallahan, D. et al., "Nuclear Factor kB Dominant Negative Genetic Constructs Inhibit X-ray Induction of Cell Adhesion Molecules in the Vascular Endothelium," Cancer Res., Dec. 1, 1998, pp. 5484-5488, vol. 58.
Hallahan, D. et al., "Radiation Signaling Mediated by Jun Activation following Dissociation from a Cell Type-specific Repressor," J. Bio. Chem., Mar. 5, 1993, pp. 4903-4907, vol. 268, No. 7.
Hallahan, D. et al., "Spatial and temporal control of gene therapy using ionizing radiation," Nature Medicine, Aug. 1995, pp. 786-791, vol. 1, No. 8.
Hallahan, D. et al., Targeting drug delivery to radiation-induced neoantigens in tumor microvasculature, J. Controlled Release, 2001, pp. 183-191, vol. 74.
Hallahan, D., "Radiation-Mediated Gene Expression in the Pathogenesis of the Clinical Radiation Response," Seminars Radiat. Oncol., Oct. 1996, pp. 250-267, vol. 6, No. 4.
Hallahan, D., et al., "Radiation-Mediated Control of Drug Delivery," Am. J. Clin. Oncol., 2001, pp. 473-480, vol. 24, No. 5.
Harari, O. et al., "Targeting an adenoviral gene vector to cytokine-activated vascular endothelium via E-selectin," Gene Therapy, 1999, pp. 801-807, vol. 6, Stockton Press.
Hariri, G. et al., "Radiation-Guided Drug Delivery to Mouse Models of Lung Cancer," Clin. Cancer Res., Oct. 15, 2010, pp. 4968-4977, vol. 16, No. 20.
He, X-S. et al., "Expression, deleton and mutation of p16 gene in human gastric cancer," World J. Gastroenterol., 2001, pp. 515-521, vol. 7, No. 4.
Hirama, T. et al., "p16 (CDKN2-Cyclin-dependent Kinase-4 Inhibitor-Multiple Tumor Suppressor-1) Gene is Not Altered in Uterine Cervical Carcinomas or Cell Lines," Modern Pathology, 1996, pp. 26-30, vol. 9, No. 1 [Abstract Only].
Hirata, "Fate of Intravenously Injected Human Tumor Cells in the Lung of Nude Mice Following Whole-Body X-Irradiation," Invasion Metastasis, 1985, pp. 61-70, [Abstract Only].
Hirata, H. et al., "Artificial Metastases and Decrease of Fibrinolysis in the Nude Mouse Lung After Hemithoracic Irradiation," Clin. Expl. Metatasis, 1984, pp. 311-319, vol. 2, No. 4, [Abstract Only].
Humira™ (adalimumab) Package Insert, Dec. 20, 2002, 16 pages.
Huston, J., "Protein engineering of antibody binding sites: Recovery of specific activity in an anti-digoxin single-chain Fv analogue produced in *Escherichia coli*," PNAS, Aug. 1998, pp. 5879-5883, vol. 85.
Ikeda, K. et al., "Extraction and Analysis of Diagnostically Useful Proteins from Formalin-fixed, Paraffin-embedded Tissue Sections," J. Histochem. Cytochem., 1998, pp. 397-403, vol. 46, No. 3.
International Preliminary Examination Report from related WIPO Patent Application No. PCT/US04/034719, dated Oct. 14, 2005, 3 pages.
International Preliminary Report on Patentability from related WIPO Patent Application No. PCT/US2005/031367 dated Oct. 30, 2007, 4 pages.
Database GenBank: AAD40244.1, Jun. 22, 1999, "single chain antibody for Mab7, partial [synthetic construct]"; 1 pg.
Database GenBank: AEC23014.1, May 17, 2011, "immunoglobulin heavy chain V(D)J region, partial [Mus musculus]"; 2 pgs.
International Search Report and Written Opinion from related International Application No. PCT/US2015/013241, dated May 7, 2015; 10 pgs.
Weiss et al., "Rapid mapping of protein functional epitopes by combinatorial alanine scanning", PNAS, 2000, pp. 8950-8954, vol. 97, No. 16.
Office Action from related U.S. Appl. No. 11/953,780, dated Oct. 22, 2010, 6 pages.
Office Action from related U.S. Appl. No. 11/953,780, dated Feb. 19, 2010, 6 pages.
Office Action from related U.S. Appl. No. 12/111,693, dated Aug. 5, 2010, 27 pages.
Office Action from related U.S. Appl. No. 13/326,870, dated Jun. 25, 2014, 13 pages.
Office Action from related U.S. Appl. No. 13/766,310, dated Nov. 12, 2013, 8 pages.
O'Nions, J. et al., "p73 is over-expressed in vulval cancer principally as the Δ2 isoform," British J. Cancer, 2001, pp. 1551-1556, vol. 85, No. 10.
Pan, X-M. et al., "What is the Minimum Number of Residues to Determine the Secondary Structural State?," J. Protein Chem., 1999, pp. 579-584, vol. 18, No. 5.
Pasqualini, R. et al., "Organ targeting in vivo using phage display peptide libraries," Nature, Mar. 28, 1996, pp. 364-366, vol. 380.
Passarella, R. et al., "Targeted Nanoparticles That Deliver a Sustained, Specific Release of Paclitaxel to Irradiated Tumors," Cancer Res., Jun. 1, 2010, pp. 4550-4559, vol. 70, No. 11.
Pastan, I., "Targeted therapy of cancer with recombinant immunotoxins," Biochimica et Biophysica Acta, 1997, pp. C1-C6, vol. 1333.
Pinsky, D. et al., "Hypoxia-induced Exocytosis of Endothelial Cell Weibel-Palade Bodies. A Mechanism for Rapid Neutrophil Recruitment after Cardiac Preservation," J. Clin. Invest., Jan. 1996, pp. 493-500, vol. 97, No. 2.
Plath, T. et al., "A Novel Function for the Tumor Suppressor p16INK4a: Induction of Anoikis via Upregulation of the alpha5beta1 Fibronectin Receptor," J. Cell Bio., Sep. 18, 2000, pp. 1467-1477, vol. 150, No. 6.
Qualtiere, L. et al., "Effects of Ionic and Nonionic Detergents on Antigen-Antibody Reactions," J. Immunol., Nov. 1977, pp. 1645-1651, vol. 119.
Rajotte, D. et al., "Membrane Dipeptidase Is he Receptor for a Lung-targeting Peptide Identified by in vivo Phage Display," J. Bio. Chem., Apr. 23, 1999, pp. 11593-11598, vol. 274, No. 17.
Rosenberg, E. et al., "Destruction of Human Lymphoid Tissue-Culture Cell Lines by Human Peripheral Lymphocytes in 51Cr-Release Cellular Cytotoxicity Assays," J. Nat. Cancer Inst., Feb. 1974, pp. 345-352, vol. 52, No. 2.
Ruoslahti, E., "RGD and Other Recognition Sequences for Integrins," Annu. Rev. Cell Dev. Biol., 1996, pp. 697-715, vol. 12.
Ryder, K. et al., "An Enzyme Immunoassay Procedure for Cancer Antigen 125 Evaluated," Clin. Chem., 1988, pp. 2513-2516, vol. 34, No. 12.

(56) References Cited

OTHER PUBLICATIONS

Sakamoto, N. et al., "Inhibition of Angiogenesis and Tumor Growth by a Synthetic Laminin Peptide, CDPGYIGSR-NH2," Cancer Res., Feb. 1, 1991, pp. 903-906, vol. 51.
Sano, T. et al., "Immunohistochemical overexpression of p16 protein associated with intact retinoblastoma protein expression in cervical cancer and cervical intraepithelial neoplasia," Pathology Int., 1998, pp. 580-585, vol. 48.
Sano, T. et al., "Overexpression of p16 and p14ARF is associated with human papillomavirus infection in cervical squamous cell carcinoma and dysplasia," Pathology Int., 2002, pp. 375-383, vol. 52.
Sano, T., et al., "Expression Status of p16 Protein is Associated with Human Papillomavirus Oncogenic Potential in Cervical and Genital Lesions," Am. J. Pathol., 1998, pp. 1741-1748, vol. 153, No. 6.
Serrano, M. et al., "A new regulatory motif in cell-cycle control causing specific inhibition of cyclin D/CDK4," Nature, Dec. 16, 1993, pp. 704-707, vol. 366.
Shalaby, M. et al., "Development of Humanized Bispecific Antibodies Reactive with Cytotoxic Lymphocytes and Tumor Cells Overexpressing the HER2 Protooncogene," J. Exp. Med., Jan. 1992, pp. 217-225, vol. 175, The Rockefeller University Press.
Sherr, C., "The INK4a/ARF Network in Tumor Suppression," Nat. Rev. Mol. Cell Bio., Oct. 2001, pp. 731-737, vol. 2.
Shigemasa, K. et al., "p16 overexpression: a potential early indicator of transformation in ovarian carcinoma," J. Soc. Gynecol. Invest., 1997, pp. 95-102, vol. 4, No. 2.
Shim, C. et al., "Profiling of differentially expressed genes in human primary cervical cancer by complementary DNA expression array," Clin. Cancer Res., Dec. 1998, pp. 3045-3050, vol. 4.
Sivam, G. et al., "Therapeutic Efficacy of a Doxorubicin Immunoconjugate in a Preclinical Model of Spontaneous Metastatic Human Melanoma," Cancer Res., Jun. 1, 1995, pp. 2352-2356, vol. 55.
Sudarsanam, S., "Structural Diversity of Sequentially Identical Subsequences of Proteins: Identical Octapeptides Can Have Different Conformations," Proteins: Structure, Function, and Genetics, 1998, pp. 228-231, vol. 30, Wiley-Liss, Inc.
Suneja, S. et al., "Quantification of a neurotrophin receptor from submilligram quantities of brain tissue using Western blotting," Brain Res. Protocols, 1998, pp. 88-93, vol. 3.
Takeuchi, H. et al., "Altered p16/MTS1/CDKN2 and cyclin D1/PRAD-1 gene expression is associated with the prognosis of squamous cell carcinoma of the esophagus," Clin. Cancer Res., Dec. 1997, pp. 2229-2236, vol. 3.
Tam, S. et al., "Differential Expression and Cell Cycle Regulation of the Cyclin-dependent Kinase 4 Inhibitor p16Ink4," Cancer Res., Nov. 15, 1994, pp. 5816-5820, vol. 54.
Tsujie, M. et al., "Expression of Tumor Suppressor Gene p16INK4 Products in Primary Gastric Cancer," Oncology, 2000, pp. 126-136, vol. 58.
Wang, H. et al., "TIP-1 Translocation onto the Cell Plasma Membrane is a Molecular Biomarker of Tumor Response to Ionizing Radiation," PLoS ONE, Aug. 2010, pp. 1-12, vol. 5, No. 8, e12051.
Wentzensen, N. et al., "Identification of High-Grade Cervical Dysplasia by the Detection of p16INK4a in Cell Lysates Obtained From Cervical Samples," Cancer, Nov. 1, 2006, pp. 2307-2313, vol. 107, No. 9.
Wong, Y. et al., "Frequent loss of heterozygosity of chromosome 3 short arm detected by PCR-based microsatellite polymorphisms in cervical squamous cell carcinoma," Cancer Letters, 1997, pp. 161-164, vol. 115.
Wong, Y. et al., "p16INK4 and p15INK4B Alterations in Primary Gynecologic Malignancy," Gynecologic Onco., 1997, pp. 319-324, vol. 65, Article No. GO974669.
Xu, X. et al., "Cell cycle proteins PP5 associated with Rad9 and uses in screening for a bioactive agent," Database HCAPLUS on STN, 2001, Abstract WO01/64913, Accession No. 2001:661624, Registry No. 263887-03-02 for human gene rad9 for SEQ ID No. 8, 1 page.
Yokota, T. et al., "Rapid Tumor Penetration of a Single-Chain Fv and Comparison with Other Immunoglobulin Forms," Can. Res., Jun. 15, 1992, pp. 3402-3408, vol. 52.
Alewine, C. et al., "TIP-1 Has PDZ Scaffold Antagonist Activity," Mol. Biol. Cell, Oct. 2006, pp. 4200-4211, vol. 17, No. 10.
Brooks, B. et al., "CHARMM: The Biomolecular Simulation Program," J. Comput. Chem., Jul. 30, 2009, pp. 1545-1614, vol. 30, No. 10 (NIH Public Access Author Manuscript, 124 pages).
Collins, M. et al., "Mapping multiprotein complexes by affinity purification and mass spectrometry," Curr. Opin. Biotechnol., 2008, pp. 324-330, vol. 19, No. 4.
Diaz, R. et al., "Determining glioma response to radiation therapy using recombinant peptides," Expert Rev. Anticancer Ther., 2008, pp. 1787-1796, vol. 8, No. 11.
Han, Z. et al., "Noninvasive assessment of cancer response to therapy," Nat. Med., Mar. 2008, pp. 343-349, vol. 14, No. 3.
Han, M. et al., "The PDZ protein TIP-1 facilitates cell migration and pulmonary metastasis of human invasive breast cancer cells in athymic mice," Biochem. Biophys. Res. Commun., May 25, 2012, pp. 139-145, vol. 422, No. 1 (NIH Public Access Author Manuscript, 13 pages).
Jaboin, J. et al., "Using In Vivo Biopanning for the Development of Radiation-Guided Drug Delivery Systems," Methods Mol. Biol., Gene Ther. Cancer, 2009, pp. 285-300, vol. 542, Humana Press.
Kanamori, M. et al., "The PDZ Protein Tax-interacting Protein-1 Inhibits beta-Catenin Transcriptional Activity and Growth of Colorectal Cancer Cells," J. Biol. Chem., Oct. 3, 2003, pp. 38758-38764, vol. 278, No. 40.
Lowery, A. et al., "Tumor-targeted delivery of liposome-encapsulated doxorubicin by use of a peptide that selectively binds to irradiated tumors," J. Control Release, Feb. 28, 2011, pp. 117-124, vol. 150, No. 1 (NIH Public Access Author Manuscript, 15 pages).
Menon, R. et al., "Functional Implications of Structural Predictions for Alternative Splice Proteins Expressed in Her2/neu-Induced Breast Cancers," J. Proteome Res., Dec. 2, 2011, pp. 5503-5511, vol. 10, No. 12 (NIH Public Access Author Manuscript, 19 pages).
Newton, J. et al., "Phage Peptide Display," Handb. Exp. Pharmacol., 2008, pp. 145-163, vol. 185, Part 2.
Newton, J. et al., "In Vivo Bacteriophage Display for the Discovery of Novel Peptide-Based Tumor-Targeting Agents," Methods Mol. Biol.: Biosensors and Biodetection, 2009, pp. 275-290, vol. 504, Humana Press.
Oliver, A. et al., "The HPV16 E6 binding protein Tip-1 interacts with ARHGEF16, which activates Cdc42," Br. J. Cancer, 2011, pp. 324-331, vol. 104, No. 2.
Passarella, R. et al., "Recombinant Peptides as Biomarkers for Tumor Response to Molecular Targeted Therapy," Clin. Cancer Res., Oct. 15, 2009, pp. 6421-6429, vol. 15, No. 20 (NIH Public Access Author Manuscript, 25 pages).
Phillips, J. et al., "Scalable Molecular Dynamics with NAMD," J. Comput. Chem., Dec. 2005, pp. 1781-1802, vol. 26, No. 16 (NIH Public Access Author Manuscript, 43 pages).
Rangel, R. et al., "Combinatorial targeting and discovery of ligand-receptors in organelles of mammalian cells," Nat. Commun., 2012, pp. 1-10, vol. 3, No. 788.
Vithayathil, R. et al., "The Scope of Phage Display for Membrane Proteins," J. Mol. Biol., Dec. 9, 2011, pp. 499-510, vol. 414, No. 4 (NIH Public Access Author Manuscript, 18 pages).
Wu, C-C. et al., "Identification of a New Peptide for Fibrosarcoma Tumor Targeting and Imaging In Vivo," J. Biomed. Biotechnol., 2010, pp. 1-10, vol. 2010, Article 167045.
Xu, X. et al. "The tandem affinity purification method: An efficient system for protein complex purification and protein interaction identification," Protein Expr. Purif., 2010, pp. 149-156, vol. 72, No. 2.
Zang, L. et al., "Screening and Identification of a peptide specifically targeted to NCI-H1299 from a phage display peptide library," Cancer Letters, 2009, pp. 64-70, vol. 281, No. 1.
Zhang, J. et al., "Structural Basis of beta-Catenin Recognition by Tax-interacting Protein-1," J. Mol. Biol., 2008, pp. 255-263, vol. 384, No. 1.

* cited by examiner 24 hours post-injection
L hindlimb – 3Gy
R hindlimb – 0Gy 24 hours post-injection
L hindlimb – 3Gy
R hindlimb – 0Gy 48 hours post-injection
L hindlimb – 3Gy
R hindlimb – 0Gy Heavy chain: Leader sequence- Variable region DNA sequence ( 411 bp ) SEQ ID NO: 5

[illegible]

Amino acids sequence ( 137 AA ) SEQ ID NO:6

[illegible]

Light chain: Leader sequence- Variable region

DNA sequence ( 381 bp ) SEQ ID NO:7

[illegible]

Amino acids sequence ( 127 AA ) SEQ ID NO:8

[illegible]

FIG. 7

SEQ ID NO: 22

2A

FFGDFQREKHIRNSFSCSFLCGPAGHGPGETAAVWGQGTTVTVSSGGGGSGGGGSGGGGS
DIELTQSPSTMTASPGEKVTITCRASSSVSYMHWYQQKPGASPKPWIYDTSKLASGVPDRF
SGSGSGTSYSLTINNMEAEDAATYYCQQWNYPSTFGAGTKLEIKPAAAGAPVPYPDPLEPR
AA*TVESCLAKPHTENSFTNVWKDDKTLDRYANYEGCLWNATGVVVCTGDETQCYGTW
VPIGLAIPEN

SEQ ID NO: 23

2B

FQREKHIRNSFSCSPLCGPAGHGPGETAAVWGQGTTVTVSSGGGGSGGGGSGGGGSDIELT
QSPSTMTASPGEKVTITCRASSSVSYMHWYQQKPGASPKPWIYDTSKLASGVPDRFSGSGS
GTSYSLTINNMEAEDAATYYCQQWNYPSTFGAGTKLEIKPAAAGAPVPYPDPLEPRAA*T
VESCLAKPHTENSFTNVWKDDKTLDRYANYEGCLWNATGVVVCTGDETQCYGTWVPI

FIG. 22

ANTIBODIES TO TIP-1

CROSS REFERENCE TO RELATED APPLICATIONS

This application claims the priority of PCT Application PCT/US2012/048856, filed Jul. 30, 2012, which claims the priority of U.S. provisional application No. 61/513,333, filed Jul. 29, 2011, each of which is hereby incorporated by reference in its entirety.

GOVERNMENTAL RIGHTS

This invention was made with government support under grants R01-CA125757, R21-CA128456-01, R01-CA112385-01, and R01-CA88076, awarded by the National Institutes of Health (NIH). The government has certain rights in the invention.

FIELD OF INVENTION

The invention encompasses antibodies useful in the recognition of tumor cells and tumor specific delivery of drugs and therapies.

BACKGROUND OF THE INVENTION

In the United States, the probability that an individual, over the course of a lifetime, will develop or die from cancer is 1 in 2 for men and 1 in 3 for women. Tumor-specific drug delivery and therapy methods have the potential to reduce or prevent tumor growth in organisms allowing them to lead longer, healthier lives. Many anti-tumor drugs, however, are also toxic to non-tumor cells, resulting in hard to tolerate side-effects. Hence, there is a need in the art for a way to deliver anti-tumor agents specifically to tumor cells to reduce tumor cell growth.

SUMMARY OF THE INVENTION

One aspect of the present invention encompasses an isolated antibody that binds to GRP78. The antibody comprises a heavy chain variable domain comprising a CDR1, CDR2, and a CDR3, wherein the CDR3 comprises at least five contiguous amino acids of SEQ ID NO:17.

Another aspect of the present invention encompasses an isolated antibody that binds to TIP-1. The antibody comprises a heavy chain variable domain comprising a CDR1, CDR2, and a CDR3, wherein the CDR3 comprises at least five contiguous amino acids of SEQ ID NO:30.

Yet another aspect of the present invention encompasses a method of enhancing radiotherapy in a subject. The method comprising administering a pharmacologically effective amount of an antibody of the invention to a subject, such that radiotherapy is enhanced.

REFERENCE TO COLOR FIGURES

The application file contains at least one photograph executed in color. Copies of this patent application publication with color photographs will be provided by the Office upon request and payment of the necessary fee.

BRIEF DESCRIPTION OF THE FIGURES

FIG. 7 depicts the variable region sequences for anti-GRP78 antibody 2B6F9.

FIG. 22 depicts sequences of two anti-TIP-1 scFv antibody clones (SEQ ID NO:22—upper panel; SEQ ID NO:23—lower panel). Blue=leader sequence, Green=epitope tag.

DETAILED DESCRIPTION OF THE INVENTION

Figure 1:
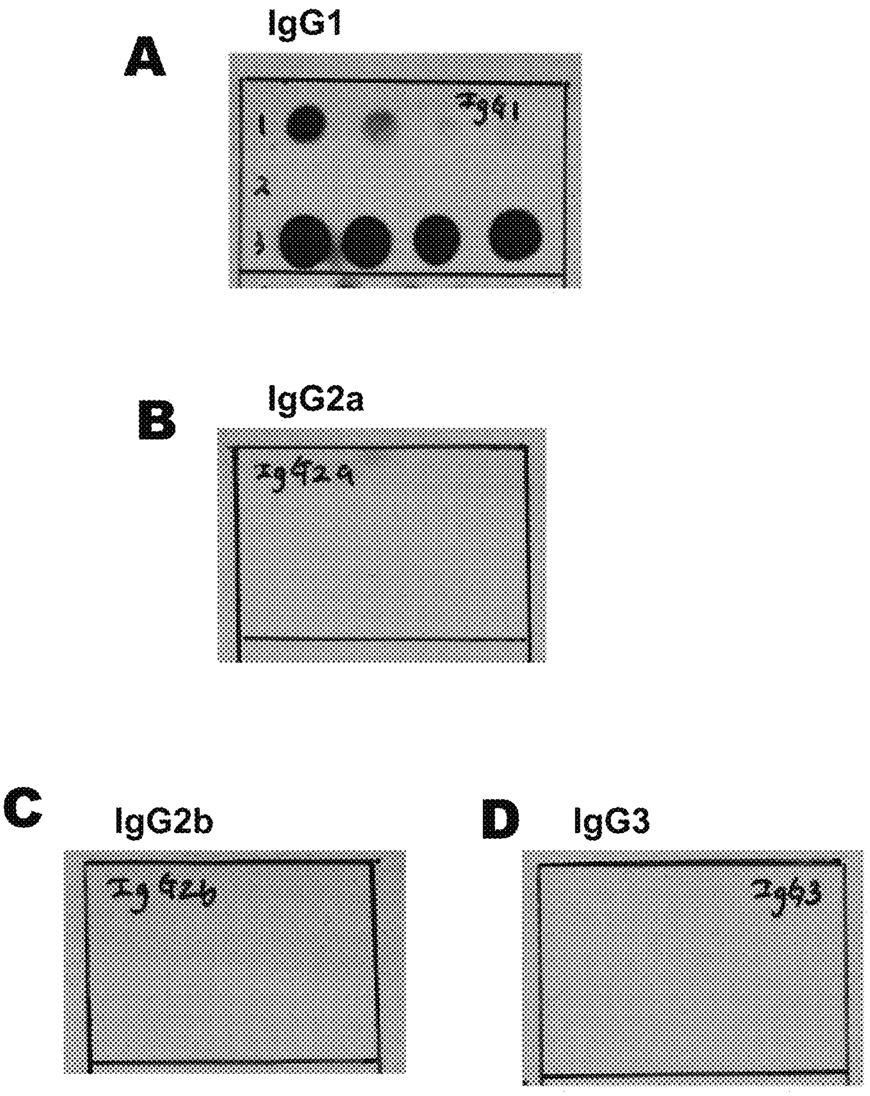
FIG. 1 depicts dotblots showing that anti-GRP78 antibody 2D6F9 is of the IgG1 isotype. (A) IgG1 dotblot. (B) IgG2a dotblot. (C) IgG2b dotblot. (D) IgG3 dotblot.

The present invention encompasses antibodies that recognize tumor cells. The antibodies may be used to provide tumor specific delivery, for instance, of drugs or therapeutic agents, as well as enhancing the efficacy of radiotherapy. In particular, the present invention provides for antibodies that bind to GRP78 and TIP-1. Advantageously, these antibodies specifically bind tumor cells and not normal cells.

In an exemplary embodiment, antibodies of the invention specifically bind to epitopes exposed on irradiated tumor related cells. For instance, antibodies of the invention may bind to extracellular, transmembrane or intracellular epitopes on irradiated tumor related cells.

I. Antibodies

The present invention encompasses antibodies that recognize tumor cells. In an aspect, antibodies useful herein include those antibodies which have been isolated, characterized, purified, are functional and have been recovered (obtained) for use in a functional therapeutic composition which is administered to a living patient.

The term "antibody" refers to an immunoglobulin molecule capable of specific binding to a target, such as a carbohydrate, polynucleotide, lipid, or polypeptide through at least one antigen recognition site. As used herein, an antibody encompasses not only intact polyclonal or monoclonal antibodies, but also fragments thereof (such as Fab, Fab', F(ab')2. Fv), single chain (scFv), mutants thereof, fusion proteins comprising an antibody portion, humanized antibodies, chimeric antibodies, diabodies, linear antibodies, single chain antibodies, multispecific antibodies (e.g., bispecific antibodies) and any other modified configuration of the immunoglobulin molecule that comprises an antigen recognition site of the required specificity.

An antibody includes an antibody of any class, such as IgG, IgA, or IgM (or sub-class thereof), or the antibody need not be of any particular class. As long as the protein retains the ability specifically to bind its intended target, it is included within the term "antibody."

Also included within the definition "antibody" for example are single chain forms, generally designated Fv or scFv, regions, of antibodies with this specificity. These scFvs comprise heavy and light chain variable regions connected by a linker. In most instances, but not all, the linker may be a peptide. A linker peptide is preferably from about 10 to 25 amino acids in length. Preferably, a linker peptide is rich in glycine, as well as serine or threonine. ScFvs can be used to facilitate phage display or can be used for flow cytometry, immunohistochemistry, or as targeting domains. Methods of making and using scFvs are known in the art.

The basic structural unit of an antibody useful herein comprises a tetramer. Each tetramer is composed of two identical pairs of polypeptide chains, each pair having one "light' (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function.

Depending on the antibody amino acid sequence of the constant domain of its heavy chains, immunoglobulins can be assigned to different classes. In mammals, heavy-chains are classified as alpha, delta, epsilon, gamma, or mu, and define the antibody's isotype as IgA, IgD, IgE, IgG, and IgM, respectively. Several of these isotypes may be further divided into subclasses (isotypes), e.g., IgG1, IgG2, IgG3, IgG4, IgA1 and IgA2. Light chains are classified as kappa and lambda.

The subunit structures and three-dimensional configurations of different classes of immunoglobulins are well known. Within light and heavy chains, the variable and constant regions are joined by a "J" region of about 12 or more amino acids, with the heavy chain also including a "D" region of about 10 more amino acids. The variable regions of each light/heavy chain pair form the antibody binding site. Thus, an intact antibody has two binding sites. The chains exhibit the same general structure of relatively conserved framework regions (FR) joined by three hypervariable regions, also called complementarily determining regions (hereinafter referred to as "CDRs.") The CDRs from the two chains are aligned by the framework regions, enabling binding to a specific epitope. From N-terminal to C-terminal, both light and heavy chains comprise the domains FR1, CDR1, FR2, CDR2, FR3, CDR3 and FR4 respectively. The assignment of amino acids to each domain is in accordance with known conventions (See, Kabat "Sequences of Proteins of Immunological Interest" National Institutes of Health, Bethesda, Md., 1987 and 1991; Chothia, et al, J. Mol. Bio. (1987) 196:901-917; Chothia, et al., Nature (1989) 342:878-883).

In some embodiments, the antibodies of the invention may be monoclonal antibodies. "Monoclonal antibody" refers to an antibody that is derived from a single copy or clone. A monoclonal antibody is not limited to antibodies produced through hybridoma technology. Monoclonal antibodies may be produced using e.g., hybridoma techniques well known in the art, as well as recombinant technologies, phage display technologies, synthetic technologies or combinations of such technologies and other technologies readily known in the art. A monoclonal antibody may encompass not only intact monoclonal antibodies and full-length monoclonal antibodies, but also fragments thereof (such as Fab, Fab', F(ab')2, Fv), single chain (scFv), mutants thereof, fusion proteins comprising an antibody portion, humanized monoclonal antibodies, chimeric monoclonal antibodies, and any other modified configuration of the immunoglobulin molecule that comprises an antigen recognition site of the required specificity and the ability to bind to an antigen. Furthermore, the monoclonal antibody may be labeled with a detectable label, immobilized on a solid phase and/or conjugated with a heterologous compound (e.g., an enzyme or toxin) according to methods known in the art.

Preferably, but not necessarily, the antibodies useful in the discovery are produced recombinantly, as manipulation of the typically murine or other non-human antibodies with the appropriate specificity is required in order to convert them to humanized form. Antibodies may or may not be glycosylated, though glycosylated antibodies are preferred. Antibodies are properly cross-linked via disulfide bonds, as is known.

Antibodies useful herein include those which are isolated, characterized, purified, functional and have been recovered (obtained) from a process for their preparation and thus available for use herein in a useful form in a therapeutically and medicinally sufficient amount.

In an aspect, antibodies of the invention are generated with appropriate specificity by standard techniques of immunization of mammals, forming hybridomas from the antibody-producing cells of said mammals or otherwise immortalizing them, and culturing the hybridomas or immortalized cells to assess them for the appropriate specificity. In the present case, such antibodies may be generated by immunizing a human, rabbit, rat or mouse, for example, with a peptide representing an epitope encompassing a region of the GRP78 or TIP-1 protein coding sequences or an appropriate subregion thereof. Materials for recombinant manipulation may be obtained by retrieving the nucleotide sequences encoding the desired antibody from the hybridoma or other cell that produces it. These nucleotide sequences may then be manipulated and isolated, characterized, purified and recovered to provide them in humanized form, if desired.

(a) Antibodies that Bind to GRP78

One aspect of the present invention encompasses an antibody that binds to GRP78.

(i) Heavy Chain Sequence

In one embodiment, such an antibody is encoded by a heavy chain variable region nucleic acid sequence that comprises at least about 60% homology to SEQ ID NO:5. In some embodiments, an antibody comprises at least 60, 65, 70, 75, 80, 85, 90, or 95% homology with SEQ ID NO: 5. In one embodiment, the heavy chain variable region nucleic acid sequence has at least about 95, 96, 97, 98, or 99% sequence homology with SEQ ID NO:5. In a preferred embodiment, the heavy chain variable region nucleic acid sequence encodes the amino acid sequence of SEQ ID NO:6.

In other embodiments, an isolated antibody of the present invention comprises a heavy chain variable region amino acid sequence with at least about 60% homology to SEQ ID NO: 6. In some embodiments, an antibody comprises at least 60, 65, 70, 75, 80, 85, 90, or 95% homology with SEQ ID NO: 6. In one embodiment, the heavy chain variable region nucleic acid sequence has at least about 95, 96, 97, 98, or 99% sequence homology with SEQ ID NO:6.

In certain embodiments, an antibody that binds to GRP78 is an isolated antibody that comprises at least one heavy chain variable domain complementary determining region (CDR) sequence. Typically, a heavy chain variable domain comprises three CDR sequences (CDR1, CDR2, and CDR3), separated by framework regions. In one embodiment, an antibody of the invention comprises a heavy chain CDR1 region that comprises at least five contiguous amino acids of SEQ ID NO: 15 (SFTGYFMN). For instance, the heavy chain CDR1 region may comprise 6, 7, or 8 contiguous amino acids of SEQ ID NO: 15. In another embodiment, an antibody of the invention comprises a heavy chain CDR1 region comprising SEQ ID NO:15.

In other embodiments, an antibody of the invention comprises a heavy chain CDR2 region that comprises at least five contiguous amino acids of SEQ ID NO: 16 (IGRIDPYNGNIFYNQ). For instance, the heavy chain CDR2 region may comprise 6, 7, 8, 9, 10, 11, 12, 13, 14, or 15 contiguous amino acids of SEQ ID NO: 16. In another embodiment, an antibody of the invention comprises a heavy chain CDR2 region comprising SEQ ID NO:16.

In yet another embodiment, an antibody of the invention comprises a heavy chain CDR3 region that comprises at least five contiguous amino acids of SEQ ID NO: 17 (AVYYCGRSYGNY). For instance, the heavy chain CDR3 region may comprise 6, 7, 8, 9, 10, 11, or 12 contiguous amino acids of SEQ ID NO: 17. In another embodiment, an antibody of the invention comprises a heavy chain CDR3 region comprising SEQ ID NO:17.

A heavy chain variable region of an antibody of the present invention may comprise a CDR1 of SEQ ID NO: 15 and a CDR2 of SEQ ID NO:16. In another embodiment, a heavy chain variable region of an antibody of the present invention may comprise a CDR1 of SEQ ID NO:15 and a CDR3 of SEQ ID NO: 17. In yet another embodiment, a heavy chain variable region of an antibody of the present invention may comprise a CDR2 of SEQ ID NO: 16 and a CDR3 of SEQ ID NO:17. In still another embodiment, a heavy chain variable region of an antibody of the present invention may comprise a CDR1 of SEQ ID NO:15, a CDR2 of SEQ ID NO:16, and a CDR3 of SEQ ID NO:17.

In each of the above embodiments, a CDR sequence may have one, two, or three amino acid substitutions. These substitutions may be conservative or non-conservative, providing the antibody specifically recognizes GRP78.

(ii) Light Chain Sequence

In an embodiment, such an antibody is encoded by a light chain variable region nucleic acid sequence that comprises at least about 60% homology to SEQ ID NO:7. In some embodiments, an antibody comprises at least 60, 65, 70, 75, 80, 85, 90, or 95% homology with SEQ ID NO: 7. In one embodiment, the light chain variable region nucleic acid sequence has at least about 95, 96, 97, 98, or 99% sequence homology with SEQ ID NO:7. In a preferred embodiment, the light chain variable region nucleic acid sequence encodes the amino acid sequence of SEQ ID NO:8.

In other embodiments, an isolated antibody of the present invention comprises a light chain variable region amino acid sequence with at least about 60% homology to SEQ ID NO: 8. In some embodiments, an antibody comprises at least 60, 65, 70, 75, 80, 85, 90, or 95% homology with SEQ ID NO: 8. In one embodiment, the heavy chain variable region nucleic acid sequence has at least about 95, 96, 97, 98, or 99% sequence homology with SEQ ID NO:8.

In certain embodiments, an antibody that binds to GRP78 is an isolated antibody that comprises at least one light chain variable domain complementary determining region (CDR) sequence. Typically, a light chain variable domain comprises three CDR sequences (CDR1, CDR2, and CDR3), separated by framework regions. In one embodiment, an antibody of the invention comprises a light chain CDR1 region that comprises at least five contiguous amino acids of SEQ ID NO: 18 (GETITINCRA). For instance, the light chain CDR1 region may comprise 6, 7, 8, 9, or 10 contiguous amino acids of SEQ ID NO: 18. In another embodiment, an antibody of the invention comprises a light chain CDR1 region that comprises SEQ ID NO:18.

In an alternative embodiment, an antibody of the invention comprises a light chain CDR2 region that comprises at least five contiguous amino acids of SEQ ID NO: 19 (KPGKTNKLLIYF). For instance, the light chain CDR2 region may comprise 6, 7, 8, 9, 10, 11, or 12 contiguous amino acids of SEQ ID NO: 19. In another embodiment, an antibody of the invention comprises a light chain CDR2 region that comprises SEQ ID NO:19.

In yet another embodiment, an antibody of the invention comprises a light chain CDR3 region that comprises at least five contiguous amino acids of SEQ ID NO: 20 (EPEDFAMYFCQQHNE). For instance, the light chain CDR3 region may comprise 6, 7, 8, 9, 10, 11, 12, 13, 14, or 15 contiguous amino acids of SEQ ID NO: 20. In another embodiment, an antibody of the invention comprises a light chain CDR3 region that comprises SEQ ID NO:20.

A light chain variable region of an antibody of the present invention may comprise a CDR1 of SEQ ID NO: 18 and a CDR2 of SEQ ID NO:19. In another embodiment, a light chain variable region of an antibody of the present invention may comprise a CDR1 of SEQ ID NO:18 and a CDR3 of SEQ ID NO: 20. In yet another embodiment, a light chain variable region of an antibody of the present invention may comprise a CDR2 of SEQ ID NO: 19 and a CDR3 of SEQ ID NO:20. In still another embodiment, a light chain variable region of an antibody of the present invention may comprise a CDR1 of SEQ ID NO:18, a CDR2 of SEQ ID NO:19, and a CDR3 of SEQ ID NO:20.

In each of the above embodiments, a CDR sequence may have one, two, or three amino acid substitutions. These substitutions may be conservative or non-conservative, providing the antibody specifically recognizes GRP78.

(iii) Preferred Embodiments

In preferred embodiments, an antibody of the invention is encoded by a heavy chain variable region nucleic acid sequence of SEQ ID NO:5 and a light chain variable region nucleic acid sequence of SEQ ID NO:7. In another preferred embodiment, an antibody of the invention is encoded by a heavy chain variable region nucleic acid that encodes SEQ ID NO:6 and a light chain variable region nucleic acid sequence that encodes SEQ ID NO:8. In still other preferred embodiments, an antibody of the invention comprises a heavy chain variable region of SEQ ID NO:6 and a light chain variable region of SEQ ID NO:8.

In an exemplary embodiment, an antibody of the invention may comprise a combination of CDR sequences listed in Table A below.

TABLE A

CDR combinations comprising antibodies that recognize GRP78

| | Heavy Chain Variable Region SEQ ID NOs | | | Light Chain Variable Region SEQ ID NOs | | |
|---|---|---|---|---|---|---|
| Combination | CDR1 | CDR2 | CDR3 | CDR1 | CDR2 | CDR3 |
| 1 | 15 | 16 | 17 | 18 | 19 | 20 |
| 2 | 15 | 16 | 17 | | 19 | 20 |
| 3 | 15 | 16 | 17 | 18 | | 20 |
| 4 | 15 | 16 | 17 | 18 | 19 | |
| 5 | 15 | 16 | 17 | | | 20 |
| 6 | 15 | 16 | 17 | | 19 | |
| 7 | 15 | 16 | 17 | 18 | | |
| 8 | 15 | 16 | 17 | | | |
| 9 | 15 | 16 | | 18 | 19 | 20 |
| 10 | 15 | 16 | | | 19 | 20 |
| 11 | 15 | 16 | | 18 | | 20 |
| 12 | 15 | 16 | | 18 | 19 | |
| 13 | 15 | 16 | | | | 20 |
| 14 | 15 | 16 | | | 19 | |
| 15 | 15 | 16 | | 18 | | |
| 16 | 15 | 16 | | | | |
| 17 | 15 | | 17 | 18 | 19 | 20 |
| 18 | 15 | | 17 | | 19 | 20 |
| 19 | 15 | | 17 | 18 | | 20 |
| 20 | 15 | | 17 | 18 | 19 | |
| 21 | 15 | | 17 | | | 20 |
| 22 | 15 | | 17 | | 19 | |
| 23 | 15 | | 17 | 18 | | |
| 24 | 15 | | 17 | | | |
| 25 | | 16 | 17 | 18 | 19 | 20 |
| 26 | | 16 | 17 | | 19 | 20 |
| 27 | | 16 | 17 | 18 | | 20 |
| 28 | | 16 | 17 | 18 | 19 | |
| 29 | | 16 | 17 | | | 20 |
| 30 | | 16 | 17 | | 19 | |
| 31 | | 16 | 17 | 18 | | |
| 32 | | 16 | 17 | | | |
| 33 | 15 | | | 18 | 19 | 20 |
| 34 | 15 | | | | 19 | 20 |
| 35 | 15 | | | 18 | | 20 |
| 36 | 15 | | | 18 | 19 | |
| 37 | 15 | | | | | 20 |
| 38 | 15 | | | | 19 | |
| 39 | 15 | | | 18 | | |
| 40 | 15 | | | | | |
| 41 | | 16 | | 18 | 19 | 20 |
| 42 | | 16 | | | 19 | 20 |
| 43 | | 16 | | 18 | | 20 |
| 44 | | 16 | | 18 | 19 | |
| 45 | | 16 | | | | 20 |
| 46 | | 16 | | | 19 | |
| 47 | | 16 | | 18 | | |
| 48 | | 16 | | | | |
| 49 | | | 17 | 18 | 19 | 20 |
| 50 | | | 17 | | 19 | 20 |
| 51 | | | 17 | 18 | | 20 |
| 52 | | | 17 | 18 | 19 | |
| 53 | | | 17 | | | 20 |
| 54 | | | 17 | | 19 | |
| 55 | | | 17 | 18 | | |
| 56 | | | 17 | | | |
| 57 | | | | 18 | 19 | 20 |
| 58 | | | | | 19 | 20 |
| 59 | | | | 18 | | 20 |
| 60 | | | | 18 | 19 | |
| 61 | | | | | | 20 |

TABLE A-continued

CDR combinations comprising antibodies that recognize GRP78

| | Heavy Chain Variable Region SEQ ID NOs | | | Light Chain Variable Region SEQ ID NOs | | |
|---|---|---|---|---|---|---|
| Combination | CDR1 | CDR2 | CDR3 | CDR1 | CDR2 | CDR3 |
| 62 | | | | | 19 | |
| 63 | | | | 18 | | |

(iv) GRP78 Epitopes

In one embodiment, an isolated antibody of the present invention that binds to GPR78 recognizes an epitope within the amino acid sequence of SEQ ID NO:1. For instance, a GRP78 antibody of the invention may recognize an epitope with 5, 6, 7, 8, or 9 contiguous amino acids of SEQ ID NO:1.

In yet another embodiment, an isolated antibody of the present invention that binds to GPR78 recognizes an epitope within the amino acid sequence of SEQ ID NO:2. For instance, a GRP78 antibody of the invention may recognize an epitope with 5, 6, 7, 8, or 9 contiguous amino acids of SEQ ID NO: 2.

In yet a further embodiment, an isolated antibody of the present invention that binds to GPR78 recognizes an epitope within the amino acid sequence of SEQ ID NO:3. For instance, a GRP78 antibody of the invention may recognize an epitope with 5, 6, 7, 8, 9, 10, 11, 12, 13, 14, or 15 contiguous amino acids of SEQ ID NO:3.

In an additional embodiment, an isolated antibody of the present invention that binds to GPR78 recognizes an epitope within the amino acid sequence of SEQ ID NO:4. For instance, a GRP78 antibody of the invention may recognize an epitope with 5, 6, 7, 8, or 9 contiguous amino acids of SEQ ID NO: 4.

(b) Antibodies that bind to TIP-1

One aspect of the present invention encompasses an antibody that binds to TIP-1.

(i) Heavy Chain Sequence

In one embodiment, such an antibody is encoded by a heavy chain variable region nucleic acid sequence that comprises at least about 60% homology to SEQ ID NO:24. In some embodiments, an antibody comprises at least 60, 65, 70, 75, 80, 85, 90, or 95% homology with SEQ ID NO: 24. In one embodiment, the heavy chain variable region nucleic acid sequence has at least about 95, 96, 97, 98, or 99% sequence homology with SEQ ID NO:24. In a preferred embodiment, the heavy chain variable region nucleic acid sequence encodes the amino acid sequence of SEQ ID NO:25.

In other embodiments, an isolated antibody of the present invention comprises a heavy chain variable region amino acid sequence with at least about 60% homology to SEQ ID NO: 25. In some embodiments, an antibody comprises at least 60, 65, 70, 75, 80, 85, 90, or 95% homology with SEQ ID NO: 25. In one embodiment, the heavy chain variable region nucleic acid sequence has at least about 95, 96, 97, 98, or 99% sequence homology with SEQ ID NO:25.

In certain embodiments, an antibody that binds to TIP-1 is an isolated antibody that comprises at least one heavy chain variable domain complementary determining region (CDR) sequence. Typically, a heavy chain variable domain comprises three CDR sequences (CDR1, CDR2, and CDR3), separated by framework regions. The assignment of amino acids to each domain is in accordance with known conventions (See, Kabat "Sequences of Proteins of Immunological Interest" National Institutes of Health, Bethesda, Md., 1987 and 1991; Chothia, et al, J. Mol. Bio. (1987) 196:901-917; Chothia, et al., Nature (1989) 342:878-883).

In one embodiment, an antibody of the invention comprises a heavy chain CDR1 region that comprises at least five contiguous amino acids of SEQ ID NO: 28 (SNYWMN). For instance, the heavy chain CDR1 region may comprise 6 contiguous amino acids of SEQ ID NO: 28. In another embodiment, an antibody of the invention comprises a heavy chain CDR1 region comprising SEQ ID NO:28.

In other embodiments, an antibody of the invention comprises a heavy chain CDR2 region that comprises at least five contiguous amino acids of SEQ ID NO: 29 (QIRLKSDNYATHY). For instance, the heavy chain CDR2 region may comprise 6, 7, 8, 9, 10, 11, 12, or 13 contiguous amino acids of SEQ ID NO: 29. In another embodiment, an antibody of the invention comprises a heavy chain CDR2 region comprising SEQ ID NO:29.

In yet another embodiment, an antibody of the invention comprises a heavy chain CDR3 region that comprises at least five contiguous amino acids of SEQ ID NO: 30 (GIYYCLLYY). For instance, the heavy chain CDR3 region may comprise 6, 7, 8, or 9 contiguous amino acids of SEQ ID NO: 30. In another embodiment, an antibody of the invention comprises a heavy chain CDR3 region comprising SEQ ID NO:30.

A heavy chain variable region of an antibody of the present invention may comprise a CDR1 of SEQ ID NO:28 and a CDR2 of SEQ ID NO:29. In another embodiment, a heavy chain variable region of an antibody of the present invention may comprise a CDR1 of SEQ ID NO:28 and a CDR3 of SEQ ID NO:30. In yet another embodiment, a heavy chain variable region of an antibody of the present invention may comprise a CDR2 of SEQ ID NO:29 and a CDR3 of SEQ ID NO:30. In still another embodiment, a heavy chain variable region of an antibody of the present invention may comprise a CDR1 of SEQ ID NO:28, a CDR2 of SEQ ID NO:29, and a CDR3 of SEQ ID NO:30.

In each of the above embodiments, a CDR sequence may have one, two, or three amino acid substitutions. These substitutions may be conservative or non-conservative, providing the antibody specifically recognizes TIP-1.

(ii) Light Chain Sequence

In an embodiment, such an antibody is encoded by a light chain variable region nucleic acid sequence that comprises at least about 60% homology to SEQ ID NO:26. In some embodiments, an antibody comprises at least 60, 65, 70, 75, 80, 85, 90, or 95% homology with SEQ ID NO:26. In one embodiment, the light chain variable region nucleic acid sequence has at least about 95, 96, 97, 98, or 99% sequence homology with SEQ ID NO:26. In a preferred embodiment, the light chain variable region nucleic acid sequence encodes the amino acid sequence of SEQ ID NO:27.

In other embodiments, an isolated antibody of the present invention comprises a light chain variable region amino acid sequence with at least about 60% homology to SEQ ID NO:27. In some embodiments, an antibody comprises at least 60, 65, 70, 75, 80, 85, 90, or 95% homology with SEQ ID NO:27. In one embodiment, the heavy chain variable region nucleic acid sequence has at least about 95, 96, 97, 98, or 99% sequence homology with SEQ ID NO:27.

In certain embodiments, an antibody that binds to GRP78 is an isolated antibody that comprises at least one light chain variable domain complementary determining region (CDR) sequence. Typically, a light chain variable domain comprises three CDR sequences (CDR1, CDR2, and CDR3), separated by framework regions. The assignment of amino acids to each domain is in accordance with known conventions (See, Kabat "Sequences of Proteins of Immunological Interest" National Institutes of Health, Bethesda, Md., 1987 and 1991; Chothia, et al, J. Mol. Bio. (1987) 196:901-917; Chothia, et al., Nature (1989) 342:878-883).

In one embodiment, an antibody of the invention comprises a light chain CDR1 region that comprises at least five contiguous amino acids of SEQ ID NO: 31 (SQSLVHSNG). For instance, the light chain CDR1 region may comprise 6, 7, 8, or 9 contiguous amino acids of SEQ ID NO:31. In another embodiment, an antibody of the invention comprises a light chain CDR1 region that comprises SEQ ID NO:31.

In an alternative embodiment, an antibody of the invention comprises a light chain CDR2 region that comprises at least five contiguous amino acids of SEQ ID NO:32 (KLLIYKVSNRF). For instance, the light chain CDR2 region may comprise 6, 7, 8, 9, 10, or 11 contiguous amino acids of SEQ ID NO:32. In another embodiment, an antibody of the invention comprises a light chain CDR2 region that comprises SEQ ID NO:32.

In yet another embodiment, an antibody of the invention comprises a light chain CDR3 region that comprises at least five contiguous amino acids of SEQ ID NO:33 (GVYFCSQST). For instance, the light chain CDR3 region may comprise 6, 7, 8, or 9 contiguous amino acids of SEQ ID NO:33. In another embodiment, an antibody of the invention comprises a light chain CDR3 region that comprises SEQ ID NO:33.

A light chain variable region of an antibody of the present invention may comprise a CDR1 of SEQ ID NO:31 and a CDR2 of SEQ ID NO:32. In another embodiment, a light chain variable region of an antibody of the present invention may comprise a CDR1 of SEQ ID NO:31 and a CDR3 of SEQ ID NO:33. In yet another embodiment, a light chain variable region of an antibody of the present invention may comprise a CDR2 of SEQ ID NO:32 and a CDR3 of SEQ ID NO:33. In still another embodiment, a light chain variable region of an antibody of the present invention may comprise a CDR1 of SEQ ID NO:31, a CDR2 of SEQ ID NO:32, and a CDR3 of SEQ ID NO:33.

In each of the above embodiments, a CDR sequence may have one, two, or three amino acid substitutions. These substitutions may be conservative or non-conservative, providing the antibody specifically recognizes TIP-1.

(iii) Preferred Embodiments

In preferred embodiments, an antibody of the invention is encoded by a heavy chain variable region nucleic acid sequence of SEQ ID NO:24 and a light chain variable region nucleic acid sequence of SEQ ID NO:26. In another preferred embodiment, an antibody of the invention is encoded by a heavy chain variable region nucleic acid that encodes SEQ ID NO:25 and a light chain variable region nucleic acid sequence that encodes SEQ ID NO:27. In still other preferred embodiments, an antibody of the invention comprises a heavy chain variable region of SEQ ID NO:25 and a light chain variable region of SEQ ID NO:27. In an exemplary embodiment, an antibody of the invention may comprise a combination of CDR sequences listed in Table B below.

TABLE B

CDR combinations comprising antibodies that recognize TIP-1

| | Heavy Chain Variable Region SEQ ID NOs | | | Light Chain Variable Region SEQ ID NOs | | |
|---|---|---|---|---|---|---|
| Combination | CDR1 | CDR2 | CDR3 | CDR1 | CDR2 | CDR3 |
| 1 | 28 | 29 | 30 | 31 | 32 | 33 |
| 2 | 28 | 29 | 30 | | 32 | 33 |
| 3 | 28 | 29 | 30 | 31 | | 33 |
| 4 | 28 | 29 | 30 | 31 | 32 | |
| 5 | 28 | 29 | 30 | | | 33 |
| 6 | 28 | 29 | 30 | | 32 | |
| 7 | 28 | 29 | 30 | 31 | | |
| 8 | 28 | 29 | 30 | | | |
| 9 | 28 | 29 | | 31 | 32 | 33 |
| 10 | 28 | 29 | | | 32 | 33 |
| 11 | 28 | 29 | | 31 | | 33 |
| 12 | 28 | 29 | | 31 | 32 | |
| 13 | 28 | 29 | | | | 33 |
| 14 | 28 | 29 | | | 32 | |
| 15 | 28 | 29 | | 31 | | |
| 16 | 28 | 29 | | | | |
| 17 | 28 | | 30 | 31 | 32 | 33 |
| 18 | 28 | | 30 | | 32 | 33 |
| 19 | 28 | | 30 | 31 | | 33 |
| 20 | 28 | | 30 | 31 | 32 | |
| 21 | 28 | | 30 | | | 33 |
| 22 | 28 | | 30 | | 32 | |
| 23 | 28 | | 30 | 31 | | |
| 24 | 28 | | 30 | | | |
| 25 | | 29 | 30 | 31 | 32 | 33 |
| 26 | | 29 | 30 | | 32 | 33 |
| 27 | | 29 | 30 | 31 | | 33 |
| 28 | | 29 | 30 | 31 | 32 | |
| 29 | | 29 | 30 | | | 33 |
| 30 | | 29 | 30 | | 32 | |
| 31 | | 29 | 30 | 31 | | |
| 32 | | 29 | 30 | | | |
| 33 | 28 | | | 31 | 32 | 33 |
| 34 | 28 | | | | 32 | 33 |
| 35 | 28 | | | 31 | | 33 |
| 36 | 28 | | | 31 | 32 | |
| 37 | 28 | | | | | 33 |
| 38 | 28 | | | | 32 | |
| 39 | 28 | | | 31 | | |
| 40 | 28 | | | | | |
| 41 | | 29 | | 31 | 32 | 33 |
| 42 | | 29 | | | 32 | 33 |
| 43 | | 29 | | 31 | | 33 |
| 44 | | 29 | | 31 | 32 | |
| 45 | | 29 | | | | 33 |
| 46 | | 29 | | | 32 | |
| 47 | | 29 | | 31 | | |
| 48 | | 29 | | | | |
| 49 | | | 30 | 31 | 32 | 33 |
| 50 | | | 30 | | 32 | 33 |
| 51 | | | 30 | 31 | | 33 |
| 52 | | | 30 | 31 | 32 | |
| 53 | | | 30 | | | 33 |
| 54 | | | 30 | | 32 | |
| 55 | | | 30 | 31 | | |
| 56 | | | 30 | | | |
| 57 | | | | 31 | 32 | 33 |
| 58 | | | | | 32 | 33 |
| 59 | | | | 31 | | 33 |
| 60 | | | | 31 | 32 | |
| 61 | | | | | | 33 |
| 62 | | | | | 32 | |
| 63 | | | | 31 | | |

(iv) TIP-1 Epitopes

In one embodiment, the isolated antibody of the present invention that binds to TIP-1 recognizes an epitope within the amino acid sequence of SEQ ID NO:9. For instance, a TIP-1 antibody of the invention may recognize an epitope with 5, 6, 7, 8, or 9 contiguous amino acids of SEQ ID NO: 9.

In yet another embodiment, the isolated antibody of the present invention that binds to TIP-1 recognizes an epitope within the amino acid sequence of SEQ ID NO:10. For instance, a TIP-1 antibody of the invention may recognize an epitope with 5, 6, 7, 8, or 9 contiguous amino acids of SEQ ID NO: 10.

In yet a further embodiment, the isolated antibody of the present invention that binds to TIP-1 recognizes an epitope within the amino acid sequence of SEQ ID NO:11. For instance, a TIP-1 antibody of the invention may recognize an epitope with 5, 6, 7, 8, 9, 10, 11, 12, 13, 14, or 15 contiguous amino acids of SEQ ID NO:11.

In an additional embodiment, the isolated antibody of the present invention that binds to TIP-1 recognizes an epitope within the amino acid sequence of SEQ ID NO:12. For instance, a TIP-1 antibody of the invention may recognize an epitope with 5, 6, 7, 8, or 9 contiguous amino acids of SEQ ID NO: 12.

Yet another embodiment provides for the isolated antibody of the present invention that binds to TIP-1, wherein the antibody recognizes an epitope within the amino acid sequence of SEQ ID NO: 13. For instance, a TIP-1 antibody of the invention may recognize an epitope with 5, 6, 7, 8, 9, or 10 contiguous amino acids of SEQ ID NO: 13.

In still another embodiment, the isolated antibody of the present invention that binds to TIP-1 recognizes an epitope within the amino acid sequence of SEQ ID NO:14. For instance, a TIP-1 antibody of the invention may recognize an epitope with 5, 6, 7, 8, 9, 10, 11, or 12 contiguous amino acids of SEQ ID NO:14.

In another embodiment, the isolated antibody of the present invention that binds to TIP-1 recognizes an epitope within the amino acid sequence of SEQ ID NO:21. For instance, a TIP-1 antibody of the invention may recognize an epitope with 5, 6, 7, 8, or 9 contiguous amino acids of SEQ ID NO: 21.

In yet another embodiment, an isolated antibody of the invention that binds to TIP-1 is an scFv antibody encoded by a nucleic acid sequence that encodes SEQ ID NO:22 (FIG. 22).

In another embodiment, an isolated antibody of the invention that binds to TIP-1 is an scFv antibody encoded by a nucleic acid sequence that encodes SEQ ID NO:23 (FIG. 22).

Each of the sequences referred to above may be found in Table C below.

TABLE C

| SEQ ID NO: | Sequence |
|---|---|
| 1 | MLLLLSAARA |
| 2 | MKLSLVAAML |
| 3 | MKLSLVAAMLLLLSAARA |
| 4 | EKNILVFDLG |
| 5 | GAGGTTCAGCTGCAGCAGTCTGGACCTGAGCTGGTGAAGCC TGGGGCTTCAGTGAAGATATCCTGCAAGGCTTCTGGTTACTC ATTTACTGGCTACTTTATGAACTGGGTGAAGCAGAGCCATGG AAAGAGCCTTGAGTGGATTGGACGTATTGATCCTTACAATGG TAATATTTTCTACAACCAGAAGTTCAAGGGCAAGGCCACATTG ACTGTGGACAAATCCTCTAGCACAGCCCACACGGAGCTCCTG AGCCTGACATCTGAGGACTCTGCAGTCTATTATTGTGGAAGG TCCTATGGTAACTATGCTTTGGACTACTGGGGTCAAGGAACC TCAGTCACCGTCTCCTCA |

TABLE C-continued

| SEQ ID NO: | Sequence |
|---|---|
| 6 | EVQLQQSGPELVKPGASVKISCKASGYSFTGYFMNWVKQSHGK<br>SLEWIGRIDPYNGNIFYNQKFKGKATLTVDKSSSTAHTELLSLTS<br>EDSAVYYCGRSYGNYALDYWGQGTSVTVSS |
| 7 | GATGTCCAGATAACCCAGTCTCCATCTTATCTTGCTGCATCTC<br>CTGGAGAAACCATTACTATTAATTGCAGGGCAAGTAAGAGCA<br>TTAGCAAATATTTAGCCTGGTATCAAGAGAAACCTGGGAAAAC<br>TAATAAGCTTCTTATCTACTTTGGATCCACTTTGCAATCTGGG<br>ATTCCATCAAGGTTCAGTGGCAGTGGATCTGGTACAGATTTC<br>ACTCTCACCATCAGTAGCCTGGAGCCTGAAGATTTTGCAATG<br>TATTTCTGTCAACAGCATAATGAATACCCGTACACGTTCGGAG<br>GGGGGACCAAGCTGGAAATGAAA |
| 8 | DVQITQSPSYLAASPGETITINCRASKSISKYLAWYQEKPGKTNK<br>LLIYFGSTLQSGIPSRFSGSGSGTDFTLTISSLEPEDFAMYFCQQ<br>HNEYPYTFGGGTKLEMK |
| 9 | QNPFSEDKTD |
| 10 | IDQDPSQNPF |
| 11 | IDQDPSQNPFSEDKTD |
| 12 | EIAGLQIGDK |
| 13 | IGDKIMQVNG |
| 14 | EIAGLQIGDKIMQVNG |
| 15 | SFTGYFMN |
| 16 | IGRIDPYNGNIFYNQ |
| 17 | AVYYCGRSYGNY |
| 18 | GETITINCRA |
| 19 | KPGKTNKLLIYF |
| 20 | EPEDFAMYFCQQHNE |
| 21 | QPVTAVVQRV |
| 22 | FFGDFQREKIIIRNSFSCSFLCGPAGHGPGETAAVWGQGTTVTV<br>SSGGGGSGGGGSGGGGSDIELTQSPSTMTASPGEKVTITCRAS<br>SSVSYMHWYQQKPGASPKPWIYDTSKLASGVPDRFSGSGSGT<br>SYSLTINNMEAEDAATYYCQQWNYPSTFGAGTKLEIKPAAAGAP<br>VPYPDPLEPRAATVESCLAKPHTENSFTNVWKDDKTLDRYANY<br>EGCLWNATGVVVCTGDETQCYGTWVPIGLAIPEN |
| 23 | FQREKIIIRNSFSCSFLCGPAGHGPGETAAVWGQGTTVTVSSGG<br>GGSGGGGSGGGGSDIELTQSPSTMTASPGEKVTITCRASSSVS<br>YMHWYQQKPGASPKPWIYDTSKLASGVPDRFSGSGSGTSYSL<br>TINNMEAEDAATYYCQQWNYPSTFGAGTKLEIKPAAAGAPVPYP<br>DPLEPRAATVESCLAKPHTENSFTNVWKDDKTLDRYANYEGCL<br>WNATGVVVCTGDETQCYGTWVPI |
| 24 | GAAGTGAAGCTTGAGGAGTCTGGAGGAGGCTTGGTGCAACC<br>TGGAGGATCCATGAAACTCTCCTGTGTTGCCTCTGGATTCAC<br>TTTCAGTAACTACTGGATGAACTGGGTCCGCCAGTCTCCAGA<br>GAAGGGGCTTGAGTGGGTTGCTCAAATTAGATTGAAATCTGA<br>TAATTATGCAACACATTATGCGGAGTCTGTGAAAGGGAGGTT<br>CACCATCTCAAGAGATGATTCCAAAAGTAGTGTCTACCTGCAA<br>ATGAACAACTTAAGGGCTGAAGACACTGGAATTTATTACTGCT<br>TACTTTACTACGGTCCTAGCGGGACTGCTTACTGGGGCCAAG<br>GGACTCTGGTCACTGTCTCTGCA |
| 25 | EVKLEESGGGLVQPGGSMKLSCVASGFTFSNYWMNWVRQSPE<br>KGLEWVAQIRLKSDNYATHYAESVKGRFTISRDDSKSSVYLQMN<br>NLRAEDTGIYYCLLYYGPSGTAYWGQGTLVTVSA |
| 26 | GATGTTGTGATGACCCAAACTCCACTCTCCCTGCCTGTCAGT<br>CTTGGAGATCAAGCCTCCATCTCTTGCAGATCTAGTCAGAGC<br>CTTGTACACAGTAATGGAAACACCTATTTACATTGGTACCTGC<br>AGAAGCCAGGCCAGTCTCCAAAGCTCCTGATCTACAAAGTTT<br>CCAACCGATTTTCTGGGGTCCCAGACAGGTTCAGTGGCAGTG<br>GATCAGGGACAGATTTCACACTCAAGATCAGCAGAGTGGAGG<br>CTGAGGATCTGGGAGTTTATTTCTGCTCTCAAAGTACACATGT<br>TCCTCGGACGTTCGGTGGAGGCACCAAGCTGGAAATCAAAC<br>GG |
| 27 | DVVMTQTPLSLPVSLGDQASISCRSSQSLVHSNGNTYLHWYLQ<br>KPGQSPKLLIYKVSNRFSGVPDRFSGSGSGTDFTLKISRVEAED<br>LGVYFCSQSTHVPRTFGGGTKLEIKR |
| 28 | SNYWMN |
| 29 | QIRLKSDNYATHY |
| 30 | GIYYCLLYY |
| 31 | SQSLVHSNG |
| 32 | KLLIYKVSNRF |
| 33 | GVYFCSQST |

(c) Humanized Antibodies

The antibodies of the present invention may also be chimeric antibodies. Preferably, these chimeric antibodies involve the merging of a portion of a monoclonal antibody with antibody-producing DNA in living cells to produce a monoclonal antibody that has material from more than one species of animal. This procedure is well known in the art and any known method to produce chimeric antibodies is suitable for purposes of the present invention. In a preferred embodiment, the chimeric antibody comprises mouse elements conjugated to the genetic material of another species. In a particularly preferred embodiment, the chimeric antibody comprises mouse and human elements to form humanized antibodies. The process of humanization decreases the potential for the antibody to induce an immune response in a human host.

As used herein "humanized antibody" includes an anti-GRP78 or anti-TIP-1 antibody that is composed partially or fully of amino acid sequences derived from a human antibody germline by altering the sequence of an antibody having non-human complementarity determining regions ("CDR"). The simplest such alteration may consist simply of substituting the constant region of a human antibody for the murine constant region, thus resulting in a human/murine chimera which may have sufficiently low immunogenicity to be acceptable for pharmaceutical use. Preferably, however, the variable region of the antibody and even the CDR is also humanized by techniques that are by now well known in the art. The framework regions of the variable regions are substituted by the corresponding human framework regions leaving the non-human CDR substantially intact, or even replacing the CDR with sequences derived from a human genome. CDRs may also be randomly mutated such that binding activity and affinity for GRP78 or TIP-1 is maintained or enhanced in the context of fully human germline framework regions or framework regions that are substantially human. Substantially human frameworks have at least 90%, 95%, or 99% sequence identity with a known human framework sequence. Fully useful human antibodies are produced in genetically modified mice whose immune systems have been altered to correspond to human immune systems. As mentioned above, it is sufficient for use in the methods of this discovery, to employ an immunologically specific fragment of the antibody, including fragments representing single chain forms.

If desired, the design of humanized immunoglobulins may be carried out as follows. When an amino acid falls under the following category, the framework amino acid of a human immunoglobulin to be used (acceptor immunoglobulin) is replaced by a framework amino acid from a CDR-providing nonhuman immunoglobulin (donor immunoglobulin): (a) the amino acid in the human framework region of the acceptor immunoglobulin is unusual for human immunoglobulin at that position, whereas the corresponding amino acid in the donor immunoglobulin is typical for human immunoglobulin at that position; (b) the position of the amino acid is immediately adjacent to one of the CDRs; or (c) any side chain atom of a framework amino acid is within about 5-6 angstroms (center-to-center) of any atom of a CDR amino acid in a three dimensional immunoglobulin model (Queen, et al., op. cit., and Co, ct al, Proc. Natl. Acad. Sci. USA (1991) 88:2869). When each of the amino acids in the human framework region of the acceptor immunoglobulin and a corresponding amino acid in the donor immunoglobulin is unusual for human immunoglobulin at that position, such an amino acid is replaced by an amino acid typical for human immunoglobulin at that position.

One embodiment of the present invention encompasses a humanized antibody that binds to GRP78. In particular, an embodiment of the invention encompasses a humanized antibody where amino acids in the framework region of either the heavy or light chain variable regions are humanized, leaving the CDRs intact. For instance, in one embodiment, an antibody may comprise a combination of CDRs listed in Table A, and a humanized framework region. In another embodiment, the sequence of one or more CDR regions may be humanized as well as the framework region.

In an exemplary embodiment, a humanized GRP78 antibody recognizes at least one epitope from the group consisting of SEQ ID NO:1, 2, 3, or 4.

In an alternative embodiment, the present invention encompasses a humanized antibody that binds to TIP-1. In particular, an embodiment of the invention encompasses a humanized antibody where amino acids in the framework region of either the heavy or light chain variable regions are humanized, leaving the CDRs intact. For instance, in one embodiment, an antibody may comprise a combination of CDRs listed in Table B, and a humanized framework region. In another embodiment, the sequence of one or more CDR regions may be humanized as well as the framework region.

In an exemplary embodiment, a humanized TIP-1 antibody recognizes at least one epitope from the group consisting of SEQ ID NO:9, 10, 11, 12, 13, 14, or 21.

In another alternative embodiment, the present invention encompasses a scFV antibody that binds TIP-1.

(d) Antibody Conjugates

In another aspect, an antibody of the present invention is conjugated to a therapeutic agent. In some embodiments, a scFv of the present invention is conjugated to a therapeutic agent. The therapeutic agent preferably reduces or interferes with tumor growth or otherwise reduces the effect of the tumor within the body or organism. A therapeutic agent that reduces the symptoms produced by the tumor or reduces tumor growth is suitable for the present invention.

Additionally, any therapeutic agent that reduces the symptoms associated with tumor cell growth will work for purposes of the present invention. Non-limiting examples of therapeutic agents may include drugs, therapeutic compounds, genetic materials, metals (such as radioactive isotopes), proteins, peptides, carbohydrates, lipids, steroids, nucleic acid based materials, or derivatives, analogues, or combinations thereof in their native form or derivatized with hydrophobic or charged moieties to enhance incorporation or adsorption into a cell. Such therapeutic agents may be water soluble or may be hydrophobic. Non-limiting examples of therapeutic agents may include immune-related agents, thyroid agents, respiratory products, antineoplastic agents, anti-helmintics, anti-malarials, mitotic inhibitors, hormones, anti-protozoans, anti-tuberculars, cardiovascular products, blood products, biological response modifiers, anti-fungal agents, vitamins, peptides, anti-allergic agents, anti-coagulation agents, circulatory drugs, metabolic potentiators, anti-virals, anti-anginals, antibiotics, anti-inflammatories, anti-rheumatics, narcotics, cardiac glycosides, neuromuscular blockers, sedatives, local anesthetics, general anesthetics, or radioactive atoms or ions. Non-limiting examples of therapeutic agents are included in Table D below. An isolated antibody of the present invention may be conjugated to one, two, three, four, or five therapeutic agents. Methods of conjugating an antibody to a therapeutic agent are known in the art. Generally speaking, the conjugation should not interfere with the antibody recognizing its target, and should not interfere with the active site of the target. In some instances, a scFv may be generated with a cleavable linkage between the scFv and therapeutic agent. Such a linker may allow release of the therapeutic agent at a specific cellular location.

TABLE D

Non-limiting Examples of Therapeutic Agents

| Therapeutic Agent | Non-limiting examples |
|---|---|
| Immune-related agents | immune serums, antitoxins, antivenoms bacterial vaccines, viral vaccines, rabies prophylaxis products |
| thyroid agents | iodine products and anti-thyroid agents |
| respiratory products | xanthine derivatives theophylline and aminophylline |
| antineoplastic agents | platinum compounds (e.g., spiroplatin, cisplatin, and carboplatin), methotrexate, fluorouracil, adriamycin, mitomycin, ansamitocin, bleomycin, cytosine arabinoside, arabinosyl adenine, mercaptopolylysine, vincristine, busulfan, chlorambucil, melphalan (e.g., PAM, L-PAM or phenylalanine mustard), mercaptopurine, mitotane, procarbazine hydrochloride dactinomycin (actinomycin D), daunorubicin hydrochloride, doxorubicin hydrochloride, paclitaxel and other taxenes, rapamycin, manumycin A, TNP-470, plicamycin (mithramycin), aminoglutethimide, estramustine phosphate sodium, flutamide, leuprolide acetate, megestrol acetate, tamoxifen citrate, testolactone, |

TABLE D-continued

| Non-limiting Examples of Therapeutic Agents | |
|---|---|
| Therapeutic Agent | Non-limiting examples |
| | trilostane, amsacrine (m-AMSA), asparaginase (L-asparaginase) Erwina asparaginase, interferon α-2a, interferon α-2b, teniposide (VM-26), vinblastine sulfate (VLB), vincristine sulfate, bleomycin sulfate, hydroxyurea, procarbazine, and dacarbazine |
| anti-helmintics | pyrantel pamoate, piperazine, tetrachloroethylene, thiabendazole, niclosamide |
| antimalarials | Chloroquine, amodiaquine, antifolate drugs, proguanil (chloroguanide), mefloquine, quinine, halofantrine, artemesinin and derivaties, primaquine, doxycycline, tetracycline, and clindamycin |
| mitotic inhibitors | etoposide, colchicine, and the vinca alkaloids |
| hormones | androgens, progestins, estrogens and antiestrogens, growth hormone, melanocyte stimulating hormone, estradiol, beclomethasone dipropionate, betamethasone, betamethasone acetate and betamethasone sodium phosphate, vetamethasone disodium phosphate, vetamethasone sodium phosphate, cortisone acetate, dexamethasone, dexamethasone acetate, dexamethasone sodium phosphate, flunisolide, hydrocortisone, hydrocortisone acetate, hydrocortisone cypionate, hydrocortisone sodium phosphate, hydrocortisone sodium succinate, methylprednisolone, methylprednisolone acetate, methylprednisolone sodium succinate, paramethasone acetate, prednisolone, prednisolone acetate, prednisolone sodium phosphate, prednisolone tebutate, prednisone, triamcinolone, triamcinolone acetonide, triamcinolone diacetate, triamcinolone hexacetonide, fludrocortisone acetate, oxytocin, vassopressin, glucagon and their derivatives |
| antiprotozoans | chloroquine, hydroxychloroquine, metronidazole, quinine and meglumine antimonite |
| antituberculars | para-aminosalicylic acid, isoniazid, capreomycin sulfate cycloserine, ethambutol hydrochloride ethionamide, pyrazinamide, rifampin, and streptomycin sulfate |
| cardiovascular products | chelating agents and mercurial diuretics and cardiac glycosides |
| blood products | parenteral iron, hemin, hematoporphyrins and their derivatives |
| biological response modifiers | muramyldipeptide, muramyltripeptide, microbial cell wall components, lymphokines (e.g., bacterial endotoxin such as lipopolysaccharide, macrophage activation factor), sub-units of bacteria (such as Mycobacteria, Corynebacteria), the synthetic dipeptide N-acetyl-muramyl-L-alanyl-D-isoglutamine |
| anti-fungal agents | ketoconazole, nystatin, griseofulvin, flucytosine (5-fc), miconazole, amphotericin B, ricin, cyclosporins, and β-lactam antibiotics (e.g., sulfazecin) |
| vitamins | cyanocobalamin neinoic acid, retinoids and derivatives such as retinol palmitate, and α-tocopherol |
| peptides | manganese super oxide dismutase; enzymes such as alkaline phosphatase |
| anti-allergic agents | Amelexanox |
| anti-coagulation agents | phenprocoumon and heparin |
| circulatory drugs | Propranolol |
| metabolic potentiators | Glutathione |
| antivirals | acyclovir, amantadine azidothymidine (AZT, DDI, Foscarnet, or Zidovudine), ribavirin and vidarabine monohydrate (adenine arabinoside, ara-A) |
| antianginals | diltiazem, nifedipine, verapamil, erythritol tetranitrate, isosorbide dinitrate, nitroglycerin (glyceryl trinitrate) and pentaerythritol tetranitrate |
| antibiotics | dapsone, chloramphenicol, neomycin, cefaclor, cefadroxil, cephalexin, cephradine erythromycin, clindamycin, lincomycin, amoxicillin, ampicillin, bacampicillin, carbenicillin, dicloxacillin, cyclacillin, picloxacillin, hetacillin, methicillin, nafcillin, oxacillin, penicillin including penicillin G and penicillin V, ticarcillin rifampin, aminoglycosides and tetracycline |
| antiinflammatories | diflunisal, ibuprofen, indomethacin, meclofenamate, mefenamic acid, naproxen, oxyphenbutazone, phenylbutazone, piroxicam, sulindac, tolmetin, aspirin and salicylates |

TABLE D-continued

| Non-limiting Examples of Therapeutic Agents | |
|---|---|
| Therapeutic Agent | Non-limiting examples |
| antirheumatics | Adalimumab, azathioprine, chloroquine and hydroxychloroquine (antimalarials), cyclosporine (Cyclosporin A), D-penicillamine, etanercept, gold salts (sodium aurothiomalate, auranofin), infliximab, leflunomide, methotrexate, minocycline (a tetracycline antibiotic), sulfasalazine |
| narcotics | Paregoric, opiates, codeine, heroin, methadone, morphine and opium |
| cardiac glycosides | deslanoside, digitoxin, digoxin, digitalin and digitalis |
| neuromuscular blockers | atracurium mesylate, gallamine triethiodide, hexafluorenium bromide, metocurine iodide, pancuronium bromide, succinylcholine chloride (suxamethonium chloride), tubocurarine chloride and vecuronium bromide |
| sedatives (hypnotics) | amobarbital, amobarbital sodium, aprobarbital, butabarbital sodium, chloral hydrate, ethchlorvynol, ethinamate, flurazepam hydrochloride, glutethimide, methotrimeprazine hydrochloride, methyprylon, midazolam hydrochloride, paraldehyde, pentobarbital, pentobarbital sodium, phenobarbital sodium, secobarbital sodium, talbutal, temazepam and triazolam |
| local anesthetics | bupivacaine hydrochloride, chloroprocaine hydrochloride, etidocaine hydrochloride, lidocaine hydrochloride, mepivacaine hydrochloride, procaine hydrochloride and tetracaine hydrochloride |
| general anesthetics | droperidol, etomidate, fentanyl citrate with droperidol, ketamine hydrochloride, methohexital sodium and thiopental sodium |
| radioactive particles or ions | strontium, iodide rhenium, yttrium, and radiopharmaceuticals, such as radioactive iodine, copper and phosphorus product |

II. Method of Use

In another aspect, an isolated antibody of the present invention, as described above, may be used in treating and preventing cancer and associated diseases in a subject. The antibodies of the present invention may be conjugated to radioisotopes or chemotherapeutic compounds in order to provide specific delivery of radiation and chemotherapy to the site of a tumor. Further, the antibodies of the present invention may be part of a combination therapy. Preferably, a combination therapy would include the use of the antibody of the present invention along with a radiation therapy or chemotherapy course of treatment. It has also been suggested that monoclonal antibodies, such as those described herein, may increase the susceptibility of tumor cells to the effects of chemotherapy or radiation. In preferred embodiments, the antibodies of the invention may be used to enhance the efficacy of cancer radiotherapy.

In yet another aspect, the present invention provides a method of imaging a cancer. As such, an antibody of the invention may be conjugated to an imaging agent. For instance, an scFv may be conjugated to an imaging agent. Suitable imaging agents may include, but are not limited to, imaging/tracking agents that may be used for microscopy, e.g. fluorescent microscopy, confocal microscopy, or electron microscopy, magnetic resonance imaging, tomography, such as gamma (SPECT/CT, planar) and positron emission tomography (PET/CT), radiography, or ultrasound. Imaging/tracking agents may be detectable in situ, in vivo, ex vivo, and in vitro. In general, imaging/tracking agents may include luminescent molecules, chemiluminescent molecules, fluorochromes, fluorescent quenching agents, colored molecules, radioisotopes, scintillants, massive labels (for detection via mass changes), biotin, avidin, streptavidin, protein A, protein G, antibodies or fragments thereof, Grb2, polyhistidine, Ni2+, Flag tags, myc tags, heavy metals, enzymes, alkaline phosphatase, peroxidase, luciferase, electron donors/acceptors, acridinium esters, and colorimetric substrates. The skilled artisan would readily recognize other useful labels that are not mentioned above, which may be employed in the operation of the present invention.

The antibodies are as described in Section I above. The subject, the cancer, and the administration of the antibodies are described below.

(a) Subject

A method of the invention may be used to detect or treat a tumor in a subject that is a human, a livestock animal, a companion animal, a lab animal, or a zoological animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In yet another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In preferred embodiments, the animal is a laboratory animal. Non-limiting examples of a laboratory animal may include rodents, canines, felines, and non-human primates. In certain embodiments, the animal is a rodent. Non-limiting examples of rodents may include mice, rats, guinea pigs, etc. The genotype of the sterile animal can and may vary depending on the intended use of the animal. In embodiments where the animal is a mouse, the mouse may be a C57BL/6 mouse, a Balb/c mouse, a 129sv mouse, a GL261 tumor bearing mouse, a D54 tumor bearing mouse, or any other laboratory strain.

(b) Tumor

An antibody of the invention may be used to treat or recognize tumor derived from a neoplasm or a cancer. The neoplasm may be malignant or benign, the cancer may be primary or metastatic; the neoplasm or cancer may be early stage or late stage. Non-limiting examples of neoplasms or cancers that may be treated include acute lymphoblastic leukemia, acute myeloid leukemia, adrenocortical carcinoma, AIDS-related cancers, AIDS-related lymphoma, anal cancer, appendix cancer, astrocytomas (childhood cerebellar or cerebral), basal cell carcinoma, bile duct cancer, bladder cancer, bone cancer, brainstem glioma, brain tumors (cerebellar astrocytoma, cerebral astrocytoma/malignant glioma, ependymoma, medulloblastoma, supratentorial primitive neuroectodermal tumors, visual pathway and hypothalamic gliomas), breast cancer, bronchial adenomas/carcinoids, Burkitt lymphoma, carcinoid tumors (childhood, gastrointestinal), carcinoma of unknown primary, central nervous system lymphoma (primary), cerebellar astrocytoma, cerebral astrocytoma/malignant glioma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma in the Ewing family of tumors, extracranial germ cell tumor (childhood), extragonadal germ cell tumor, extrahepatic bile duct cancer, eye cancers (intraocular melanoma, retinoblastoma), gallbladder cancer, gastric (stomach) cancer, gastrointestinal carcinoid tumor, gastrointestinal stromal tumor, germ cell tumors (childhood extracranial, extragonadal, ovarian), gestational trophoblastic tumor, gliomas (adult, childhood brain stem, childhood cerebral astrocytoma, childhood visual pathway and hypothalamic), gastric carcinoid, hairy cell leukemia, head and neck cancer, hepatocellular (liver) cancer, Hodgkin lymphoma, hypopharyngeal cancer, hypothalamic and visual pathway glioma (childhood), intraocular melanoma, islet cell carcinoma, Kaposi sarcoma, kidney cancer (renal cell cancer), laryngeal cancer, leukemias (acute lymphoblastic, acute myeloid, chronic lymphocytic, chronic myelogenous, hairy cell), lip and oral cavity cancer, liver cancer (primary), lung cancers (non-small cell, small cell), lymphomas (AIDS-related, Burkitt, cutaneous T-cell, Hodgkin, non-Hodgkin, primary central nervous system), macroglobulinemia (Waldenström), malignant fibrous histiocytoma of bone/osteosarcoma, medulloblastoma (childhood), melanoma, intraocular melanoma, Merkel cell carcinoma, mesotheliomas (adult malignant, childhood), metastatic squamous neck cancer with occult primary, mouth cancer, multiple endocrine neoplasia syndrome (childhood), multiple myeloma/plasma cell neoplasm, mycosis fungoides, myelodysplastic syndromes, myelodysplastic/myeloproliferative diseases, myelogenous leukemia (chronic), myeloid leukemias (adult acute, childhood acute), multiple myeloma, myeloproliferative disorders (chronic), nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer (surface epithelial-stromal tumor), ovarian germ cell tumor, ovarian low malignant potential tumor, pancreatic cancer, pancreatic cancer (islet cell), paranasal sinus and nasal cavity cancer, parathyroid cancer, penile cancer, pharyngeal cancer, pheochromocytoma, pineal astrocytoma, pineal germinoma, pineoblastoma and supratentorial primitive neuroectodermal tumors (childhood), pituitary adenoma, plasma cell neoplasia, pleuropulmonary blastoma, primary central nervous system lymphoma, prostate cancer, rectal cancer, renal cell carcinoma (kidney cancer), renal pelvis and ureter transitional cell cancer, retinoblastoma, rhabdomyosarcoma (childhood), salivary gland cancer, sarcoma (Ewing family of tumors, Kaposi, soft tissue, uterine), Sezary syndrome, skin cancers (nonmelanoma, melanoma), skin carcinoma (Merkel cell), small cell lung cancer, small intestine cancer, soft tissue sarcoma, squamous cell carcinoma, squamous neck cancer with occult primary (metastatic), stomach cancer, supratentorial primitive neuroectodermal tumor (childhood), T-Cell lymphoma (cutaneous), testicular cancer, throat cancer, thymoma (childhood), thymoma and thymic carcinoma, thyroid cancer, thyroid cancer (childhood), transitional cell cancer of the renal pelvis and ureter, trophoblastic tumor (gestational), unknown primary site (adult, childhood), ureter and renal pelvis transitional cell cancer, urethral cancer, uterine cancer (endometrial), uterine sarcoma, vaginal cancer, visual pathway and hypothalamic glioma (childhood), vulvar cancer, Waldenström macroglobulinemia, and Wilms tumor (childhood). In preferred embodiments, the neoplasm or cancer is non-small cell lung carcinoma.

(c) administration

In certain aspects, a pharmacologically effective amount of an antibody of the invention, including immunologically reactive fragments, may be administered to a subject. Administration is performed using standard effective techniques, including peripherally (i.e. not by administration into the central nervous system) or locally to the central nervous system. Peripheral administration includes but is not limited to intravenous, intraperitoneal, subcutaneous, pulmonary, transdermal, intramuscular, intranasal, buccal, sublingual, or suppository administration. Local administration, including directly into the central nervous system (CNS) includes but is not limited to via a lumbar, intraventricular or intraparenchymal catheter or using a surgically implanted controlled release formulation.

Pharmaceutical compositions for effective administration are deliberately designed to be appropriate for the selected mode of administration, and pharmaceutically acceptable excipients such as compatible dispersing agents, buffers, surfactants, preservatives, solubilizing agents, isotonicity agents, stabilizing agents and the like are used as appropriate. Remington's Pharmaceutical Sciences, Mack Publishing Co., Easton Pa., 16Ed ISBN: 0-912734-04-3, latest edition, incorporated herein by reference in its entirety, provides a compendium of formulation techniques as are generally known to practitioners. It may be particularly useful to alter the solubility characteristics of the antibodies useful in this discovery, making them more lipophilic, for example, by encapsulating them in liposomes or by blocking polar groups.

Effective peripheral systemic delivery by intravenous or intraperitoneal or subcutaneous injection is a preferred method of administration to a living patient. Suitable vehicles for such injections are straightforward. In addition, however, administration may also be effected through the mucosal membranes by means of nasal aerosols or suppositories. Suitable formulations for such modes of administration are well known and typically include surfactants that facilitate cross-membrane transfer. Such surfactants are often derived from steroids or are cationic lipids, such as N-[1-(2,3-dioleoyl)propyl]-N,N,N-trimethyl ammonium chloride (DOTMA) or various compounds such as cholesterol hemisuccinate, phosphatidyl glycerols and the like.

The concentration of antibody in formulations to be administered is an effective amount and ranges from as low as about 0.1% by weight to as much as about 15 or about 20% by weight and will be selected primarily based on fluid volumes, viscosities, and so forth, in accordance with the particular mode of administration selected if desired. A typical composition for injection to a living patient could be made up to contain 1 mL sterile buffered water of phosphate buffered saline and about 1-1000 mg of any one of or a combination of the humanized antibody of the present discovery. The formulation could be sterile filtered after making the formulation, or otherwise made microbiologically acceptable. A typical composition for intravenous infusion could have volumes between 1-250 mL of fluid, such as sterile Ringer's solution, and 1-100 mg per ml, or more in anti-GRP78 or anti-TIP-1 antibody concentration. Therapeutic agents of the discovery can be frozen or lyophilized for storage and reconstituted in a suitable sterile carrier prior to use. Lyophilization and reconstitution may lead to varying degrees of antibody activity loss (e.g. with conventional immune globulins, IgM antibodies tend to have greater activity loss than IgG antibodies). Dosages administered are effective dosages and may have to be adjusted to compensate. The pH of the formulations generally pharmaceutical grade quality, will be selected to balance antibody stability (chemical and physical) and comfort to the patient when administered. Generally, a pH between 4 and 8 is tolerated. Doses will vary from individual to individual based on size, weight, and other physiobiological characteristics of the individual receiving the successful administration.

As used herein, the term "effective amount" means an amount of a substance such as a compound that leads to measurable and beneficial effects for the subject administered the substance, i.e., significant efficacy. The effective amount or dose of compound administered according to this discovery will be determined by the circumstances surrounding the case, including the compound administered, the route of administration, the status of the symptoms being treated and similar patient and administration situation considerations among other considerations.

In some embodiments, when the antibody is an anti-TIP-1 antibody labeled with $^{64}$Cu, the dose administered may be about 0.01, 0.02, 0.03, 0.04, 0.05 0.06, 0.07, 0.08, 0.09, 0.1, 0.011, 0.012, 0.013, 0.013, 0.014, 0.015, 0.016, 0.017, 0.018, 0.019, 0.02, 0.021, 0.022, 0.023, 0.023, 0.024, 0.025, 0.026, 0.027, 0.028, 0.029, 0.03, 0.031, 0.032, 0.033, 0.033, 0.034, 0.035, 0.036, 0.037, 0.038, 0.039, 0.04, 0.041, 0.042, 0.043, 0.043, 0.044, 0.045, 0.046, 0.047, 0.048, 0.049, 0.05, 0.051, 0.052, 0.053, 0.053, 0.054, 0.055, 0.056, 0.057, 0.058, 0.059, 0.06, 0.061, 0.062, 0.063, 0.063, 0.064, 0.065, 0.066, 0.067, 0.068, 0.069, 0.07, 0.071, 0.072, 0.073, 0.073, 0.074, 0.075, 0.076, 0.077, 0.078, 0.079, 0.08, 0.081, 0.082, 0.083, 0.083, 0.084, 0.085, 0.086, 0.087, 0.088, 0.089, 0.09, 0.091, 0.092, 0.093, 0.093, 0.094, 0.095, 0.096, 0.097, 0.098, 0.099, or about 0.1 rem/mCi.

In some embodiments, when the antibody is an anti-GRP78 labeled with $^{64}$Cu, the dose administered may be about 0.01, 0.02, 0.03, 0.04, 0.05 0.06, 0.07, 0.08, 0.09, 0.1, 0.011, 0.012, 0.013, 0.013, 0.014, 0.015, 0.016, 0.017, 0.018, 0.019, 0.02, 0.021, 0.022, 0.023, 0.023, 0.024, 0.025, 0.026, 0.027, 0.028, 0.029, 0.03, 0.031, 0.032, 0.033, 0.033, 0.034, 0.035, 0.036, 0.037, 0.038, 0.039, 0.04, 0.041, 0.042, 0.043, 0.043, 0.044, 0.045, 0.046, 0.047, 0.048, 0.049, 0.05, 0.051, 0.052, 0.053, 0.053, 0.054, 0.055, 0.056, 0.057, 0.058, 0.059, 0.06, 0.061, 0.062, 0.063, 0.063, 0.064, 0.065, 0.066, 0.067, 0.068, 0.069, 0.07, 0.071, 0.072, 0.073, 0.073, 0.074, 0.075, 0.076, 0.077, 0.078, 0.079, 0.08, 0.081, 0.082, 0.083, 0.083, 0.084, 0.085, 0.086, 0.087, 0.088, 0.089, 0.09, 0.091, 0.092, 0.093, 0.093, 0.094, 0.095, 0.096, 0.097, 0.098, 0.099, or about 0.1 rem/mCi.

The frequency of dosing may be daily or once, twice, three times or more per week or per month, as needed as to effectively treat the symptoms. The timing of administration of the treatment relative to the disease itself and duration of treatment will be determined by the circumstances surrounding the case. Treatment could begin immediately, such as at the site of the injury as administered by emergency medical personnel. Treatment could begin in a hospital or clinic itself, or at a later time after discharge from the hospital or after being seen in an outpatient clinic. Duration of treatment could range from a single dose administered on a one-time basis to a life-long course of therapeutic treatments.

Although the foregoing methods appear the most convenient and most appropriate and effective for administration of proteins such as antibodies, by suitable adaptation, other effective techniques for administration, such as intraventricular administration, transdermal administration and oral administration may be employed provided proper formulation is utilized herein.

In addition, it may be desirable to employ controlled release formulations using biodegradable films and matrices, or osmotic mini-pumps, or delivery systems based on dextran beads, alginate, or collagen.

Typical dosage levels can be determined and optimized using standard clinical techniques and will be dependent on the mode of administration.

DEFINITIONS

As used herein, "antibody" refers to an immunoglobulin derived molecule that specifically recognizes either GRP78 or TIP-1. An antibody of the invention may be a full length antibody (IgM, IgG, IgA, IgE) or may be an antibody fragment (Fab, F(ab')2, scFv). An antibody may be chimeric or may be humanized.

As used herein, "CDR" means "complementary determining region." CDRs may also be referred to as hypervariable regions.

As used herein, "light chain" is the small polypeptide subunit of the antibody. A typical antibody comprises two light chains and two heavy chains.

As used herein, the "heavy chain" is the large polypeptide subunit of the antibody. The heavy chain of an antibody contains a series of immunoglobulin domains, with at least one variable domain and at least one constant domain.

"Humanized", as used herein, refers to the process where monoclonal antibodies are produced using recombinant DNA to create constructs capable of expression in human cell culture. Any known techniques for producing these constructs will work for purposes of the present invention.

As used herein, "single chain variable fragments" or "scFv" or "scFvs", refer to fusion proteins of the variable regions of the heavy and light chains of immunoglobulins connected via a linker. In some embodiment, the linker is a peptide of about 10 to 25 amino acids.

A "therapeutic agent" for purposes of the present invention, refers to an agent that reduces tumor growth, any related cancer growth, or reduces the symptoms associated with cancerous cell growth. The therapeutic agent that is preferably conjugated to the antibody of the present invention is preferably a biologic, pharmaceutical or chemical agent. A non-limiting list of therapeutic agents that may be suitable for use in the present invention is described above.

As used herein, "imaging agent" refers to any agent that can be used to locate and produce an image of cancerous cell growth or tumors. A non-limiting list of imagining agents that may be suitable for use in the present invention is described above.

EXAMPLES

The following examples illustrate various iterations of the invention.

Materials and Methods

Tumor Model

GL261 murine glioma cancer cell line was purchased from American Type Culture Collection. D54 cells were similarly purchased commercially. Heterotopic tumor models were developed by s.c. inoculating cell suspensions ($6\times10^6$ cells) into nude or C57/B16 mice.

Near IR Imaging

Tumor-bearing mice were treated with anywhere from one to three once-daily doses of 3 Gy XRT or sham XRT (three per group) and injected with peptide or antibody 3 hours after the last XRT treatment. Mice were then injected with an antibody to 78-kDa glucose regulated protein (GRP78) conjugated with AlexaFluor750 and tumors were removed 7 days after labeled antibody injection; polyclonal serum IgG antibody was used as a control. Near IR images were taken using the IVIS imaging system with an ICG filter setting at various time points after the injection.

Anti-TIP-1 and Anti-GRP78 Monoclonal Antibody Production and Purification.

BALB/C mice were initially immunized with 50 mg of TIP-1 or GRP78 antigen mixed with equivalent amounts of Titermax adjuvant (CytRx Corporation) for each mouse. One month after initial immunization, mice were boosted with equivalent amounts of antigen without adjuvant two to three times at two week intervals. The mouse polyclonal antibody titer was evaluated by ELISA and Western blot methods. Mice exhibiting high immune response to either antigen were chosen as B cell donors. Spleens were removed and homogenized in RPMI 1640 culture medium free of serum and other additives. Spleen cells were combined with Sp2/O mouse myeloma ($2\times10^7$ per spleen). Mixed cells were washed twice and centrifuged at 1200 rpm for 8 minutes at room temperature. Supernatant was removed, and the cell pellet was lightly agitated to loosen the cells. Approximately 1 ml PEG (polyethylene glycol 1500) (Roche) was added to fuse the cells. The fused cells were washed once with plain medium and finally re-suspended in RPMI 1640 medium supplemented with 10% fetal bovine serum (Gemini Bioproducts, CA), L-glutamine, antibiotics and HAT (Sigma), plated into 24 well tissue culture plates and incubated at 37° C. in a humidified $CO_2$ incubator. Fifteen days after fusion, hybridoma culture supernatants were removed from individual wells and transferred to separate 96 well microtiter plates for ELISA, Western blot and antibody printing assays against TIP-1 antigen. Hybridomas that produced antibodies positive by immunoassay were chosen for sub-cloning by using limiting dilution. Resulting single-cell clones were retested by the aforementioned methods to detect antigen-positive monoclonal antibody-producing hybridomas. Positive hybridoma clones were transferred to individual flasks to expand cell number from one cell clone, and incubated with serum-free medium for antibody production. The antibodies produced by positive clones in serum-free medium were harvested twice a week for further monoclonal antibody purification. Filtered monoclonal antibody collected from serum-free medium was purified by protein A and protein G columns. The concentrated purified monoclonal antibody was assayed and stored at −20° C.

Example 1

GRP78

Figure 2:
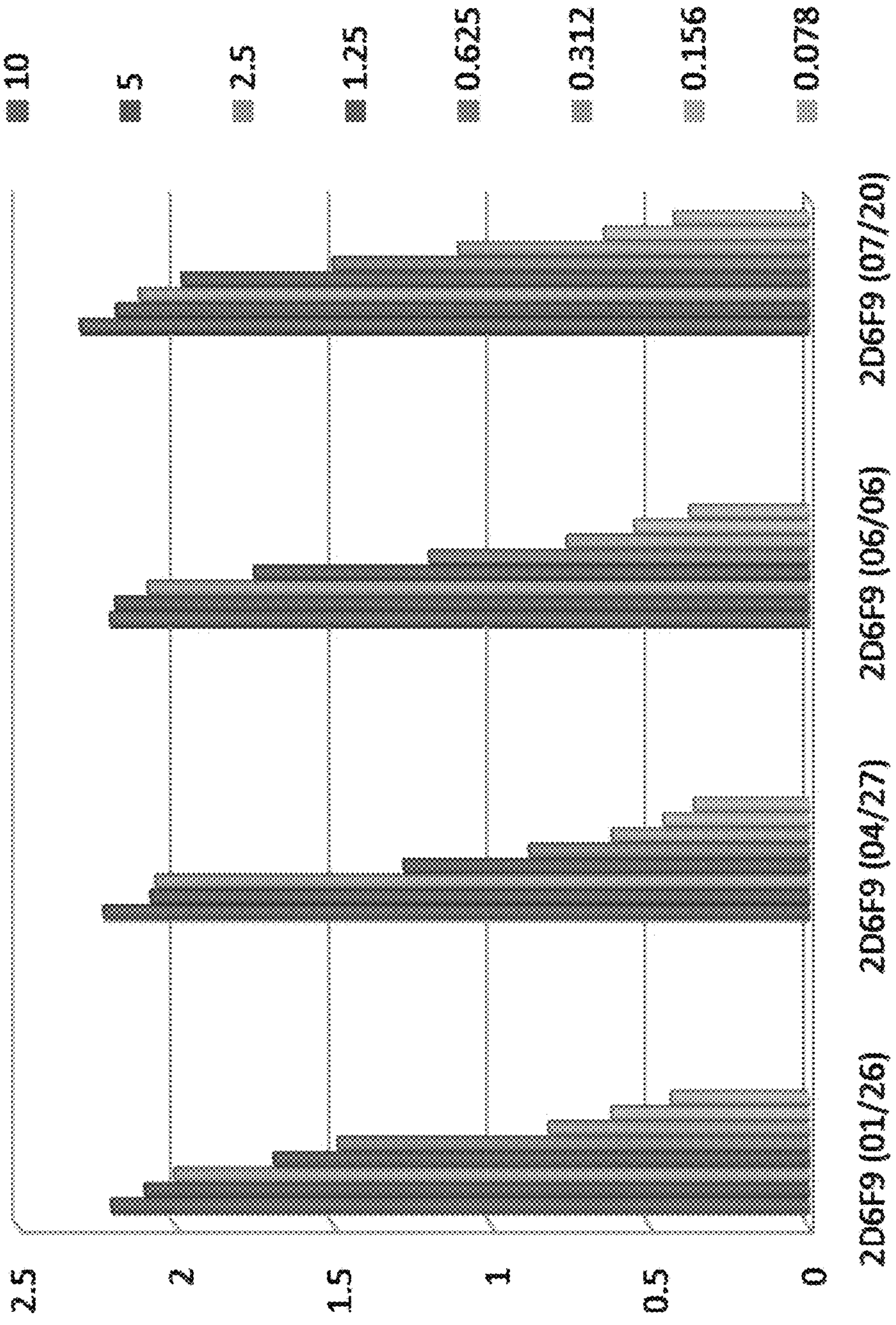
FIG. 2 depicts a graph showing the stability of the anti-GRP78 antibody 2B6F9. Antibody stocks stored at −20° C. and tested over six months are stable when tested by ELISA. Dilutions are shown on the right hand legend.

A monoclonal antibody against GRP78 was created, and named 2D6F9. The antibody comprised a heavy chain variable region amino acid sequence of SEQ ID NO:6 (minus the leader sequence) and a light chain variable region amino acid sequence of SEQ ID NO:8 (minus the leader sequence) (FIG. 7). As shown in FIG. 1, the antibody was an IgG1 isotype, and as shown in FIG. 2 was stable at −20° C. for at least six months. Epitope mapping was performed to determine that 2D6F9 recognized SEQ ID NO. 1, 2, 3, and 4 derived from human GRP78.

Figure 3A:
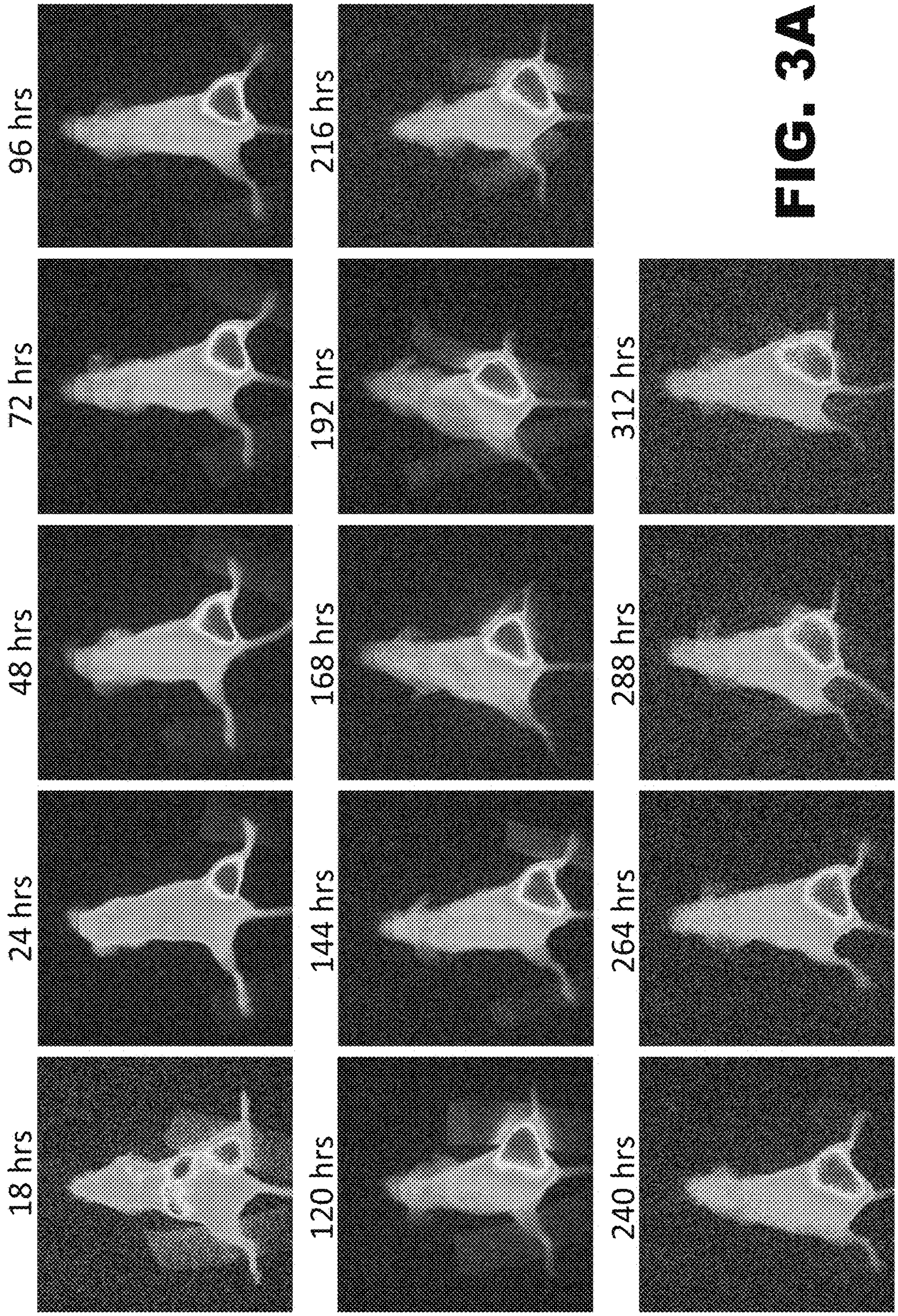
FIG. 3 depicts images of irradiated GL261 tumor bearing mice treated with anti-GRP78 antibody 2B6F9. (A), (B) and (C) represent three different mice with tumors on their right hind limbs and no tumors on their left hind limb. Each mouse was exposed to three separate 3Gy doses of radiation, separated by approximately 6 hours. Following radiation exposure, each mouse was administered antibody at 50 μg/mouse via i.v. Images were taken at 18, 24, 48, 72, 96, 120, 144, 168, 192, 216, 240, 264, 288, and 312 hours. The antiGRP78 antibody 2B6F9 was conjugated with Alexa Fluor 750, and the images show accumulation of the antibody at the site of tumor only.
Figure 3B:
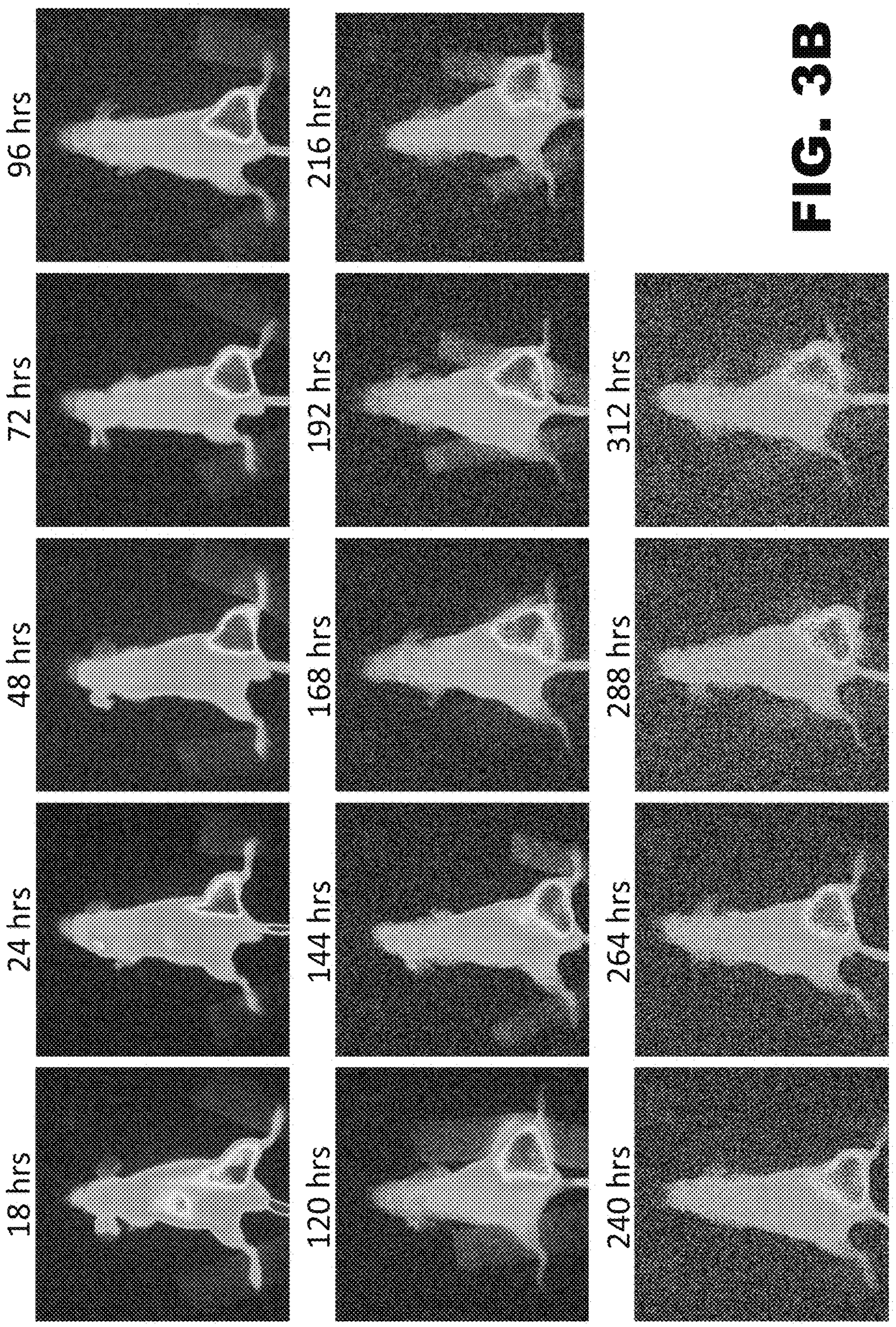
Figure 3C:
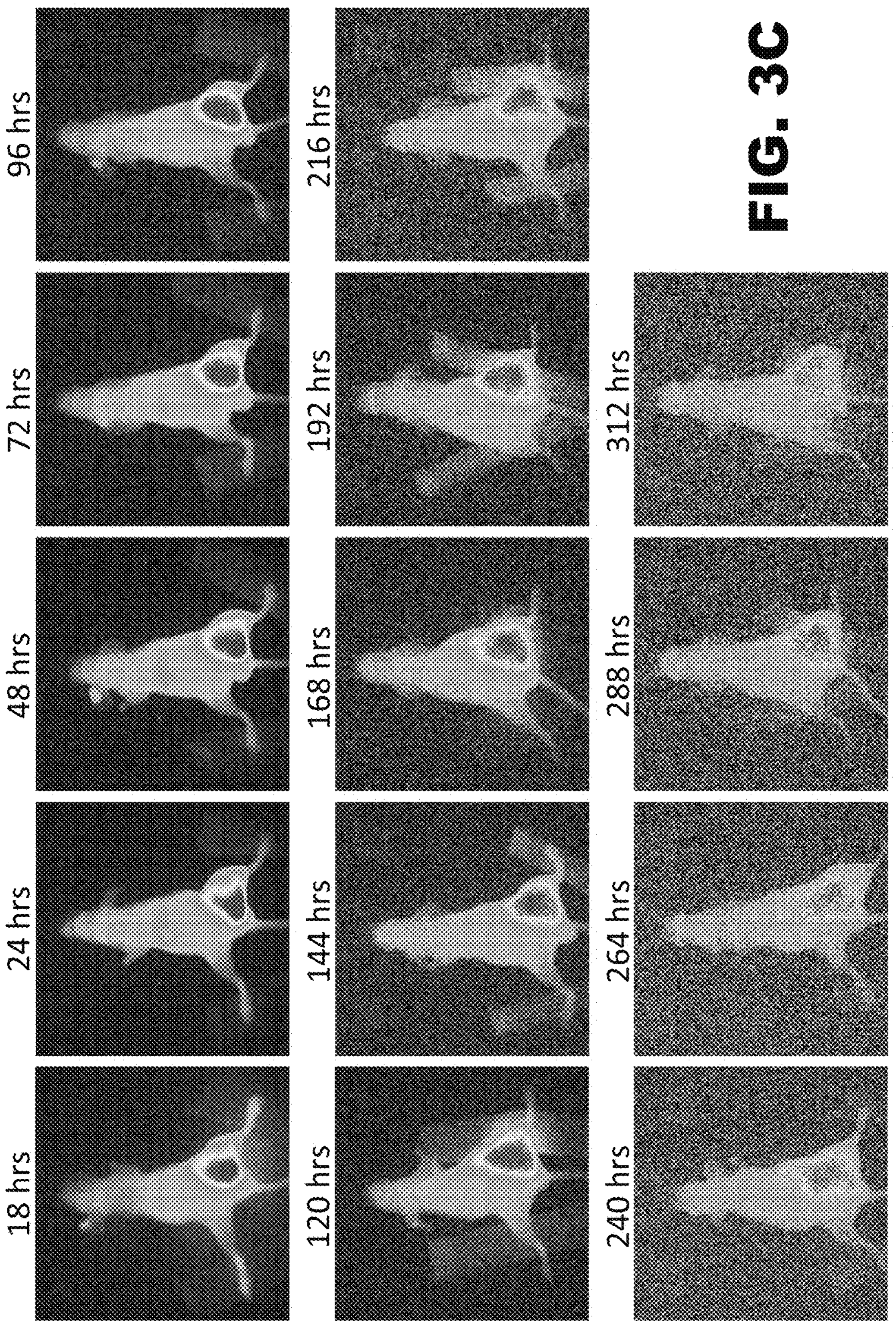
Figure 4:
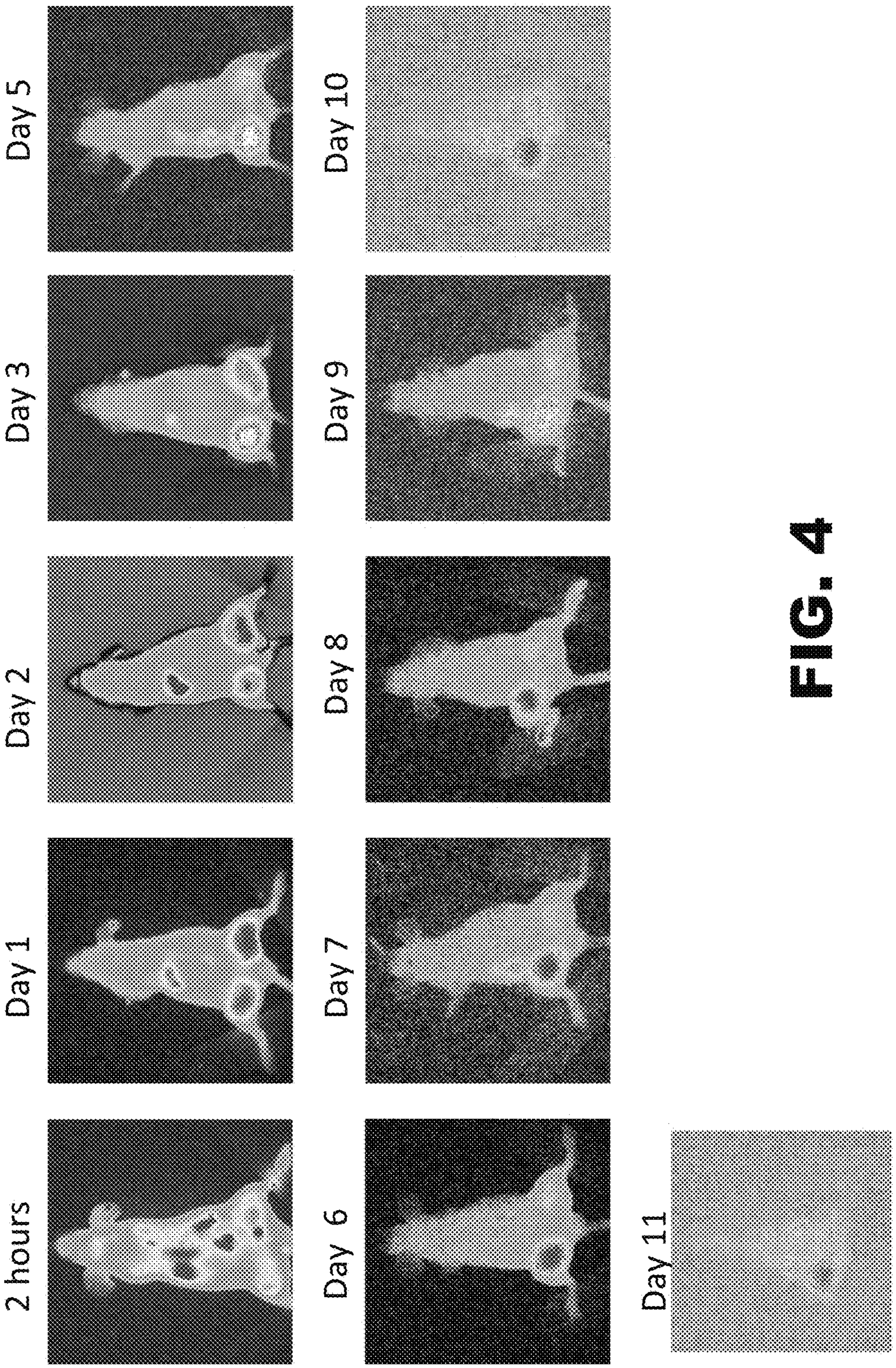
FIG. 4 depicts images of an irradiated GL261 tumor bearing mouse treated with anti-GRP78 antibody 2B6F9. The mouse was exposed to a single dose of 3Gy radiation on the hind left limb while there was no radiation exposure on the hind right limb. Following radiation exposure, each mouse was administered antibody at 50 μg/mouse via i.v. Images were taken at 2 hours and 1, 2, 3, 5, 6, 7, 8, 9, 10, and 11 days. The anti-GRP78 antibody 2B6F9 was conjugated with Alexa Fluor 750, and the images show accumulation of the antibody on the irradiated side.
Figure 5A:
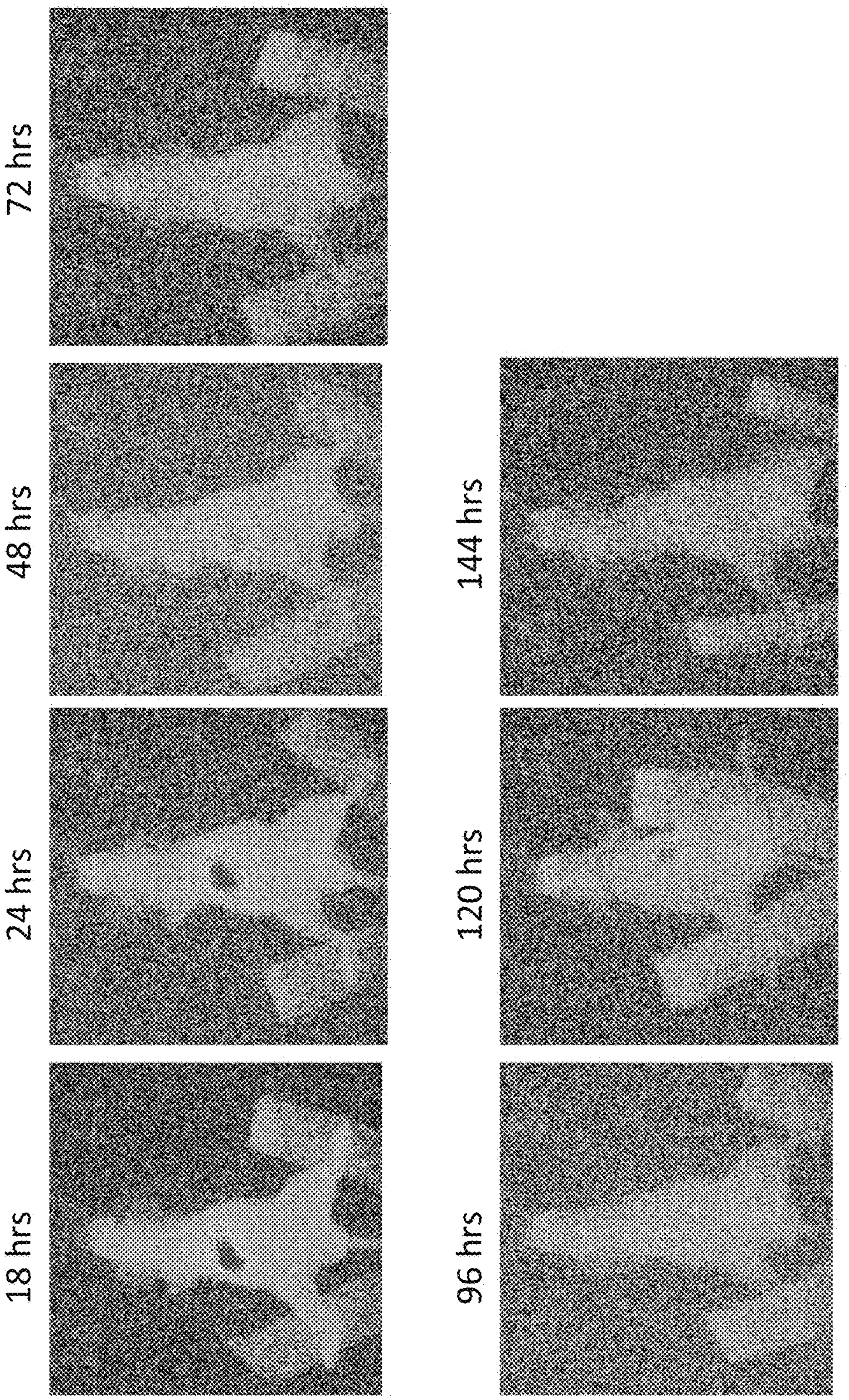
FIG. 5 depicts control images of GL261 tumor bearing mice treated with normal mouse IgG. (A) and (B) depict two different non-irradiated mice bearing tumors on the right hind limb. Each mouse was administered antibody at 50 μg/mouse via i.v. Images were taken at 18, 24, 48, 72, 96, 120, and 144 hours. The antiGRP78 antibody 2B6F9 was conjugated with Alexa Fluor 750, and the images show no accumulation of antibody. (C) and (D) depict two different irradiated mice bearing tumors on the right hind limb. Each mouse was exposed to a single dose of 3Gy radiation. Following exposure, each mouse was administered antibody at 50 μg/mouse via i.v. Images were taken at 18, 24, 48, 72, 96, 120, and 144 hours. The antiGRP78 antibody 2B6F9 was conjugated with Alexa Fluor 750, and the images show no accumulation of antibody. (E) depicts an irradiated mouse bearing tumors on the right hind limb. The mouse was exposed to three separate 3Gy doses of radiation, separated by approximately 6 hours. Following exposure, the mouse was administered antibody at 50 μg/mouse via i.v. Images were taken at 18, 24, 48, 72, 96, 120, 144, and 168 hours. The anti-GRP78 antibody 2B6F9 was conjugated with Alexa Fluor 750, and the images show no accumulation of antibody.
Figure 5B:
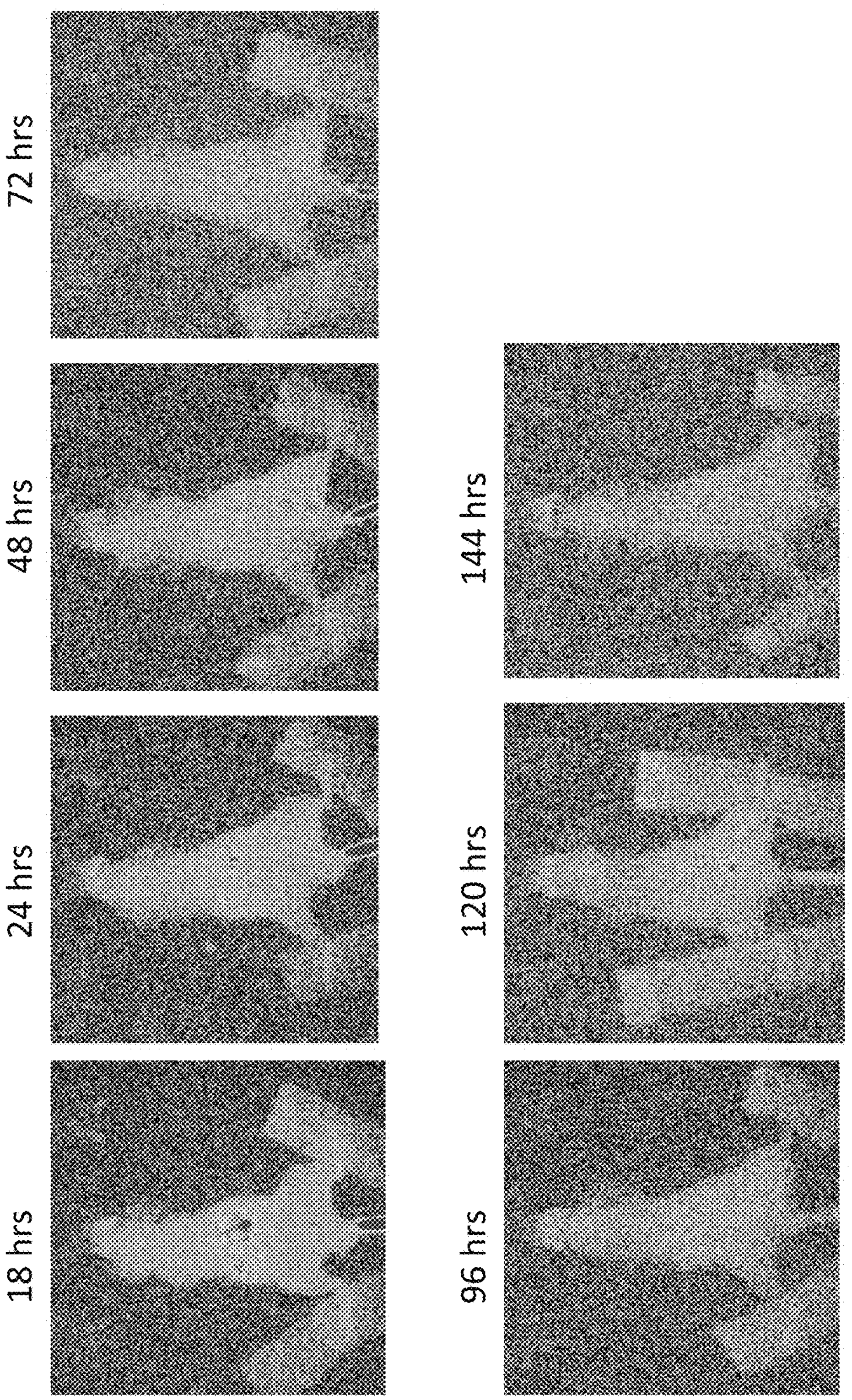
Figure 5C:
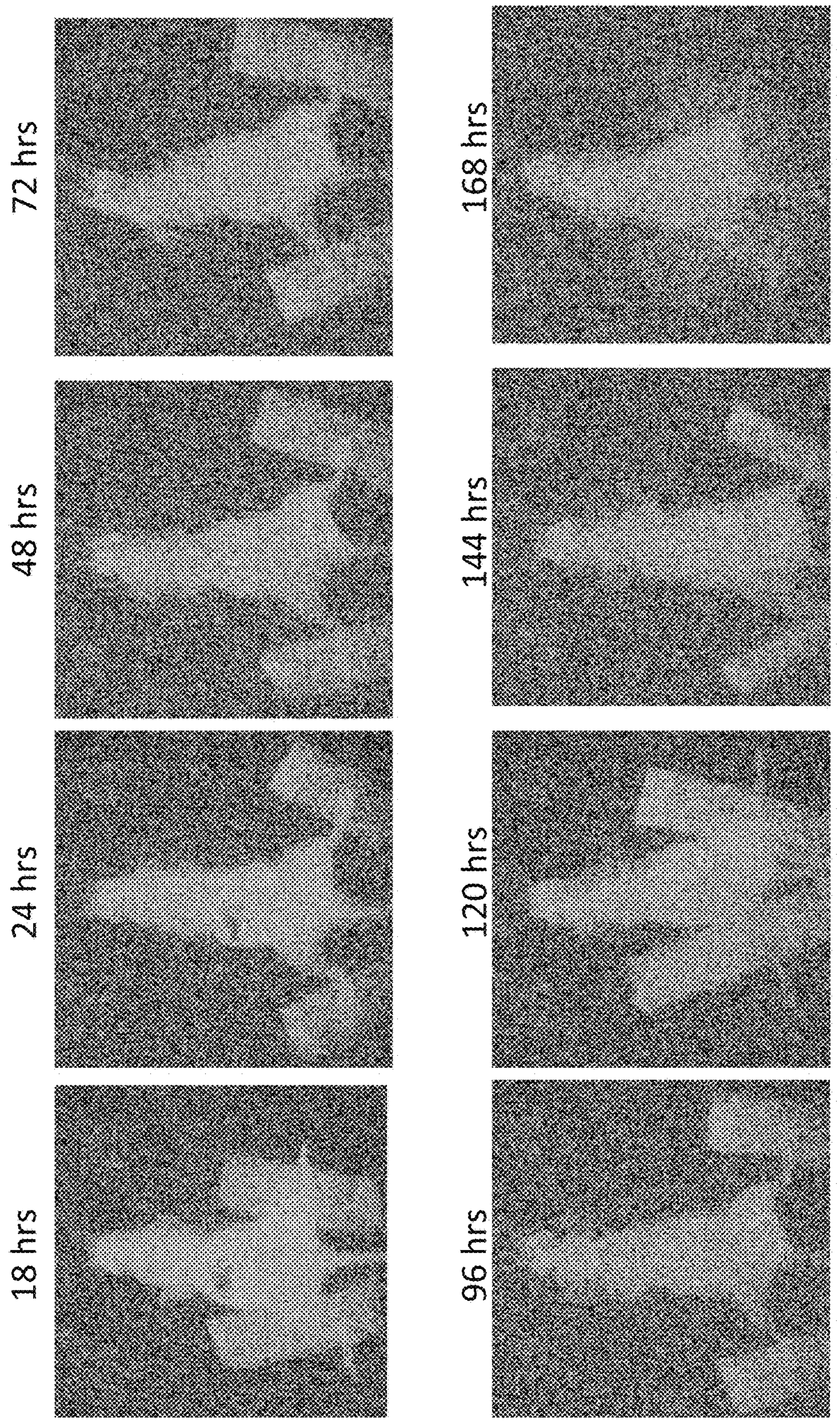
Figure 5D:
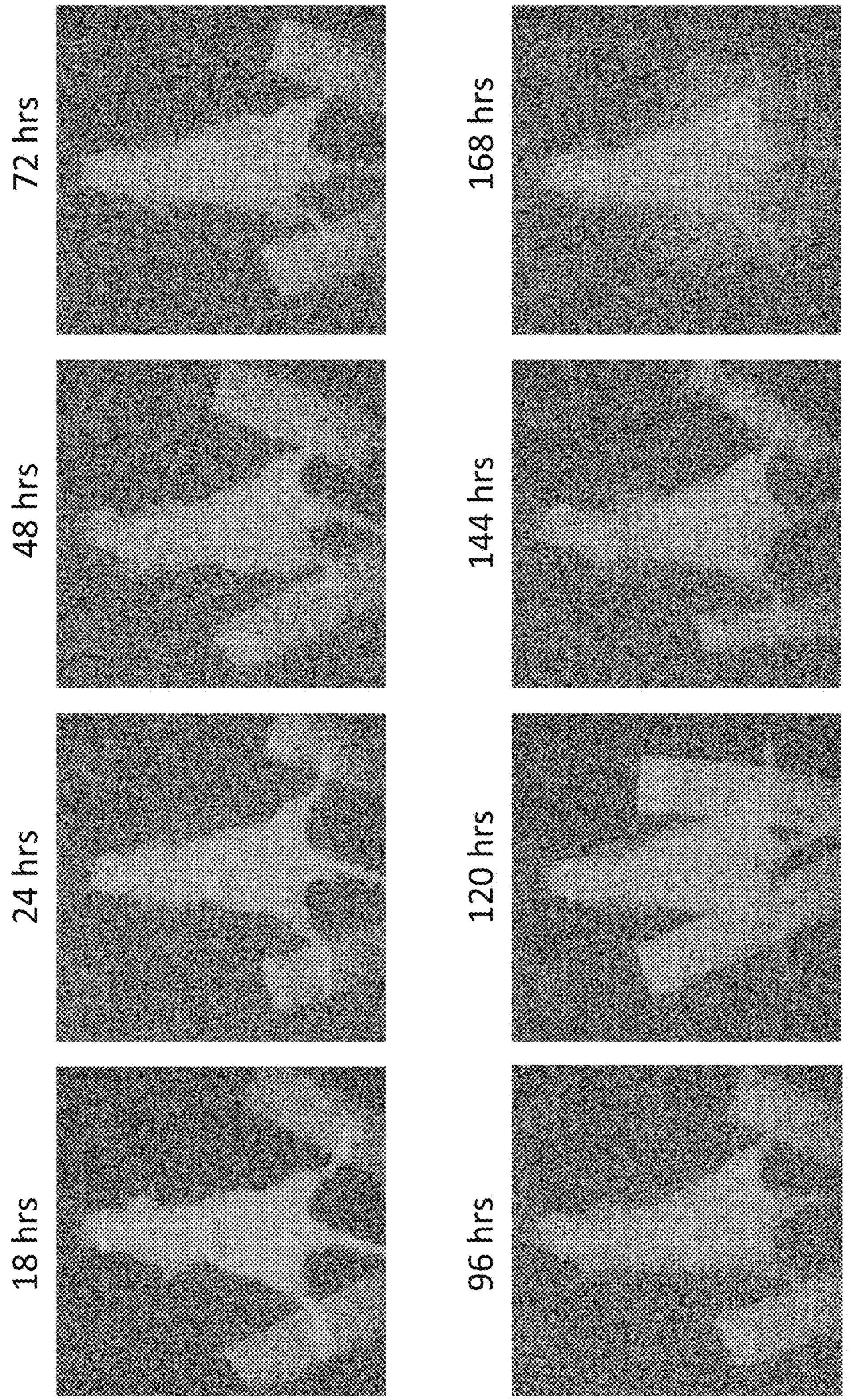
Figure 5E:
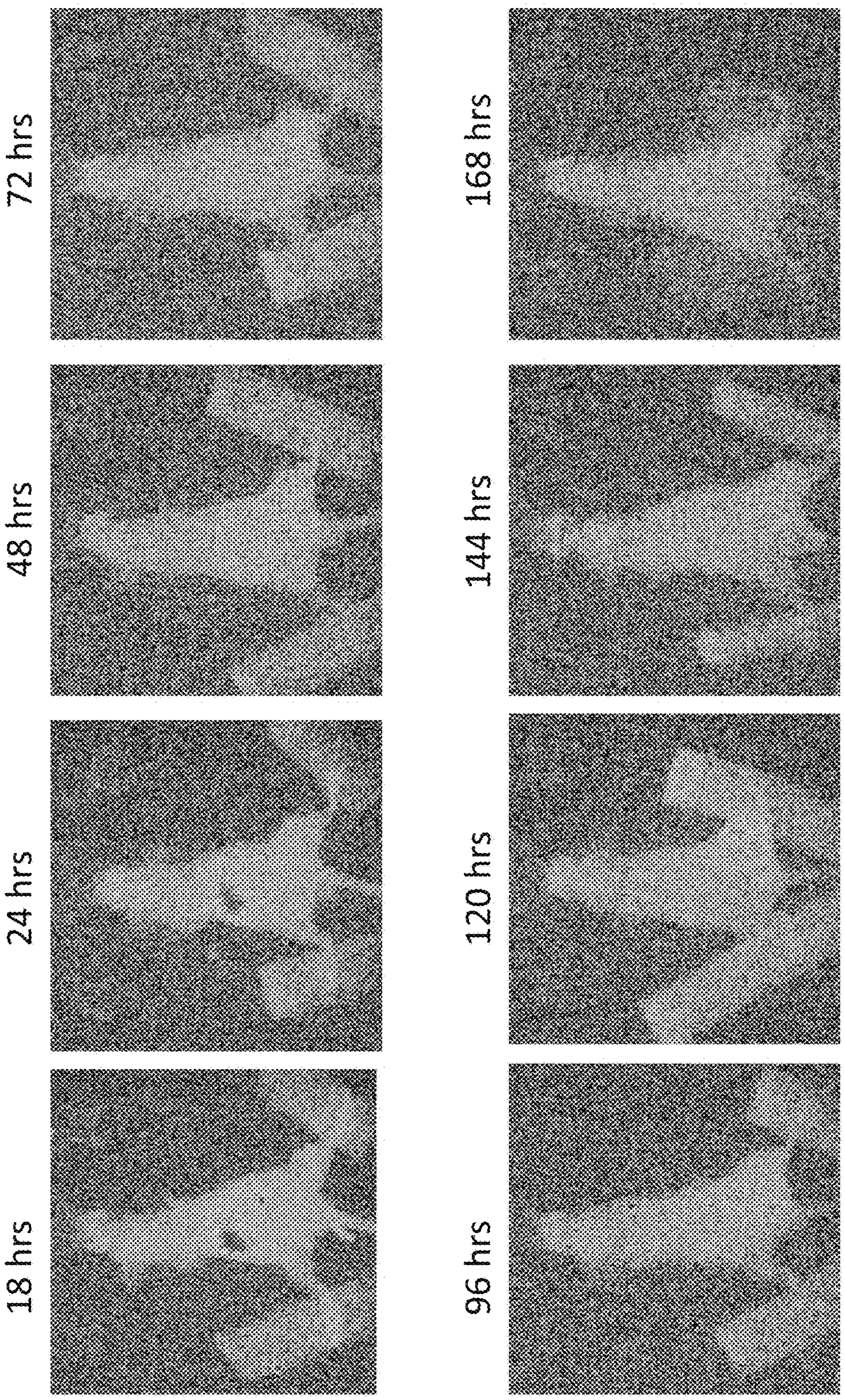
Figure 6A:
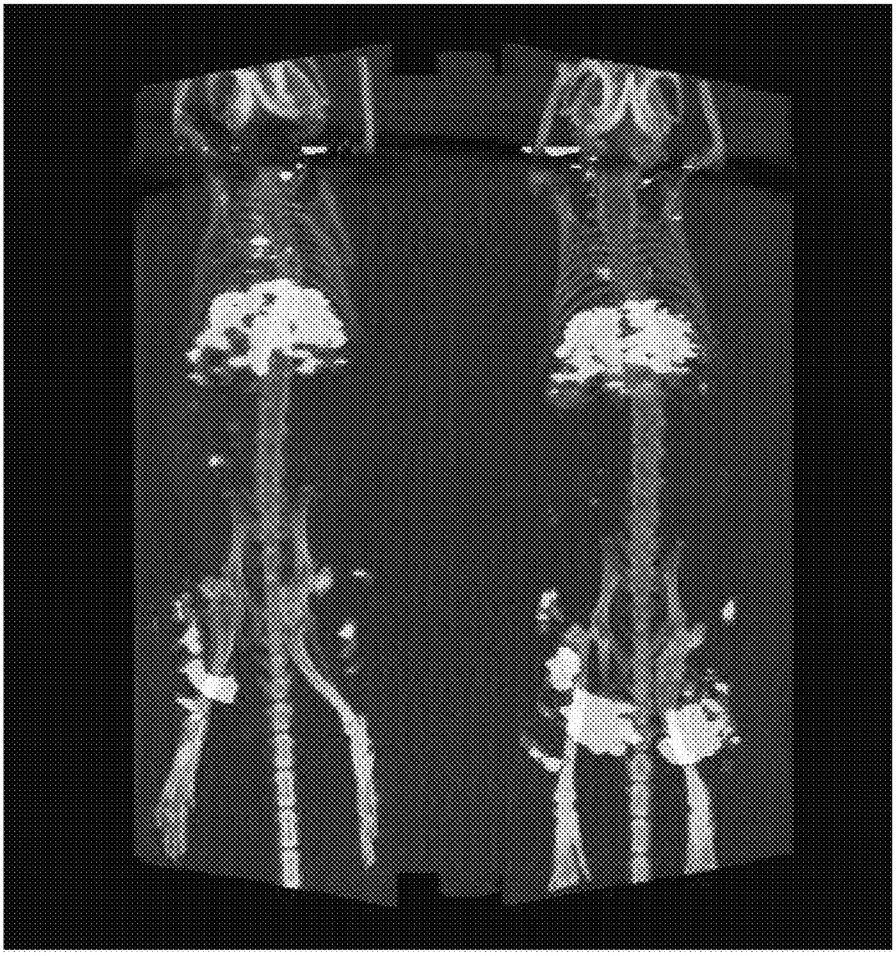
FIG. 6 depicts images and graphs showing distribution of $^{64}$Cu-anti-GRP78 antibody 2D6F9. (A) and (B) show different mice 24 hours after administration of 50 μg $^{64}$Cu-anti-GRP78 antibody 2D6F9. The left hindlimb was irradiated with 3Gy and the right hindlimb was not irradiated. (C) depicts mice 48 hours after administration of 50 μg $^{64}$Cu-anti-GRP78 antibody 2D6F9. The left hindlimb was irradiated with 3Gy and the right hindlimb was not irradiated. (D) depicts a graph showing the ex-vivo biodistribution of $^{64}$Cu-NOTA-anti-GRP78 2D6F9 antibody.
Figure 6B:
Figure 6C:
Figure 6D:
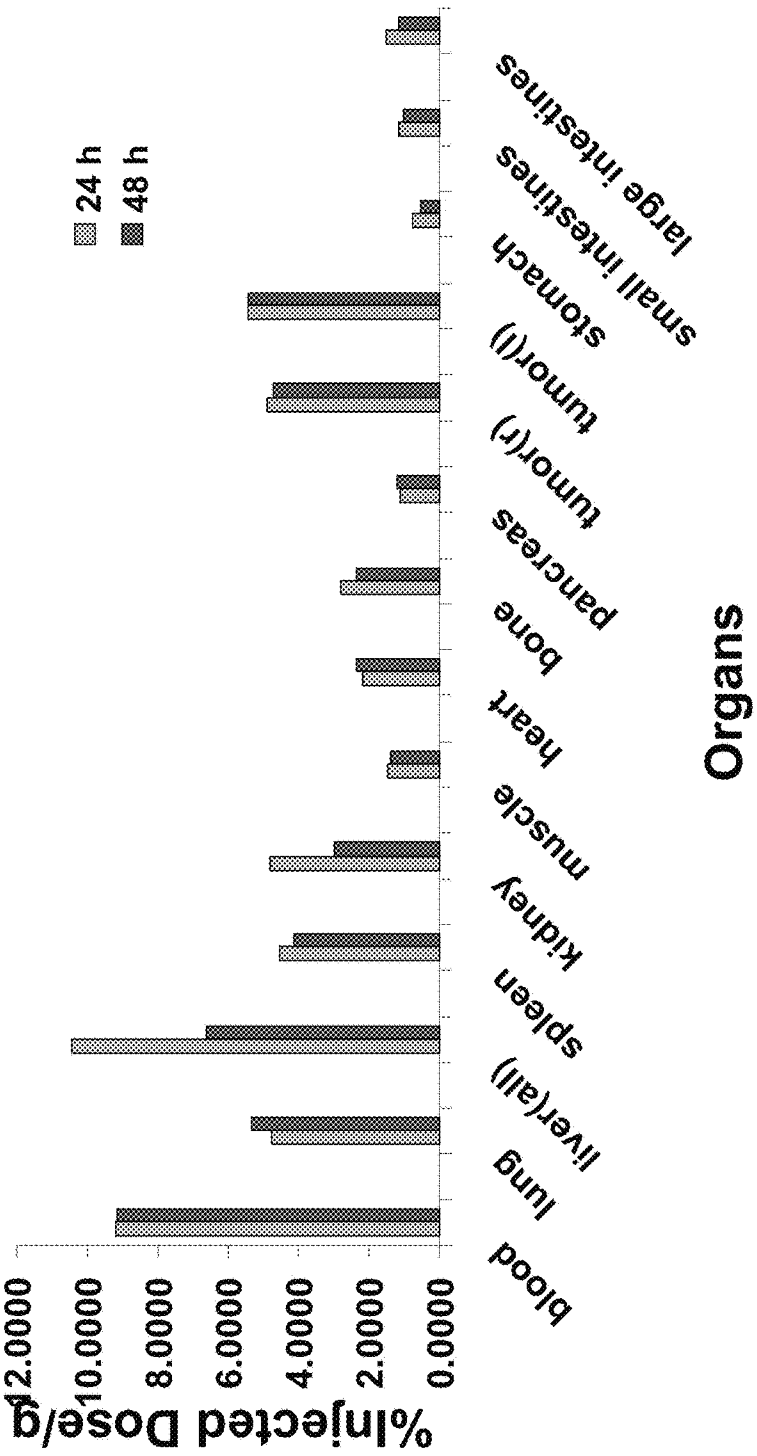
Figure 8:
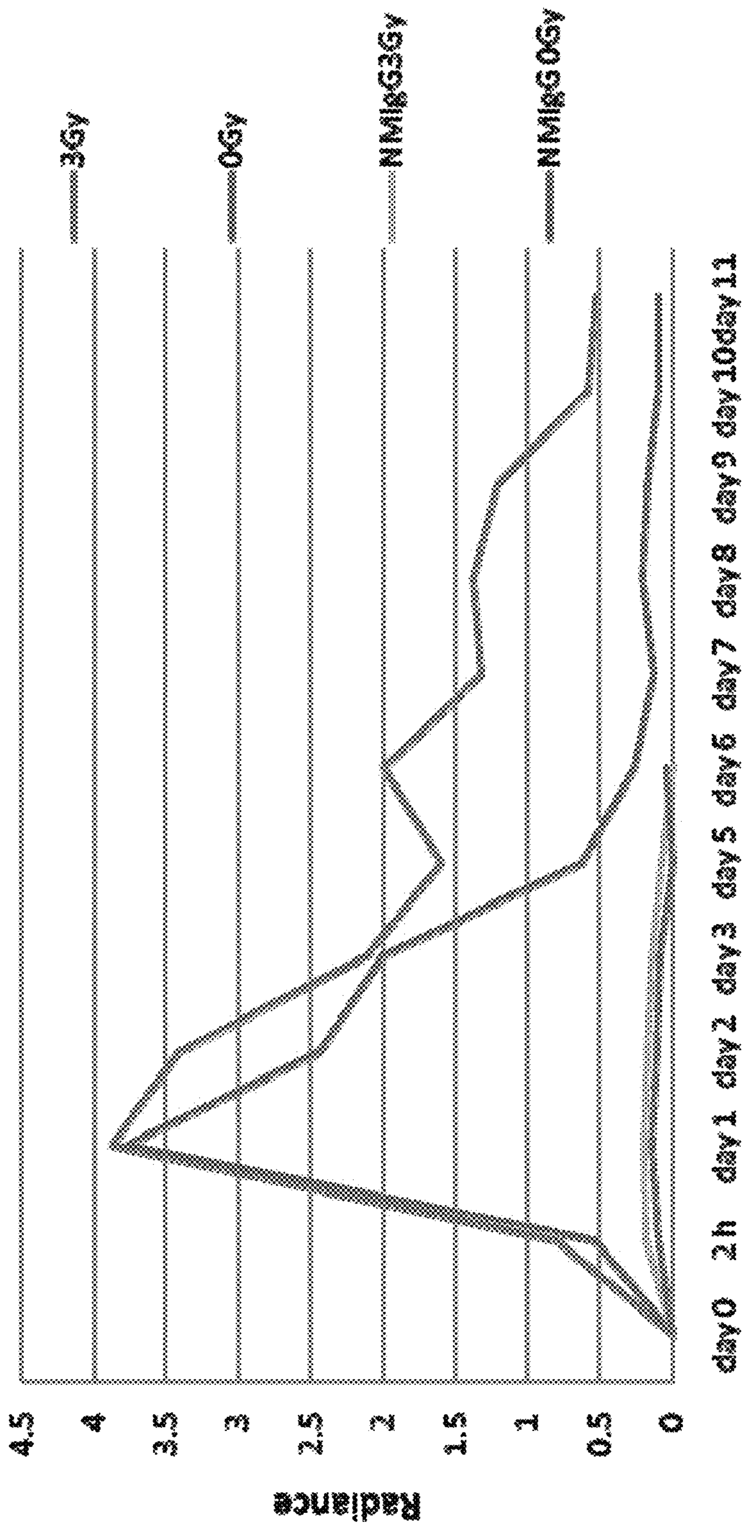
FIG. 8 depicts a graph showing the radiance emitted from the anti-GRP78 antibody 2B6F9 conjugated to Alexa Fluor 750 over time.
Figure 9A:
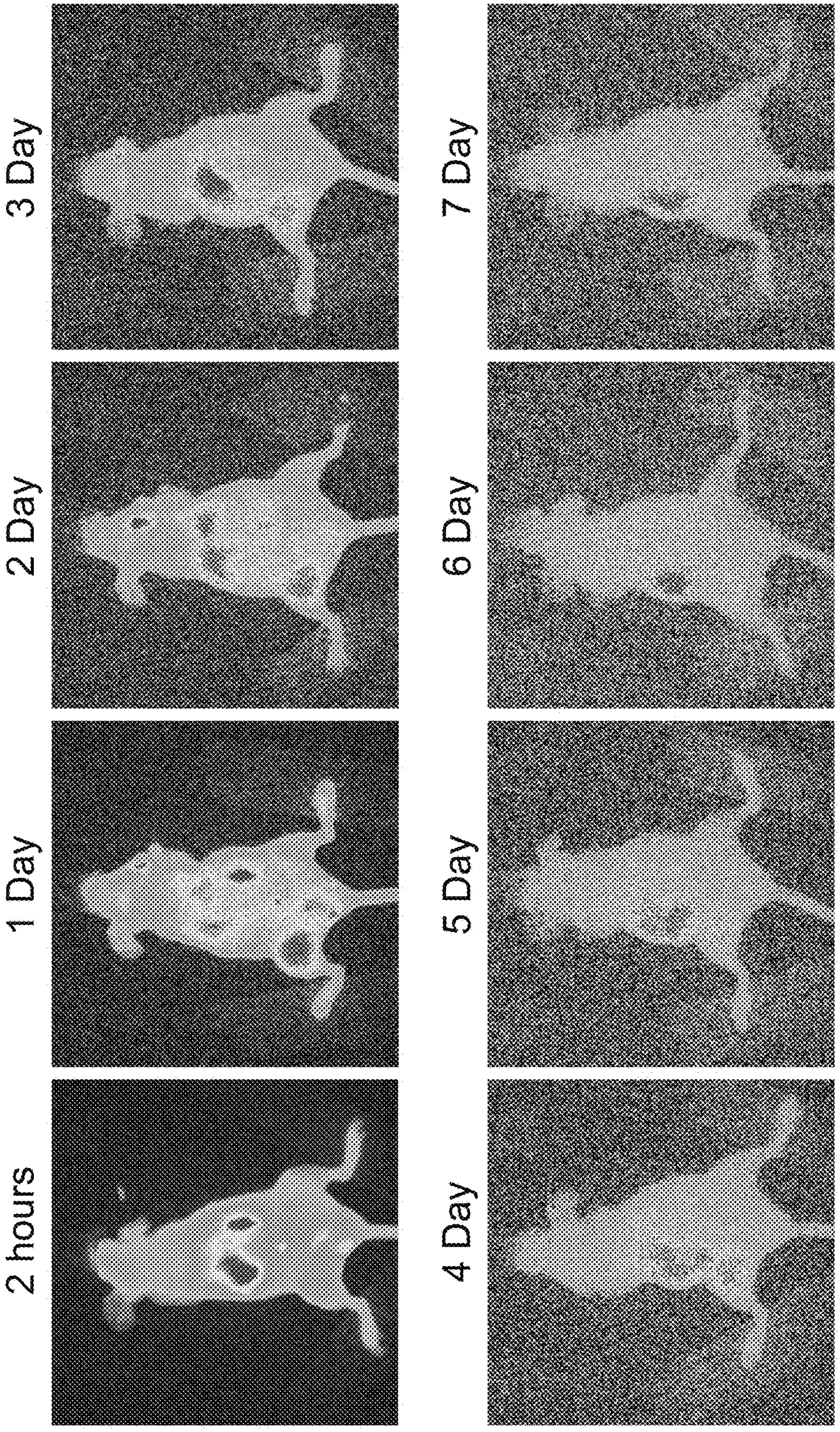
FIG. 9 depicts images of an irradiated D54 tumor bearing mouse treated with anti-GRP78 antibody 2B6F9. In (A) and (B) the mouse was exposed to a single dose of 3Gy radiation on the hind left limb while there was no radiation exposure on the hind right limb. Following radiation exposure, each mouse was administered antibody at 50 μg/mouse via i.v. Images were taken at 2 hours and 1, 2, 3, 4, 5, 6, and 7 days. The antiGRP78 antibody 2B6F9 was conjugated with Alexa Fluor 750.
Figure 9B:
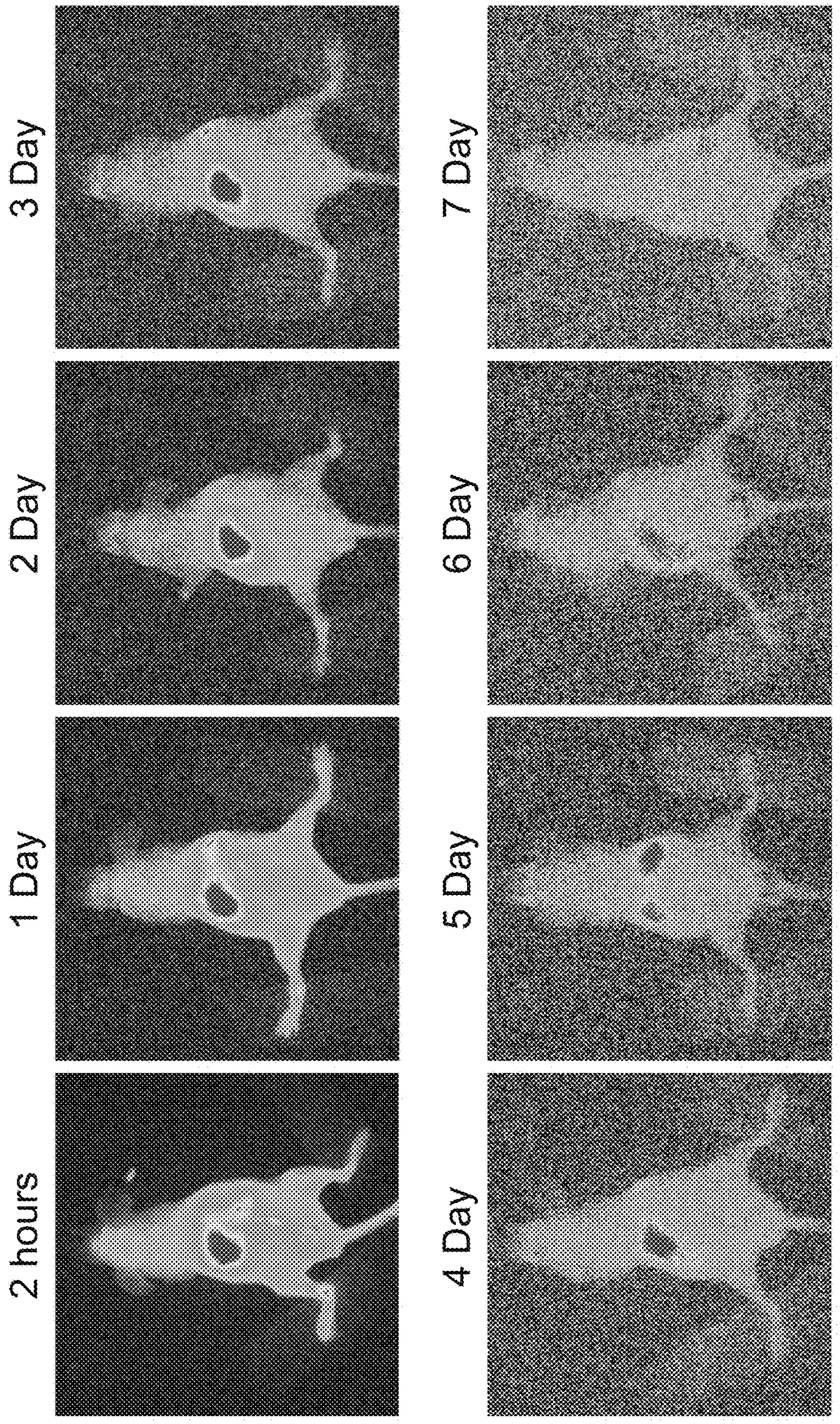

FIG. 8 depicts a graph showing the radiance emitted from the anti-GRP78 antibody 2B6F9 conjugated to Alexa Fluor 750 over time. The antibody 2D6F9 (conjugated to Alexa Fluor 750) recognized tumor cells from the GL261 tumor model that were exposed to either 3 separate 3Gy doses of radiation (FIG. 3) or a single dose of 3Gy radiation (FIG. 4), but did not recognize non-irradiated tumor tissue or normal tissue (either irradiated or non-irradiated). For comparison purposes a control non-specific IgG antibody was used in FIG. 5. Additionally, 2D6F9 (conjugated to Alexa Fluor 750) recognized tumor cells from the D54 tumor model that were exposed to a single dose of 3Gy radiation (FIG. 9), The distribution of $^{64}$Cu-anti-GRP78 antibody 2D6F9 was measured. Mice were administered 50 μg of $^{64}$Cu-anti-GRP78 antibody 2D6F9 and imaged at 24 (FIG. 6A,B) and 48 hours (FIG. 6C). The left hindlimb was irradiated with 3Gy and the right hindlimb was not irradiated. Animal biodistribution data was obtained. Animals were euthanized and organs were harvested at 24 and 48 hours post injection. The following organs were harvested, weighed and counted for radio-activity in a gamma counter: blood, lungs, liver, spleen, kidneys, muscle, heart, bone, pancreas, tumor (r), tumor (l), stomach, small intestines, and large intestines. The biodistribution data are presented in FIG. 6D.

Example 2

TIP-1

At least three monoclonal antibodies against TIP-1 were created, and named 1A6H14, 3A415, and 2C6F3. Epitope mapping was performed to determine that 1A6H14 recognized SEQ ID NO: 9, 10, and 11 derived from human TIP-1, that 3A415 recognized SEQ ID NO: 12, 13, and 14 derived from human TIP-1, and that 2C6F3 recognized SEQ ID NO:21 derived from human TIP-1 (see Table C).

Figure 24A:
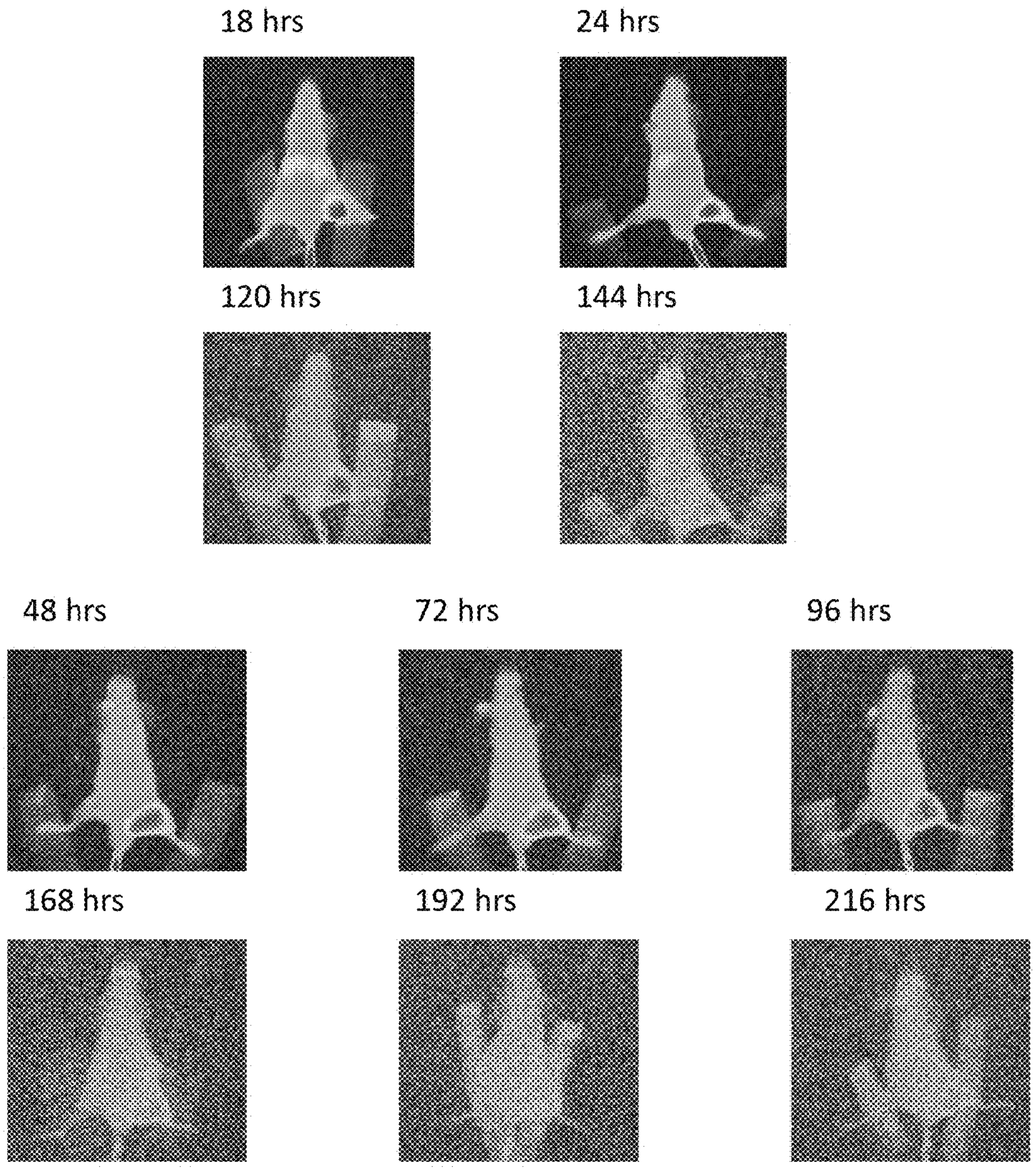
FIG. 24 depicts images of an irradiated GL261 tumor bearing mouse treated with anti-TIP-1 antibody 2C6F3. (A) shows mouse 1 and (B) shows mouse 2. Each mouse was exposed to three separate 3Gy doses of radiation, separated by approximately 6 hours, on the hind right limb while there was no radiation exposure on the hind left limb. Following radiation exposure, each mouse was administered antibody via i.v. Images were taken at 18, 24, 48, 72, 96, 120, 144, 168, 192 and 216 hours. The anti-TIP-1 antibody 2C6F3 was conjugated with Alexa Fluor 750, and the images show accumulation of the antibody on the irradiated side.
Figure 24B:
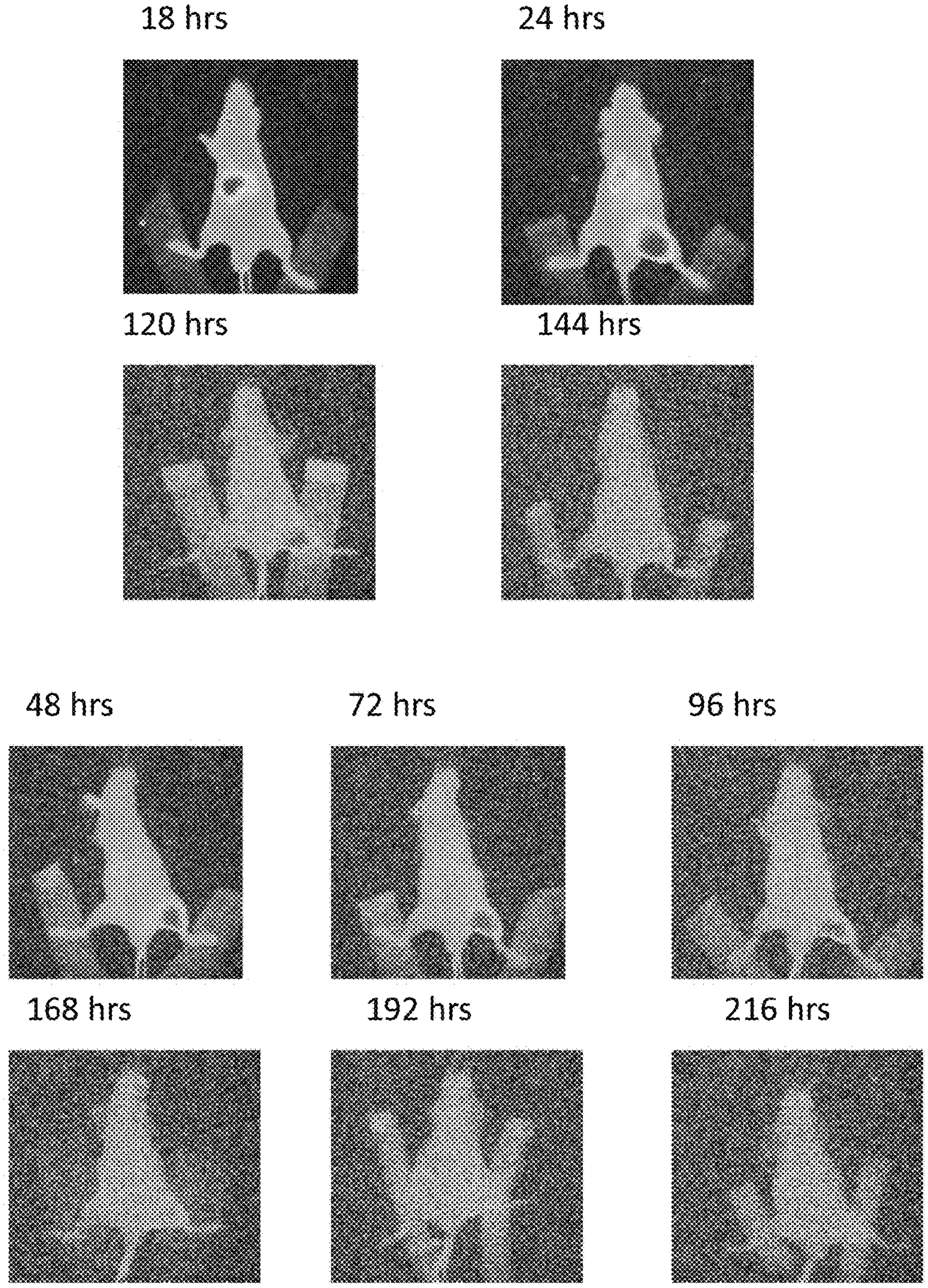

The antibodies were shown to recognize irradiated tumor cells compared to non-irradiated tumor tissue or normal tissue (either irradiated or non-irradiated). Specifically, anti-TIP-1 monoclonal antibody, 2C6F3, showed binding by flow cytometry to human glioblastoma D54 cells (WHO grade IV) (FIG. 23). 2C6F3 (conjugated to Alexa Fluor 750) recognized tumor cells from the GL261 tumor model that were exposed to radiation (FIG. 24), but did not recognize non-irradiated tumor tissue or normal tissue (either irradiated or non-irradiated).

Figure 25:
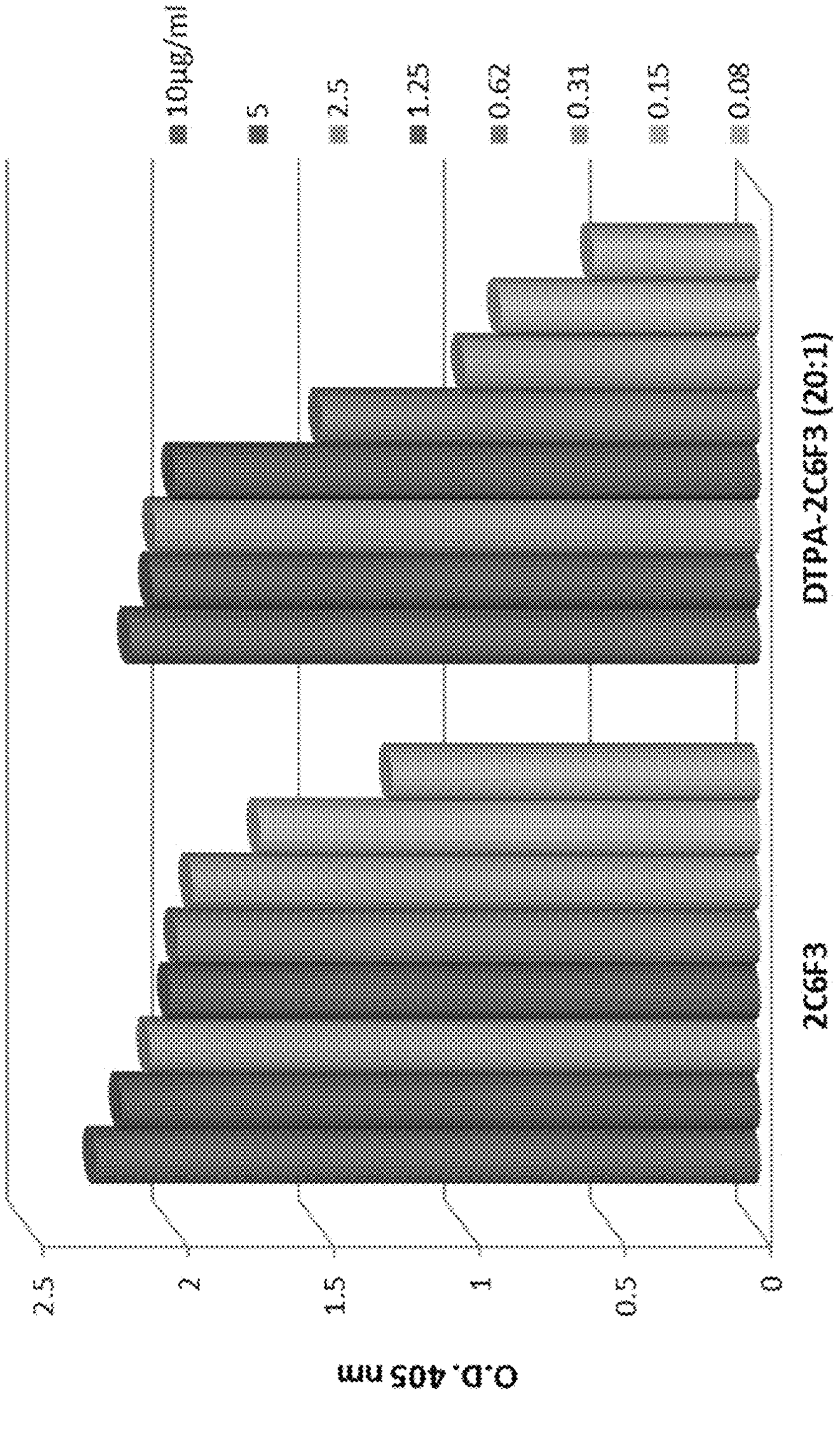
FIG. 25 depicts a graph showing labeling of DTPA chelator on antibody 2C6F3 tested by ELISA.
Figure 26A:
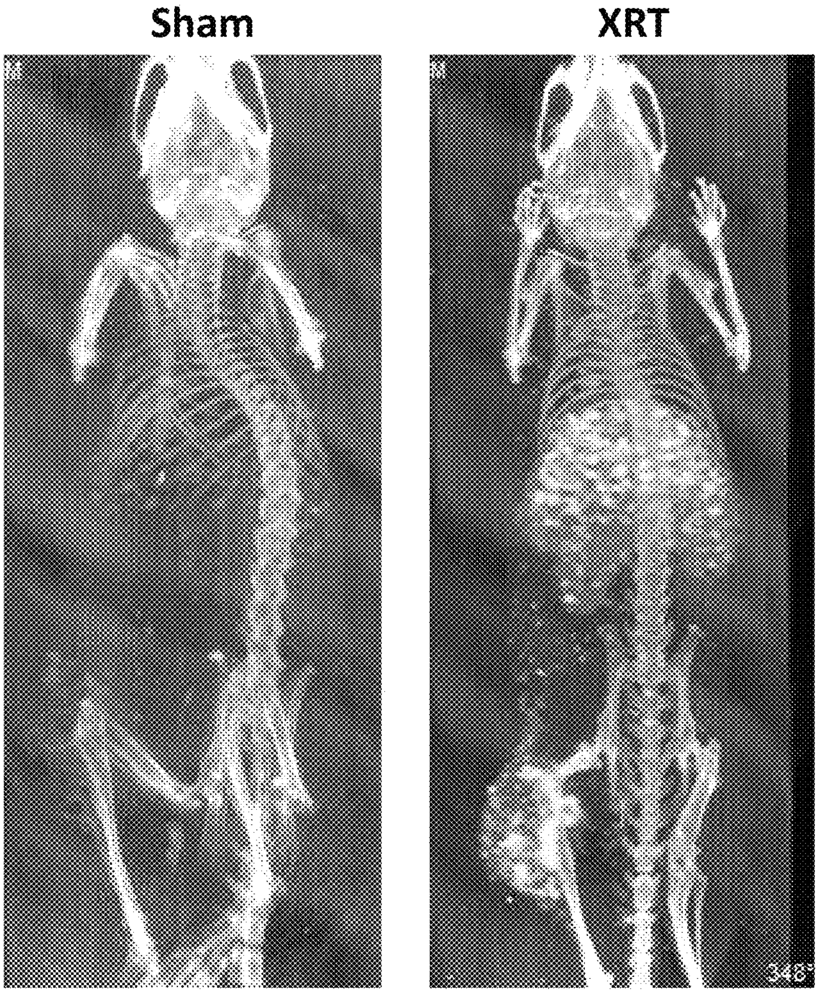
FIG. 26 depicts CT/SPECT images showing distribution of $^{111}$In-DTPA-2C6F3 in LLC tumor bearing mice. Mice were irradiated with 3Gy×3 over a 24 hour period or sham non-irradiated. Images are of three mice 48 hours after administration of $^{111}$In-DTPA-2C6F3. (A) shows mouse 1, (B) shows mouse 2, and (C) shows mouse 3.
Figure 26B:
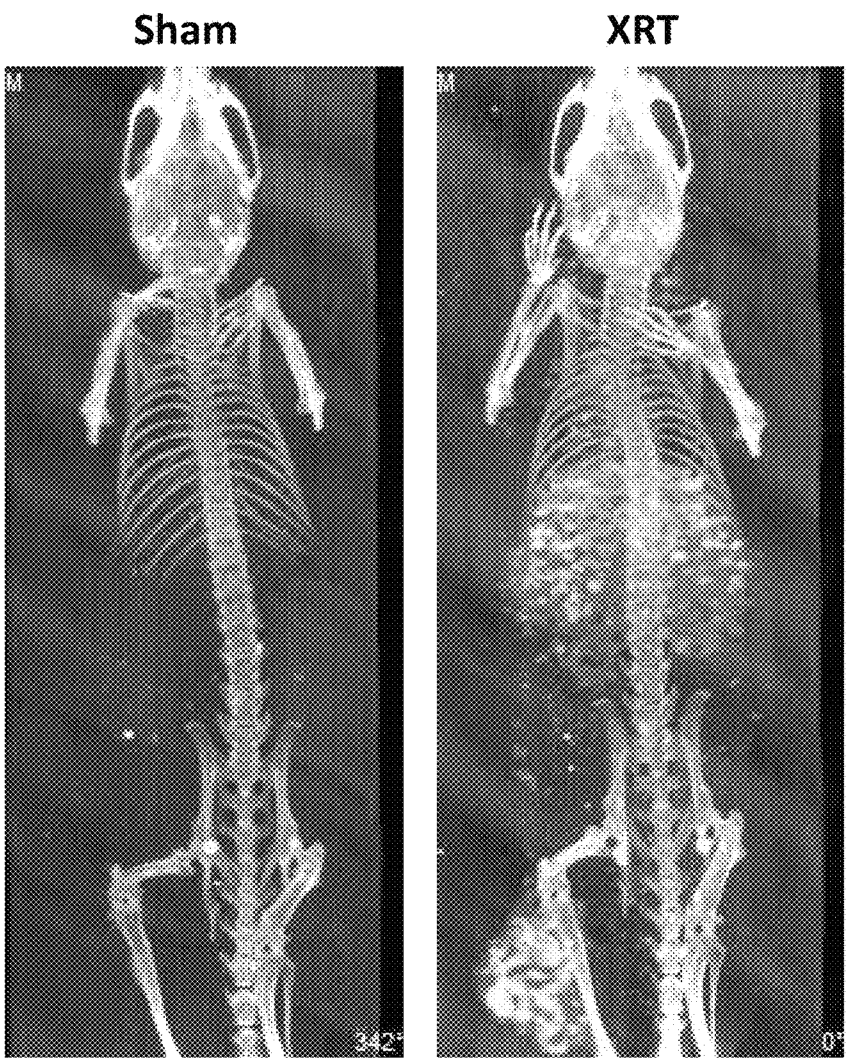
Figure 26C:
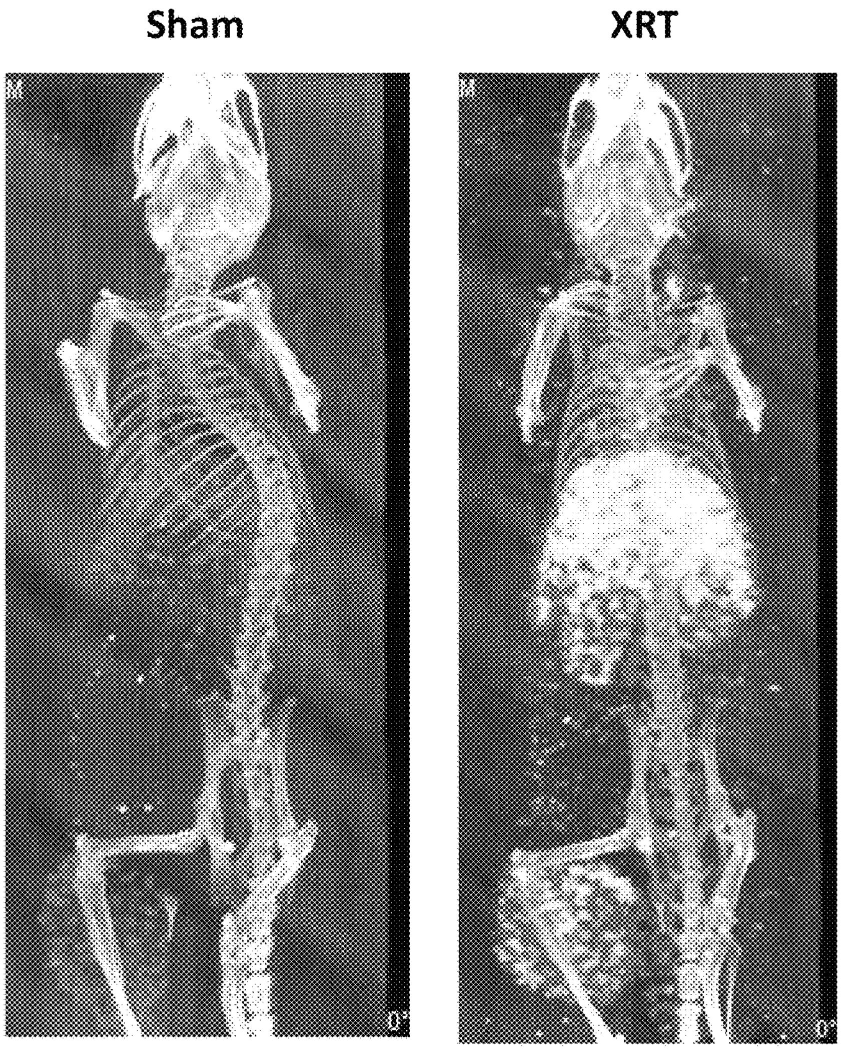
Figure 27A:
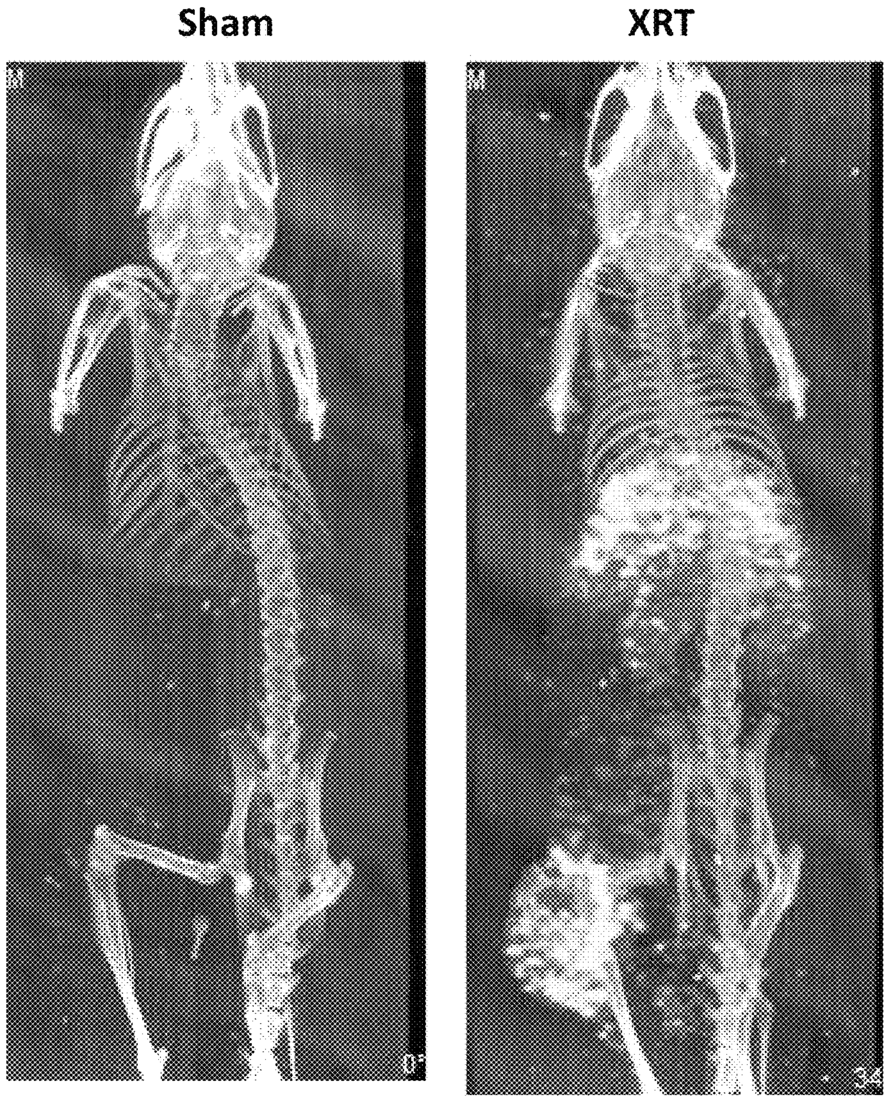
FIG. 27 depicts CT/SPECT images showing distribution of $^{111}$In-DTPA-2C6F3 in LLC tumor bearing mice. Mice were irradiated with 3Gy×3 over a 24 hour period or sham non-irradiated. Images are of three mice 78 hours after administration of $^{111}$In-DTPA-2C6F3. (A) shows mouse 1, (B) shows mouse 2, and (C) shows mouse 3.
Figure 27B:
Figure 27C:
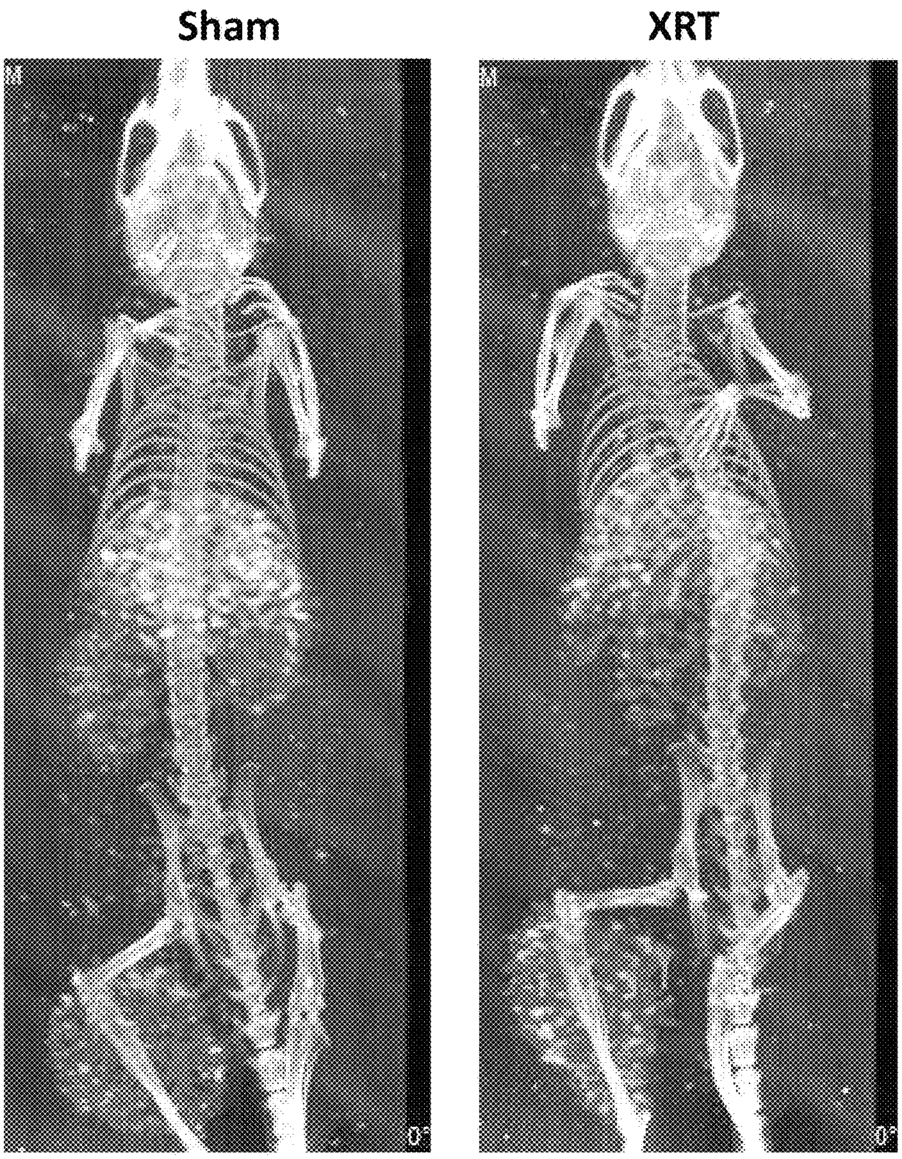

CT/SPECT imaging with $^{111}$In-DTPA was performed with the anti-TIP-1 2C6F3 monoclonal antibody. LLC (Lewis lung carcinoma) tumors were grown to approximately 1 $cm^3$ in C57/BL mice. Two groups of mice each containing 3 mice were utilized. Group 1 mice were irradiated with 3Gy×3 over 24 hours. Group 2 mice were sham non-irradiated. $^{111}$In was labeled with DTPA-2C6F3 TIP-1 antibody with a final specific activity of 0.7 μCi/μg. FIG. 25 shows the labeling of DTPA chelator on 2C6F3. Mice were subjected to tail vein injection of ~250 μCi in 150 μl volume for SPECT imaging. Mice were imaged using nano-SPECT scan at 48 hours (FIGS. 26) and 72 hours (FIG. 27) post IV injection. FIG. 26 and FIG. 27 show the distribution of $^{111}$In-DTPA-2C6F3 anti-TIP-1 antibody.

Example 3

Dosimetry of Labeled Anti-GRP78 2D6F9 Antibody

Biodistribution in Healthy Mice

Human radiation dosimetry estimates were calculated from animal biodistribution data obtained by standard method of organ dissection and using the standard MIRD methodology. Animal biodistribution data was obtained using 30 C57 mature male mice injected with 16 μCi/100 μL of $^{64}$Cu-DOTA-2D6F9 antibody divided in 6 groups of 5 animals. The average animal mouse weight was 25.0 g. Animals were euthanized and organs were harvested in groups of five at the following time points: 1, 2, 6, 12, 24 and 48 hours post injection. The following organs were harvested, weighed and counted for radio-activity in a gamma counter: blood, lungs, liver, spleen, kidneys, bladder, muscle, fat, heart, brain, bone, red marrow, testes, adrenals, thyroid, pancreas, stomach, small intestines, and upper and lower large intestines. The animals were maintained in metabolic cages where urine and feces excretion were collected, weighed and counted for radio-activity. The biodistribution data are presented in Table 1.

TABLE 1

Organ activity concentration from mice dissection expressed in percent injected per gram of tissue.

| Organ | 1 hr | 2 hr | 6 hr | 12 hr | 24 hr | 48 hr |
|---|---|---|---|---|---|---|
| Blood | 18.8 +/− 1.5 | 15.6 +/− 1.9 | 15.8 +/− 3.0 | 11.1 +/− 0.6 | 6.78 +/− 2.94 | 7.51 +/− 2.04 |
| Lung | 6.12 +/− 1.08 | 6.35 +/− 2.01 | 6.63 +/− 1.77 | 6.90 +/− 2.67 | 3.37 +/− 1.28 | 5.11 +/− 2.57 |
| Liver | 18.9 +/− 2.1 | 17.5 +/− 2.3 | 18.4 +/− 4.4 | 10.3 +/− 0.6 | 12.6 +/− 1.8 | 9.70 +/− 1.48 |
| Spleen | 11.4 +/− 2.9 | 9.80 +/− 2.65 | 12.8 +/− 2.0 | 7.98 +/− 0.77 | 7.87 +/− 1.29 | 5.54 +/− 1.76 |
| Kidney | 9.44 +/− 0.87 | 8.66 +/− 1.01 | 8.41 +/− 1.36 | 5.61 +/− 0.46 | 5.12 +/− 0.56 | 4.20 +/− 0.55 |
| Bladder | 67.6 +/− 56.1 | 32.6 +/− 20.2 | 10.8 +/− 7.4 | 1.60 +/− 0.15 | 1.90 +/− 0.85 | 2.11 +/− 0.45 |
| Muscle | 0.51 +/− 0.18 | 0.57 +/− 0.12 | 0.93 +/− 0.23 | 0.97 +/− 0.09 | 0.94 +/− 0.31 | 0.84 +/− 0.18 |
| Fat | 1.27 +/− 0.37 | 1.39 +/− 0.31 | 1.23 +/− 0.30 | 1.33 +/− 0.53 | 1.34 +/− 0.45 | 1.05 +/− 0.35 |
| Heart | 3.95 +/− 1.05 | 4.11 +/− 0.75 | 4.35 +/− 0.57 | 3.01 +/− 0.34 | 1.81 +/− 0.76 | 2.30 +/− 0.62 |
| Brain | 0.64 +/− 0.18 | 0.54 +/− 0.07 | 0.53 +/− 0.08 | 0.42 +/− 0.13 | 0.25 +/− 0.08 | 0.30 +/− 0.08 |
| Bone | 2.60 +/− 0.35 | 2.72 +/− 0.56 | 2.55 +/− 0.58 | 1.73 +/− 0.17 | 1.52 +/− 0.40 | 1.68 +/− 0.46 |
| Marrow | 6.75 +/− 1.06 | 6.50 +/− 4.02 | 5.67 +/− 2.19 | 3.84 +/− 1.55 | 3.85 +/− 0.82 | 10.2 +/− 5.4 |
| Testes | 1.36 +/− 0.22 | 1.63 +/− 0.17 | 1.77 +/− 0.41 | 1.45 +/− 0.09 | 1.12 +/− 0.36 | 1.15 +/− 0.26 |
| Adrenals | 5.11 +/− 0.36 | 4.50 +/− 1.27 | 5.06 +/− 1.54 | 3.36 +/− 0.75 | 2.69 +/− 0.55 | 3.40 +/− 1.71 |
| Thyroid | 4.00 +/− 1.20 | 4.04 +/− 1.43 | 3.52 +/− 0.96 | 3.81 +/− 1.29 | 2.11 +/− 1.40 | 1.42 +/− 0.49 |
| Pancreas | 1.36 +/− 0.12 | 1.26 +/− 0.30 | 1.78 +/− 0.61 | 1.47 +/− 0.12 | 1.17 +/− 0.54 | 1.25 +/− 0.28 |
| Stomach | 1.40 +/− 0.08 | 1.41 +/− 0.29 | 1.38 +/− 0.33 | 1.13 +/− 0.23 | 1.19 +/− 0.48 | 1.09 +/− 0.25 |
| Small Intestines | 1.95 +/− 0.20 | 1.92 +/− 0.33 | 1.95 +/− 0.28 | 1.69 +/− 0.18 | 1.55 +/− 0.48 | 1.60 +/− 0.22 |
| Upper L. Intestines | 1.86 +/− 0.40 | 2.11 +/− 0.34 | 1.66 +/− 0.23 | 1.53 +/− 0.17 | 1.58 +/− 0.47 | 1.46 +/− 0.24 |
| Lower L. Intestines | 0.92 +/− 0.12 | 1.71 +/− 0.18 | 1.96 +/− 0.46 | 1.50 +/− 0.17 | 1.66 +/− 0.46 | 1.74 +/− 0.21 |

Residence Times

Figure 10A:
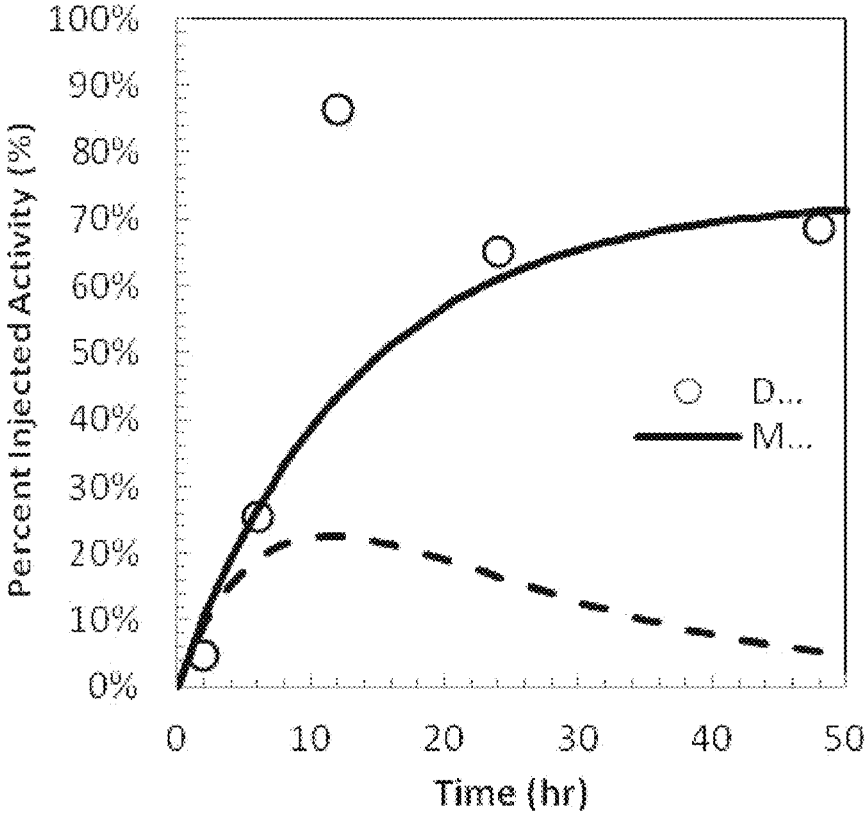
FIG. 10 depicts two graphs showing urine (A) and feces (B) excretion data plotted as a function of time. The heavy dash lines represent fit with an uptake function used to calculate the total amount of activity excreted expressed in units of hours. The light dash lines show the fit accounting for radio-active decay.
Figure 10B:
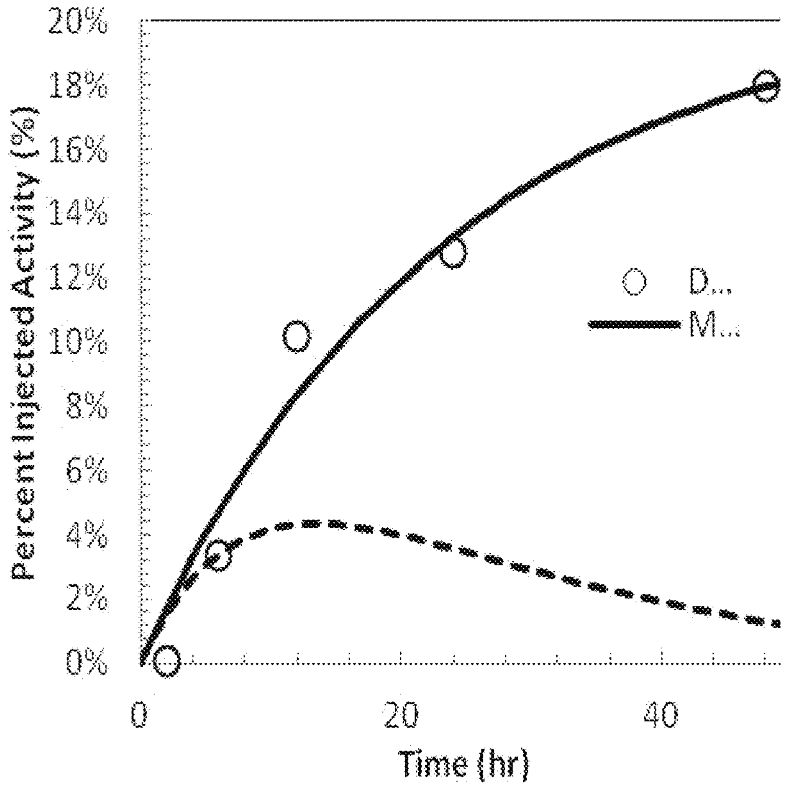
Figure 11:
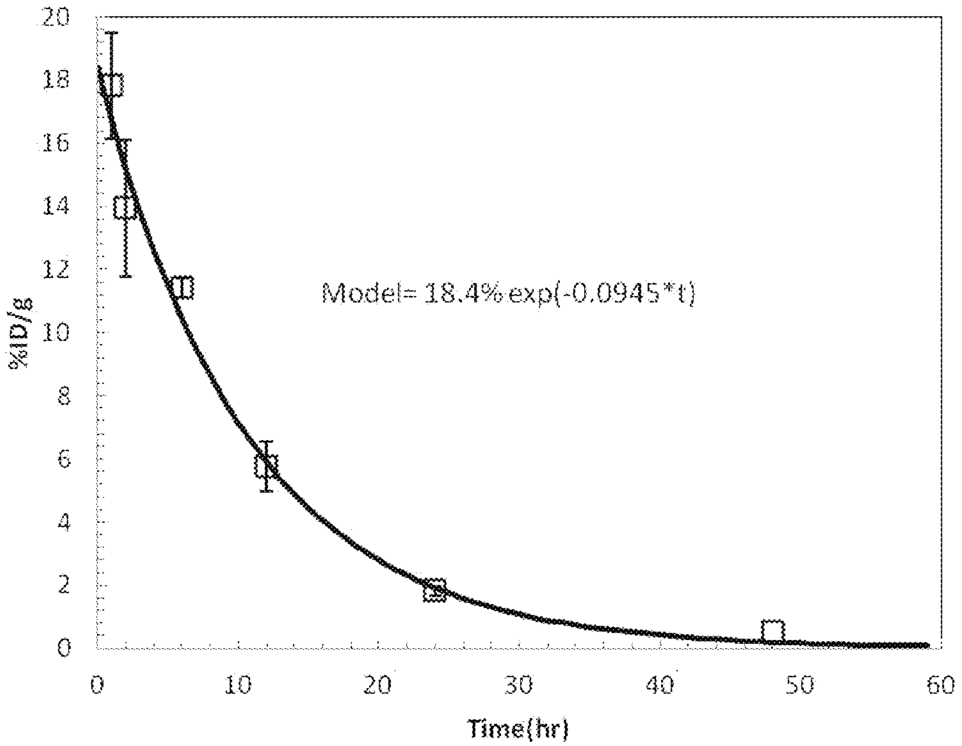
FIG. 11 depicts a plot showing blood clearance.

The residence time represents the cumulative presence time of radioactivity in any given organ and is expressed in units of time (either seconds, minutes or hours). Multiplying these values by unit of radioactivity leads to the number of radio-active decays occurring in any given organ and is therefore proportional to radiation dose. Using the above animal biodistribution data, the organ residence times (in hour) for each harvested organ were calculated by numerical integration of the time activity data expressed in percent injected dose per gram of tissue. The following initial organ activity content immediately after injection was assumed to be: 5.9% in the lungs, 2.9% in the liver, 1.5% in the spleen and kidneys, 3.7% in the bone, and 72% in the blood. It was assumed that no biological excretion occurred beyond the last measured time point and that radio-activity only decreased due to physical decay. The animal organ residence times were then scaled to human organ weight by the "relative organ mass scaling" method. Organ residence times are presented in Table 2. The cumulative urine and feces activity (in percent injected) were plotted as a function of time and an uptake function was fitted to the data ($F(t)=A0\ (1-\exp(-A1\ t))$, see FIGS. 10A and B). Analytical integration, accounting for radio-active decay, yielded to an excreted residence time of 1.62 hr in the feces. Analytical integration of the excreted urine data resulted in a urine residence times of 7.75 hr. The filling fraction of 73% and the filling half-life of 9.23 hr (=ln(2)/0.075 hr-1) was used in the MIRD voiding model along with a voiding interval of 2 hr to yield a bladder residence time of 0.425 hr. The amount of excreted activity is therefore equal to 9.4 hr. The remainder of the body residence time was calculated from the maximum theoretical residence time minus the excreted residence time minus the sum of all residence times measured in the organ above at the exception of blood and fat. This resulted in a residence time associated to the remainder of the body of 0.78 hr. The blood and bone mass was assumed to be 8% and 15% of the human body mass, respectively. The errors bars on the measured residence times were determined from the standard deviation of the biodistribution data points. The largest residence times are observed in the liver, muscle and bone. The residence time in the blood is also very high with a value of 4.58 hr and is dependent on the relative slow clearance of the activity from the blood (FIG. 11). The blood clearance was observed to clearing component with a biological half-life of 7.3 hr using a mono-exponential model.

TABLE 2

Organ residence times extrapolated to human expressed in hours.

| Organ | Residence Time (hr) |
|---|---|
| Blood | 4.58 |
| Lung | 0.41 |
| Liver | 1.65 |
| Spleen | 0.11 |
| Kidney | 0.12 |
| Muscle | 1.53 |
| Fat | 0.59 |
| Heart | 0.061 |
| Brain | 0.036 |
| Bone | 1.40 |
| Red Marrow | 0.38 |
| Testes | 0.0035 |
| Adrenals | 0.0038 |
| Thyroid | 0.0040 |
| Pancreas | 0.0083 |
| Stomach | 0.012 |
| Small Intestines | 0.074 |
| Upper L. Intestines | 0.023 |
| Lower L. Intestines | 0.023 |
| Bladder Wall | 0.032 |

Radiation Dosimetry

The residence times of Table 2 were entered in the program OLINDA/EXM for $^{64}$Cu and using the standard MIRD adult male model. The following additional assumptions were made: 10% of the blood residence time was assigned to the heart left ventricle; the bone activity was assigned in equal part to the cortical and trabecular bone source organs. Organ radiation dose estimates for the adult male model are presented in Table 3. The error bars on the dose estimates were assumed to be in proportion of the organ residence times uncertainties.

TABLE 3

Extrapolated human radiation dose estimates for $^{64}$Cu-DOTA-2C6F3 antibody per unit of administered activity. Radiation doses can be converted to the SI units of mGy/MBq by dividing by 3.7.

| Organ | Dose (rad/mCi) |
|---|---|
| Adrenals | 0.0926 |
| Brain | 0.0141 |
| Breasts | 0.0139 |
| Gallbladder | 0.0378 |
| LLI Wall | 0.0347 |
| Small Intestines | 0.0426 |
| Stomach | 0.0258 |
| ULI Wall | 0.0343 |
| Heart muscle | 0.217 |
| Kidneys | 0.137 |
| Liver | 0.295 |
| Lungs | 0.134 |
| Muscle | 0.0274 |
| Ovaries | 0.0193 |
| Pancreas | 0.051 |
| Red Marrow | 0.107 |
| Bones | 0.0232 |
| Skin | 0.0105 |
| Spleen | 0.192 |

TABLE 3-continued

Extrapolated human radiation dose estimates for $^{64}$Cu-DOTA-2C6F3 antibody per unit of administered activity. Radiation doses can be converted to the SI units of mGy/MBq by dividing by 3.7.

| Organ | Dose (rad/mCi) |
|---|---|
| Testes | 0.0342 |
| Thymus | 0.0207 |
| Thyroid | 0.063 |
| Urinary Bladder | 0.321 |
| Uterus | 0.0228 |
| Total Body | 0.039 |
| Effective Dose (rem/mCi) | 0.083 |

Although the calculated doses are for the human male model, dose to female organs (breasts, uterus and ovaries) are also provided in italic. The radiation doses above include contribution from beta (both minus and plus) and gamma rays emitted from $^{64}$Cu, and include contribution from activity within one organ to itself and from neighboring organs. Due to the nature and energy of the beta particles, the self-organ dose contribution from the beta particles dominates the dose contributions. The largest radiation dose is observed in the liver and urinary bladder wall with values of 0.295 and 0.321 rad per mCi injected. The effective dose is calculated at 0.083 rem/mCi. Based on RDRC limit of 5 rem to any organ, this indicates a 16 mCi maximum injection.

Example 4

Dosimetry of Labeled Anti-TIP1 2C6F3 antibody

Biodistribution in Healthy Mice

Human radiation dosimetry estimates were calculated from animal biodistribution data obtained by standard method of organ dissection and using the standard MIRD methodology. Animal biodistribution data was obtained using 30 C57 mature male mice injected with 24 μCi/100 μL of [$^{64}$Cu]-DOTA-2C6F3 antibody divided in 6 groups of 5 animals. The average animal mouse weight was 23.3 g. Animals were euthanized and organs were harvested in groups of five at the following time points: 1, 2, 6, 12, 24 and 48 hours post injection. The following organs were harvested, weighed and counted for radio-activity in a gamma counter: blood, lungs, liver, spleen, kidneys, bladder, muscle, fat, heart, brain, bone, red marrow, testes, adrenals, thyroid, pancreas, stomach, small intestines, upper and lower large intestines. The animals were maintained in metabolic cages where urine and feces excretion were collected, weighed and counted for radioactivity. The biodistribution data are presented in Table 4.

TABLE 4

Organ activity concentration from mice dissection expressed in percent injected per gram of tissue.

| Organ | 1 hr | 2 hr | 6 hr | 12 hr | 24 hr | 48 hr |
|---|---|---|---|---|---|---|
| Blood | 11.3 ± 1.3 | 9.02 ± 1.32 | 8.52 ± 1.14 | 5.80 ± 1.21 | 3.85 ± 0.58 | 4.62 ± 0.68 |
| Lung | 5.06 ± 1.35 | 3.99 ± 1.26 | 4.48 ± 1.07 | 4.04 ± 1.82 | 2.46 ± 1.36 | 3.20 ± 0.53 |
| Liver | 49.0 ± 7.83 | 38.3 ± 5.8 | 42.7 ± 2.36 | 28.7 ± 5.7 | 25.1 ± 2.7 | 18.0 ± 4.6 |
| Spleen | 56.5 ± 12.4 | 36.7 ± 13.9 | 45.6 ± 15.9 | 33.7 ± 6.9 | 24.0 ± 4.9 | 18.8 ± 7.9 |
| Kidney | 6.17 ± 0.69 | 5.65 ± 0.72 | 6.11 ± 1.00 | 4.93 ± 1.34 | 3.76 ± 0.37 | 4.42 ± 0.48 |
| Bladder | 36.0 ± 28.8 | 32.6 ± 26.4 | 8.40 ± 7.04 | 2.74 ± 0.66 | 1.97 ± 0.67 | 2.31 ± 0.72 |
| Muscle | 0.40 ± 0.14 | 0.68 ± 0.80 | 0.46 ± 0.05 | 0.59 ± 0.17 | 0.51 ± 0.09 | 0.75 ± 0.35 |
| Fat | 0.62 ± 0.22 | 0.93 ± 0.29 | 1.10 ± 0.25 | 0.80 ± 0.17 | 1.08 ± 0.43 | 0.67 ± 0.07 |
| Heart | 2.58 ± 0.57 | 2.51 ± 0.94 | 2.32 ± 0.64 | 1.85 ± 0.39 | 1.37 ± 0.16 | 1.75 ± 0.31 |
| Brain | 0.45 ± 0.26 | 0.30 ± 0.07 | 0.31 ± 0.09 | 0.25 ± 0.11 | 0.20 ± 0.04 | 0.25 ± 0.05 |
| Bone | 1.63 ± 0.32 | 1.52 ± 0.31 | 1.42 ± 0.25 | 0.98 ± 0.30 | 1.16 ± 0.63 | 0.96 ± 0.13 |
| Marrow | 3.67 ± 1.42 | 3.64 ± 1.58 | 2.47 ± 1.26 | 0.96 ± 0.51 | 0.89 ± 0.23 | 1.36 ± 2.67 |
| Testes | 0.66 ± 0.13 | 0.82 ± 0.12 | 0.94 ± 0.08 | 0.78 ± 0.20 | 0.63 ± 0.12 | 0.76 ± 0.09 |
| Adrenals | 3.35 ± 1.15 | 3.00 ± 0.72 | 2.14 ± 0.52 | 2.00 ± 0.34 | 1.87 ± 0.37 | 2.24 ± 0.95 |
| Thyroid | 2.36 ± 0.76 | 2.14 ± 0.78 | 1.67 ± 0.54 | 1.46 ± 0.50 | 1.39 ± 0.24 | 2.01 ± 0.83 |
| Pancreas | 0.96 ± 0.27 | 0.87 ± 0.20 | 0.99 ± 0.21 | 0.76 ± 0.12 | 0.86 ± 0.34 | 1.04 ± 0.15 |
| Stomach | 1.19 ± 0.21 | 0.96 ± 0.26 | 1.06 ± 0.19 | 0.62 ± 0.12 | 0.87 ± 0.17 | 1.47 ± 0.35 |
| Small Intestines | 1.43 ± 0.28 | 1.17 ± 0.24 | 1.25 ± 0.12 | 1.24 ± 0.16 | 1.20 ± 0.22 | 1.79 ± 0.39 |
| Upper L. Intestines | 1.21 ± 0.29 | 1.01 ± 0.11 | 1.10 ± 0.18 | 1.16 ± 0.20 | 1.21 ± 0.15 | 1.76 ± 0.27 |
| Lower L. Intestines | 0.67 ± 0.10 | 1.22 ± 0.09 | 1.25 ± 0.17 | 1.38 ± 0.27 | 1.51 ± 0.31 | 1.98 ± 0.34 |

Residence Times

Figure 12A:
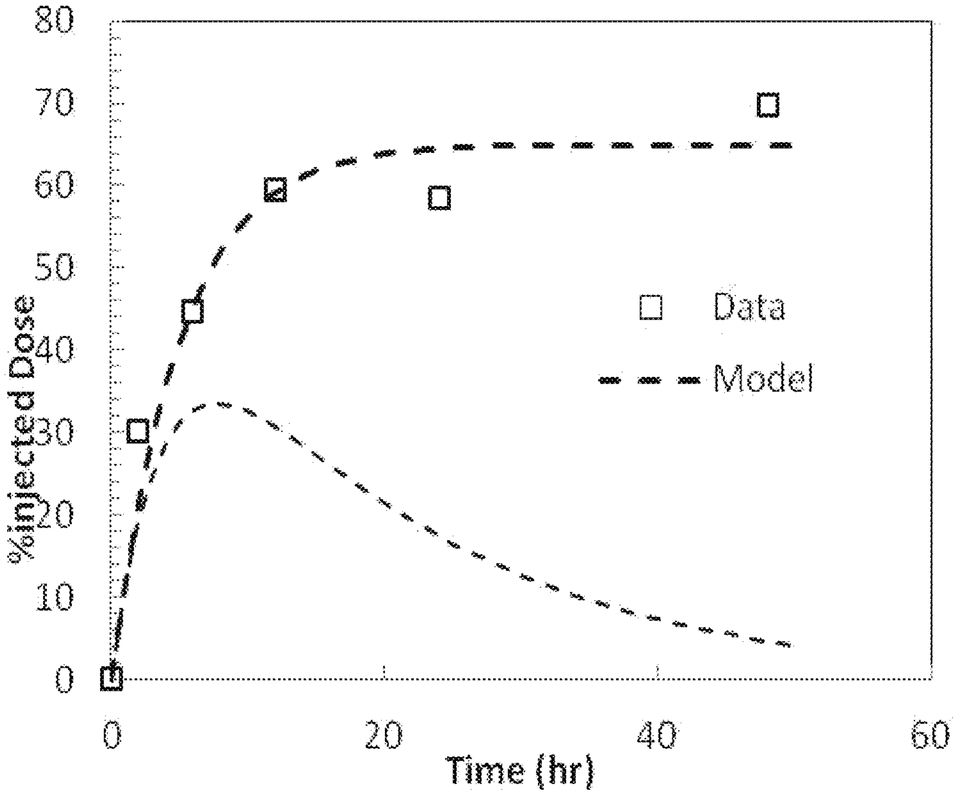
FIG. 12 depicts two graphs showing urine (A) and feces (B) excretion data plotted as a function of time. The heavy dash lines represent fit with an uptake function used to calculate the total amount of activity excreted expressed in units of hours. The light dash lines show the fit accounting for radioactive decay.
Figure 12B:
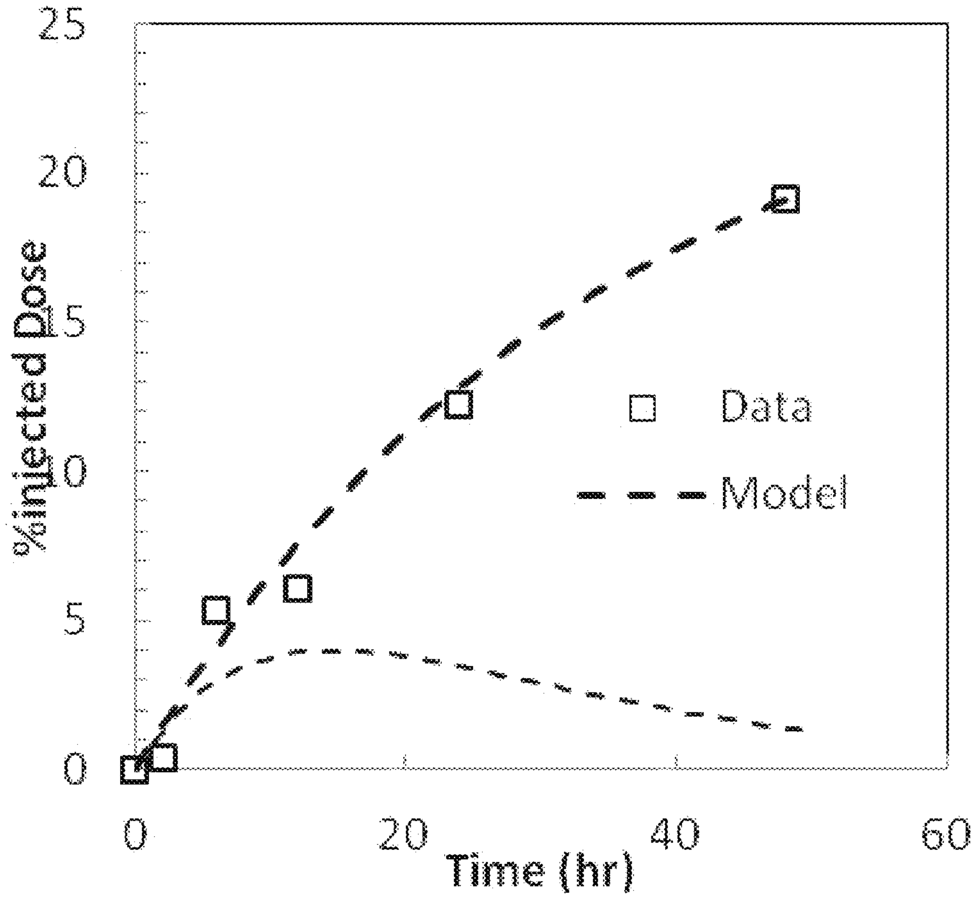

The residence times represent the cumulative presence time of radioactivity in any given organ and are expressed in units of second or hours (hr). Multiplying these values by unit of radioactivity leads to the number of radioactive decays occurring in any given organ and is therefore proportional to radiation dose. Using the above animal biodistribution data, the organ residence times (in hours) for each harvested organ were calculated by numerical integration of the time activity data expressed in percent injected dose per gram of tissue. The following initial organ activity content immediately after injection was assumed to be: 5.9% in the lungs, 2.9% in the liver, 1.5% in the spleen and kidneys, 3.7% in the bone, and 72% in the blood. It was assumed that no biological excretion occur beyond the last measured time point and that radioactivity only decreased due to physical decay. The animal organ residence times were then scaled to human organ weight by the "relative organ mass scaling" method. Organ residence times are presented in Table 5. The cumulative urine and feces activity (in percent injected) were plotted as a function of time and an uptake function was fitted to the data ($F(t)=A0\ (1-\exp(-A1\ t))$, see FIGS. 12A and B). Analytical integration, accounting for radioactive decay, yielded to an excreted residence time of 1.62 hr in the feces. Analytical integration of the excreted urine data resulted in a urine residence times of 9.36 hr. The filling fraction of 65% and the filling half-life of 3.47 hr (=ln(2)/0.020 hr−1) was used in the MIRD voiding model along with a voiding interval of 2 hr to yield a bladder residence time of 0.533 hr, and a modeled amount of activity excreted in urine of 8.83 hr. The amount of excreted activity is therefore equal to 10.5 hr. The remainder of the body residence time was calculated from the maximum theoretical residence time minus the excreted residence time minus the sum of all residence times measured in the organ above at the exception of blood and fat. This resulted in a residence time associated to the remainder of the body of 0.27 hr. The blood and bone mass was assumed to be 8% and 15% of the human body mass respectively. The errors bars on the measured residence times were determined from the standard deviation of the biodistribution data points. The largest residence times are observed in the liver, muscle and bone. The residence time in the blood is also very high with a value of 2.64 hr and is dependent on the relative slow clearance of the activity from the blood. The blood clearance half-life was measured at 36 hr using a mono-exponential model with an initial concentration of 11.3% of the injected dose.

TABLE 5

Organ residence times extrapolated to human expressed in hours.

| Organ | Residence Time (hr) |
|---|---|
| Blood | 2.64 ± 0.68 |
| Lung | 0.28 ± 0.12 |
| Liver | 3.52 ± 0.95 |
| Spleen | 0.36 ± 0.20 |
| Kidney | 0.09 ± 0.03 |
| Muscle | 0.92 ± 0.73 |
| Fat | 0.39 ± 0.22 |
| Heart | 0.036 ± 0.016 |
| Brain | 0.022 ± 0.014 |
| Bone | 0.80 ± 0.46 |
| Red Marrow | 0.11 ± 0.13 |
| Testes | 0.002 ± 0.001 |
| Adrenals | 0.002 ± 0.001 |
| Thyroid | 0.002 ± 0.001 |
| Pancreas | 0.005 ± 0.002 |
| Stomach | 0.009 ± 0.004 |
| Small Intestines | 0.05 ± 0.02 |
| Upper L. Intestines | 0.016 ± 0.005 |
| Lower L. Intestines | 0.014 ± 0.005 |
| Bladder Wall | 0.025 ± 0.036 |

Radiation Dosimetry

The residence times of Table 5 were entered in the program OLINDA/EXM for $^{64}$Cu and using the standard MIRD adult male model. The following additional assumptions were made: 10% of the blood residence time was assigned to the heart left ventricle; the bone activity was assigned in equal part to the cortical and trabecular bone source organs. The error bars on the dose estimates were assumed to be in proportion of the organ residence times uncertainties.

Although the calculated doses are for the human male model, dose to female organs (breasts, uterus and ovaries) are also provided in italics. The radiation doses above include contribution from beta (both minus and plus) and gamma rays emitted from $^{64}Cu$, and include contribution from activity within one organ to itself and from neighboring organs. Due to the nature and energy of the beta particles, the self-organ dose contribution from the beta particles dominates the dose contributions. The largest radiation dose is observed in the liver and spleen with values of 0.62 and 0.6 rad per mCi injected. The effective dose is calculated at 0.088 rem/mCi.

Example 5

GRP78 Surface Expression Increases on Irradiated NSCLC

Figure 13:
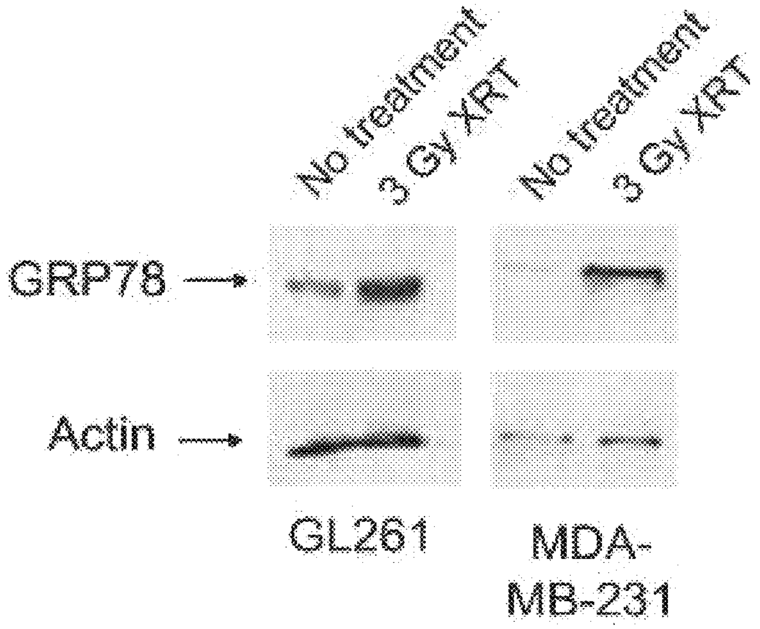
FIG. 13 depicts an image of a Western blot of GRP78 expression in XRT-treated and untreated (No Tx) MDA-MB-231 breast carcinoma tumor sections showing that GRP78 is upregulated to the membrane in response to XRT.
Figure 14:
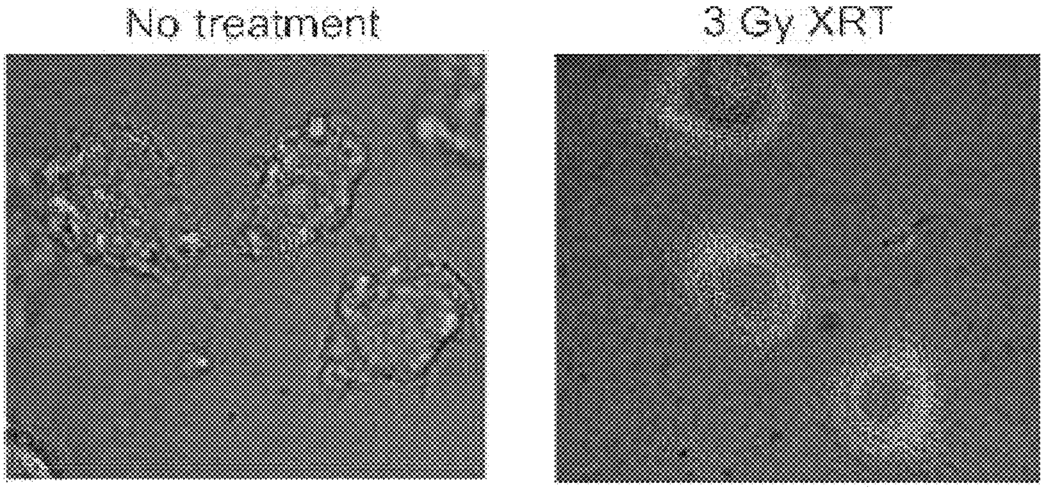
FIG. 14 depicts micrograph images showing GRP78 is induced in HUVECs grown in coculture with lung cancer cells after XRT treatment. Lung cancer cells ($3\times10^5$) and HUVECs ($1\times10^4$) were cocultured for 24 hours before treatment with 3 Gy XRT. Three hours posttreatment, AlexaFluor594-labeled GRP78 antibodies were added to the culture plates.

Lung cancer cell membrane preparations were studied on Western immunoblot. Antibodies to GRP78 showed an increase in this protein on the cell membrane in response to 3 Gy of irradiation in lung cancer cells (FIG. 13). GRP78 not only remained within the membrane preparations, but was also secreted into the medium of irradiated NSCLC cells. FIG. 14 shows that HUVEC cells irradiated together with lung cancer cells show an increase in GRP78 surface staining. Radiation induction of GRP78 on the surface of endothelial cells was not accomplished when endothelial cells were irradiated alone.

Example 6

Figure 15:
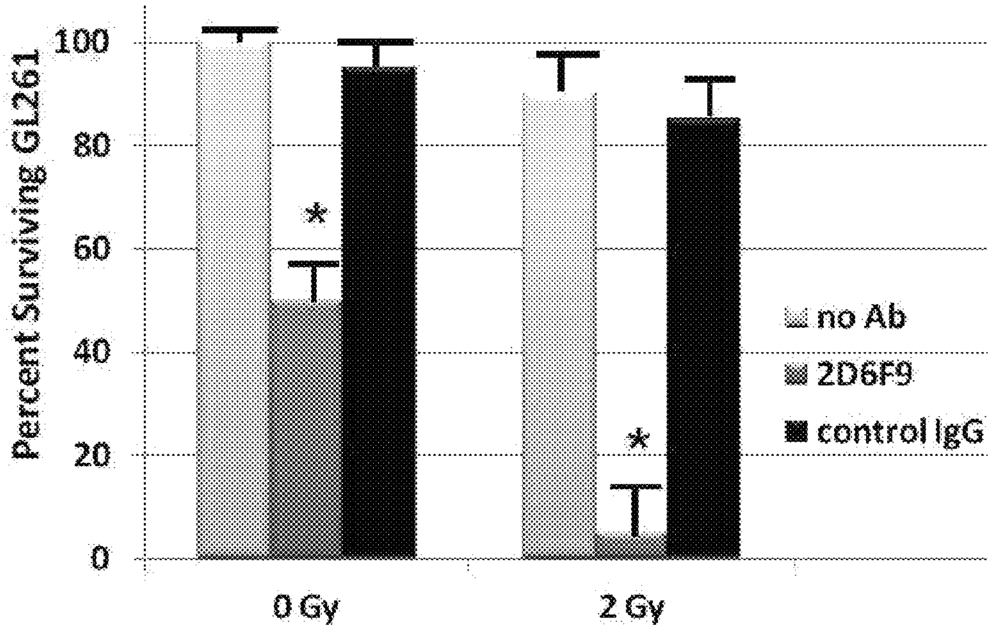
FIG. 15 depicts a plot showing that 2D6F3 enhances radiation induced cytotoxicity. Cancer cells were plated on 10 cm dishes and treated with Control IgG, 2D6F9 5 μg, or no antibody. 12 hours later cells were treated with 2 Gy or 0 Gy. The bar graph shows the percentage of MDA-MB231 glioma cells forming colonies after 7 days of incubation normalized to the untreated control. Shown is the mean and SEM of 3 experiments *$p<0.01$.

Anti-GRP78 Antibodies Reduce NSCLC Cell Survival and Enhance Cytotoxicity of Radiotherapy To determine whether anti-GRP78 monoclonal antibodies enhance the efficacy of radiotherapy in NSCLC, the colony forming assay was utilized (FIG. 15). 2D6F9 antibody, 5 μg/ml was added to lung cancer cells at 6 hours after plating. Cells were then treated with 2 Gy or sham irradiation (0 Gy). The antibody alone reduced plating efficiency to 49% and reduced survival to 6% after 2 Gy irradiation. In comparison, 2Gy alone or with control antibody reduced survival by less than 20% ($p<0.01$).

Example 7

Anti-GRP78 Antibodies Achieve Specific Binding to NSCLC in the Mouse Models

Figure 16:
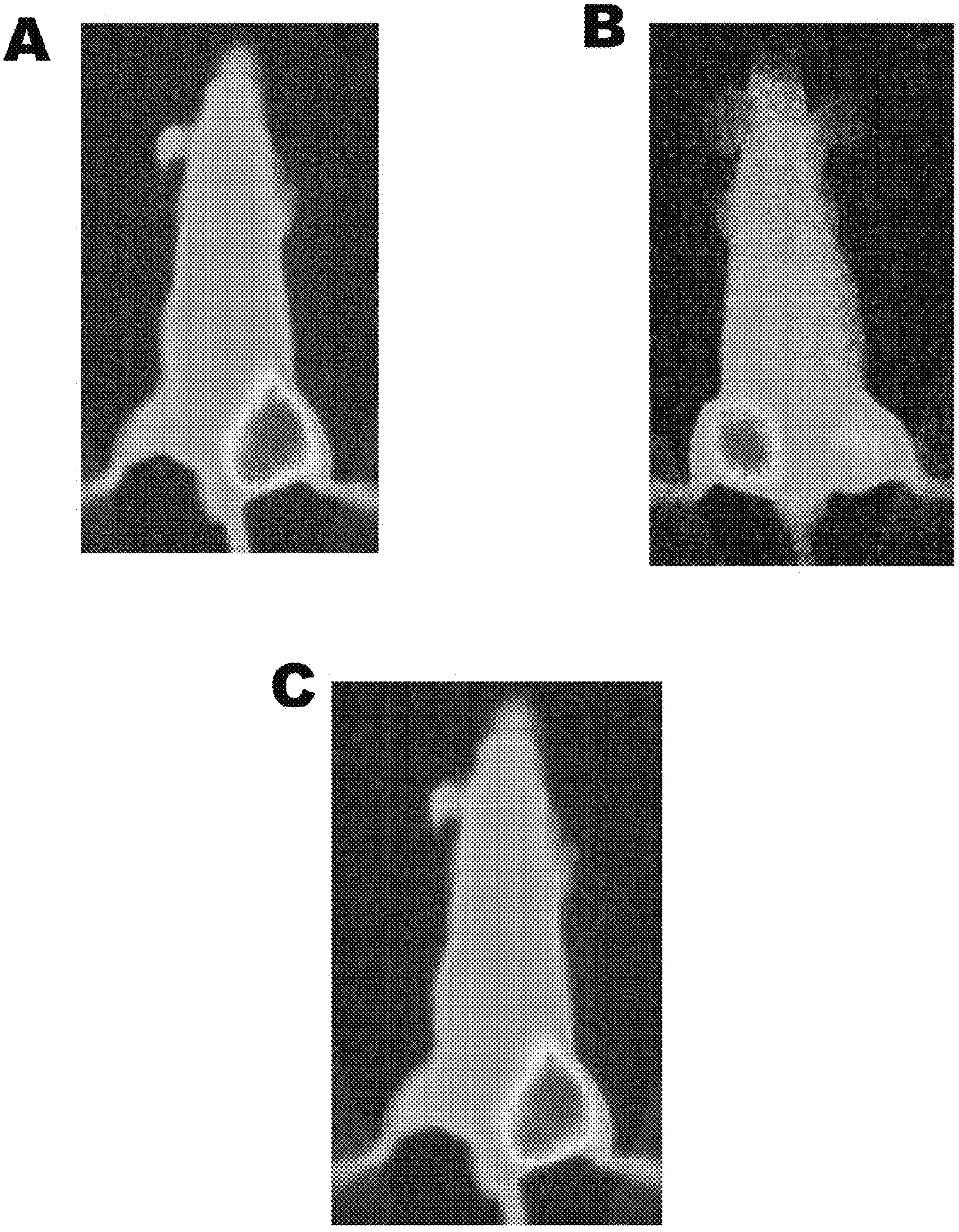
FIG. 16 depicts images of mice and a graph showing 1 D6B2, 2D6F3 and scFv binding in irradiated NSCLC in mice. Shown are near infrared images of mice obtained 48 hours after administration. Tumors were implanted into the hind limb of mice and treated with 3 Gy. (A) 1 D6B2 Ab was labeled with near infrared fluorophore ALX750 and injected immediately after irradiation. (B) 2D6F3 antibody labeled with ALX750 and injected immediately after treatment of tumors with 3Gy (left tumor) or 0 Gy (right tumor). (C) scFv antibody K13 labeled with ALX750 and injected immediately after irradiation of tumors. (D) Graph showing the time course of radiance (photons/sec/cm$^2$) from NIR images acquired daily after administration of 2D6F3.
Figure 16D:
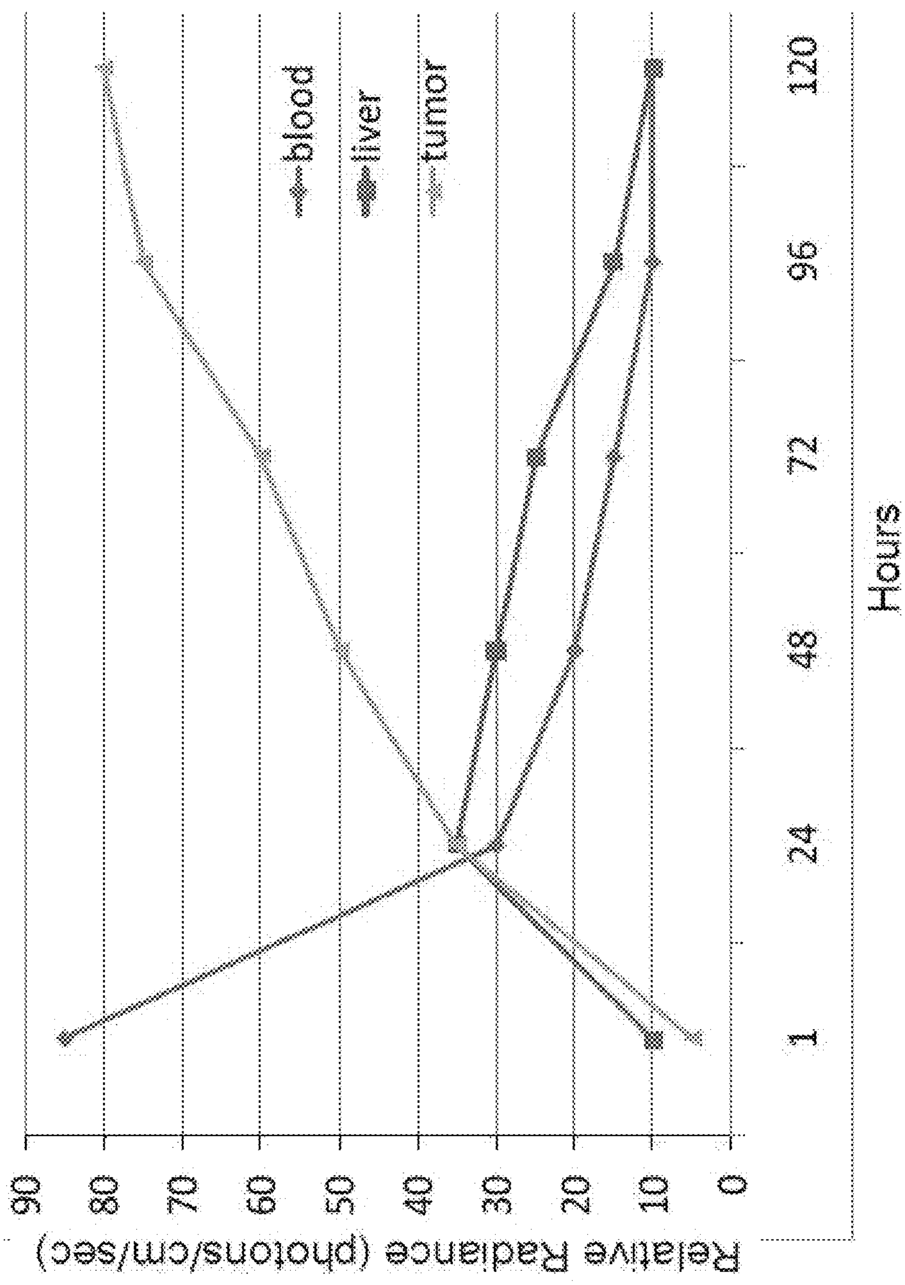

To determine whether antibodies against the C- and N-terminal domains of GRP78 achieve cancer specific binding, lung cancer tumors in mice (FIG. 16) were studied. Lung cancer tumors were grown both within the hind limb of mice. Antibodies were labeled with ALX750 and imaged by NIR imaging. Each of the antibodies 1 D6B2, 2D6F3 and scFv K13 achieve specific binding to the irradiated NSCLC. The kinetic curves show that the antibodies rapidly bind to the irradiated tumor as they are cleared from the circulation through enterohepatic clearance. Binding within tumors persist for over one week for IgG antibodies and 3 days for scFv. All antibodies also bind specifically to human NSCLCs H460 and LLC in irradiated nude mice.

TE11 anti TIP-1 scFv antibody and a DOTA-conjugated TE11 anti-TIP-1 scFv antibody were generated. The sequence of two TE11 clones are shown in FIG. 22.

Figure 17:
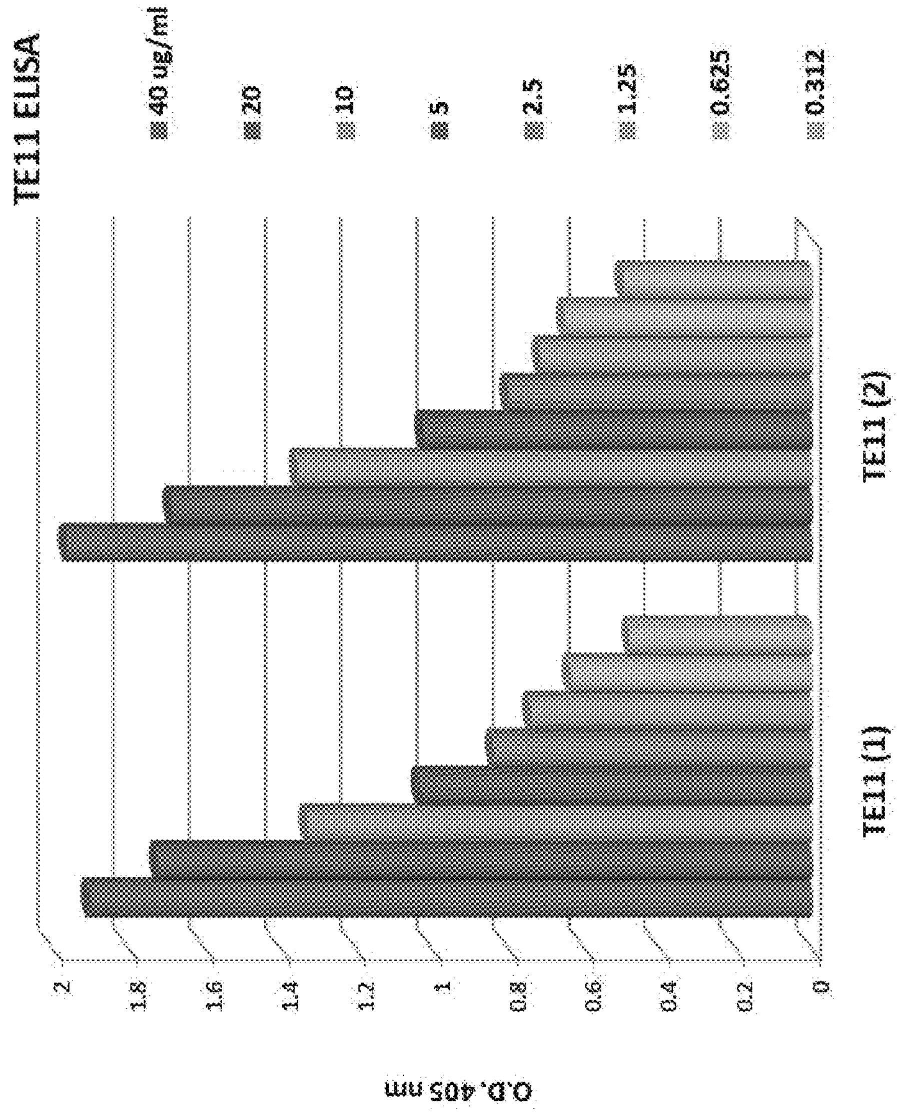
FIG. 17 depicts a graph showing specificity and binding activity to TIP-1 antigen using TE11 anti TIP-1 scFv antibody produced and prepared in two individual batches (TE11(1) and TE11(2)).
Figure 18:
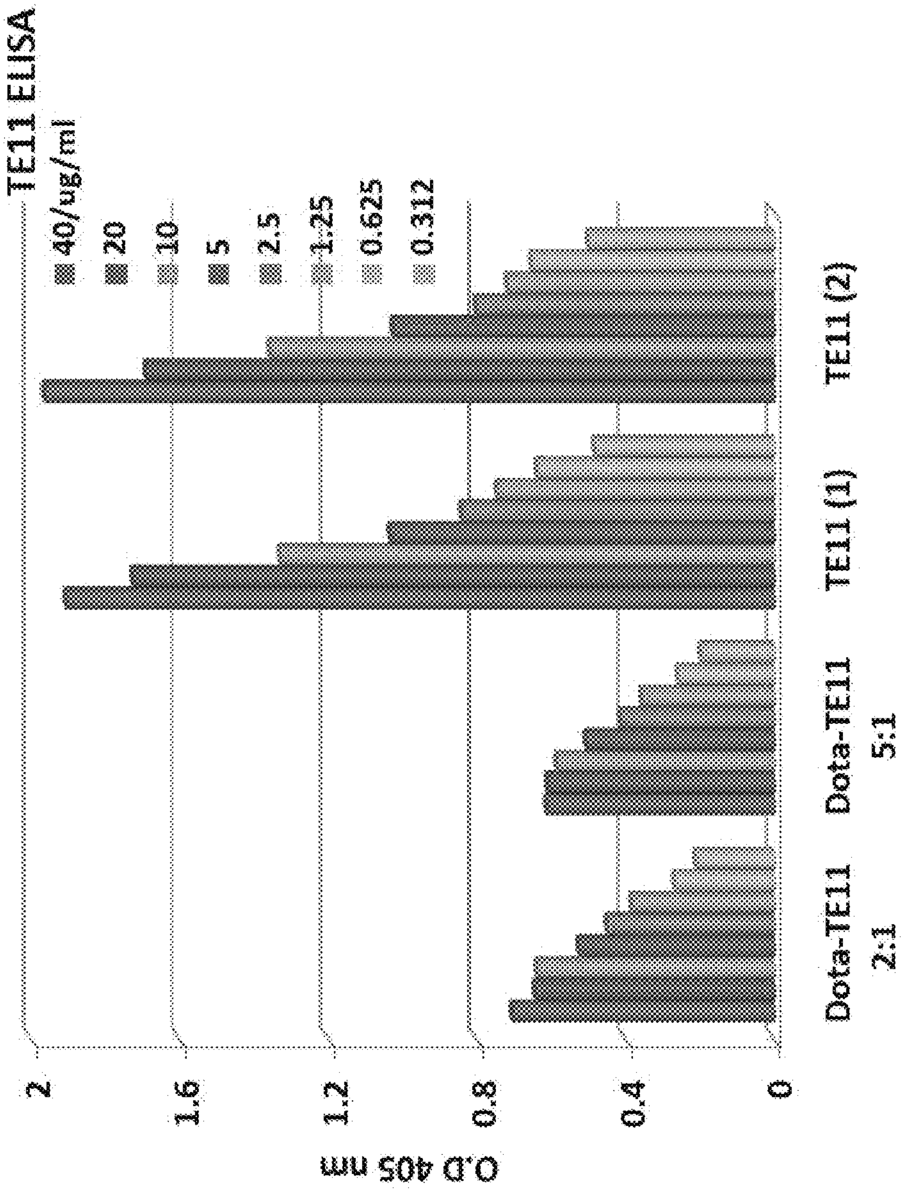
FIG. 18 depicts a graph showing a test of DOTA-conjugate TE11 anti TIP-1 scFv antibody.

The TE11 antibody was tested using ELISA (FIGS. 17 and 18). In short, ELISA plates were coated with TIP-1 antigen at 10 μg/ml in PBS, washed 3 times, and blocked with 2% BSA. TE11 or DOTA-conjugated TE11 in PBS was added and, after incubation, washed 3× before adding anti-myc antibody at 5 μg/ml, followed by goat anti-mouse IgG-HRP, washed 3× before adding ABTS substrate and reading at 405 nm. The reaction volume in each step is 50 μl/well.

Figure 19:
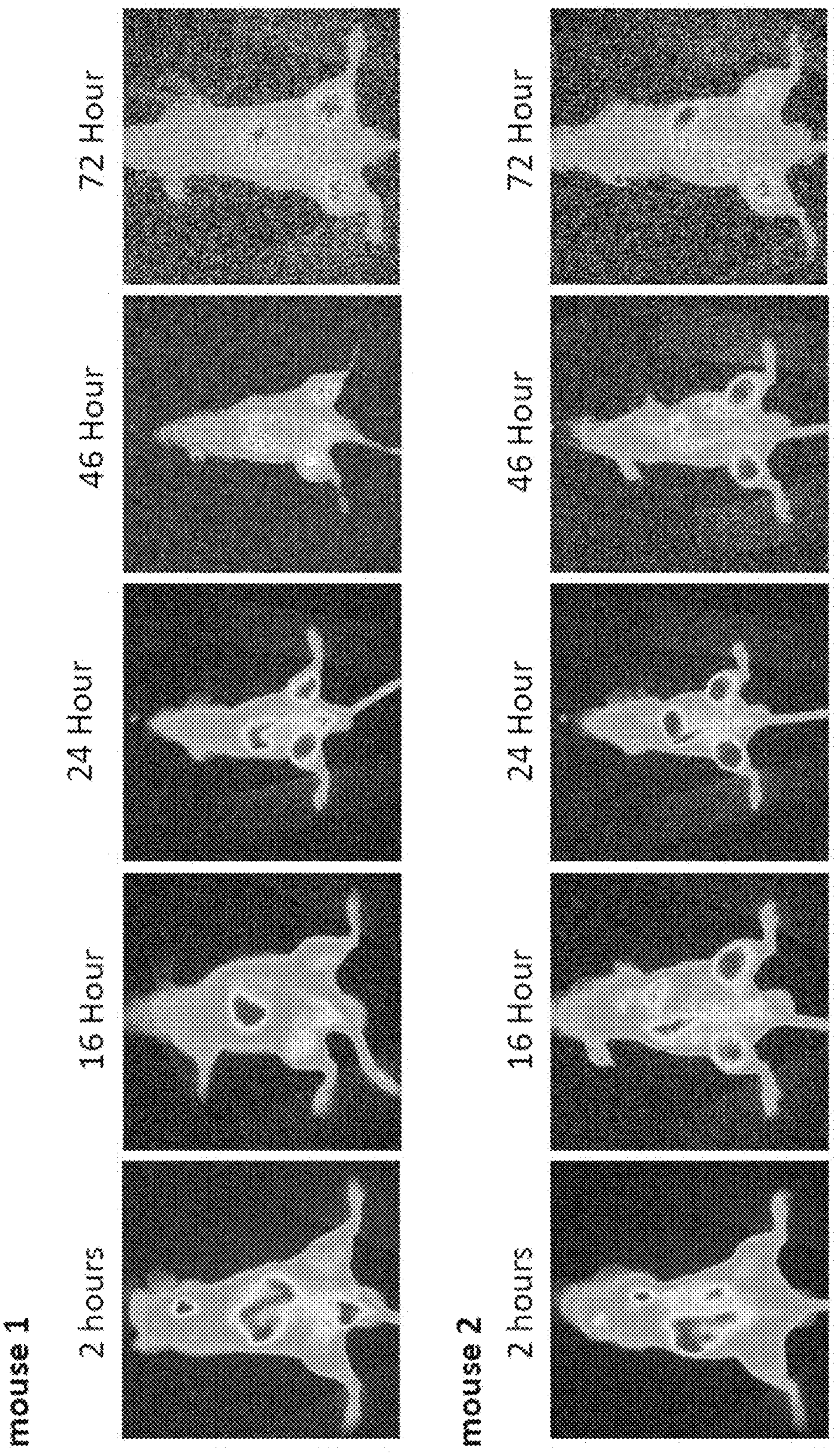
FIG. 19 depicts images of irradiated tumor bearing mice treated with anti-TIP-1 scFv antibody TE11. The mice were exposed to a single dose of 3Gy radiation on the hind left limb while there was no radiation exposure on the hind right limb. Following radiation exposure, each mouse was administered antibody. Images were taken at 2, 16, 24, 46, and 72 hours.
Figure 20:
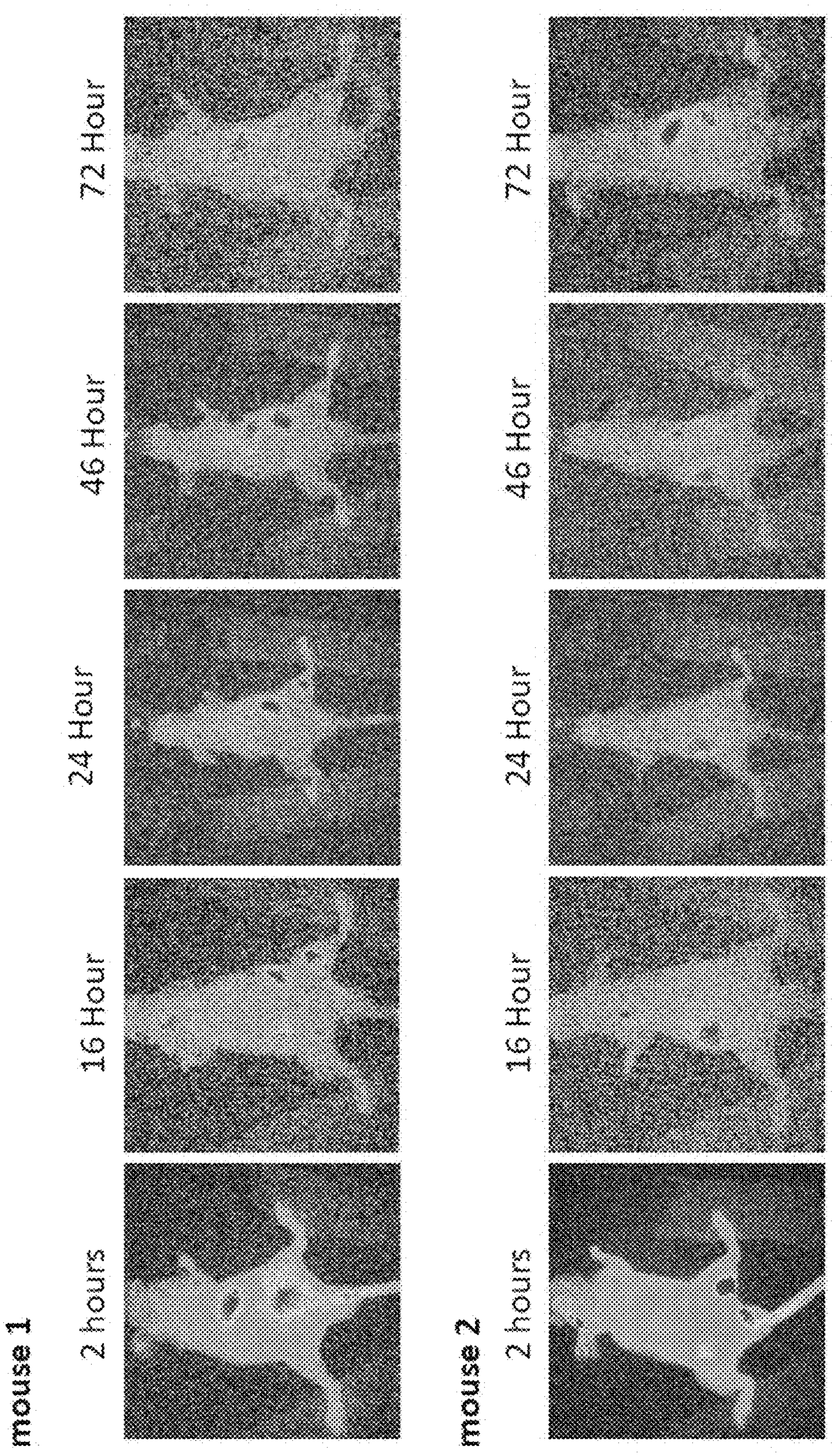
FIG. 20 depicts images of irradiated tumor bearing mice treated with control scFv antibody. The mice were exposed to a single dose of 3Gy radiation on the hind left limb while there was no radiation exposure on the hind right limb. Following radiation exposure, each mouse was administered antibody. Images were taken at 2, 16, 24, 46, and 72 hours.
Figure 21:
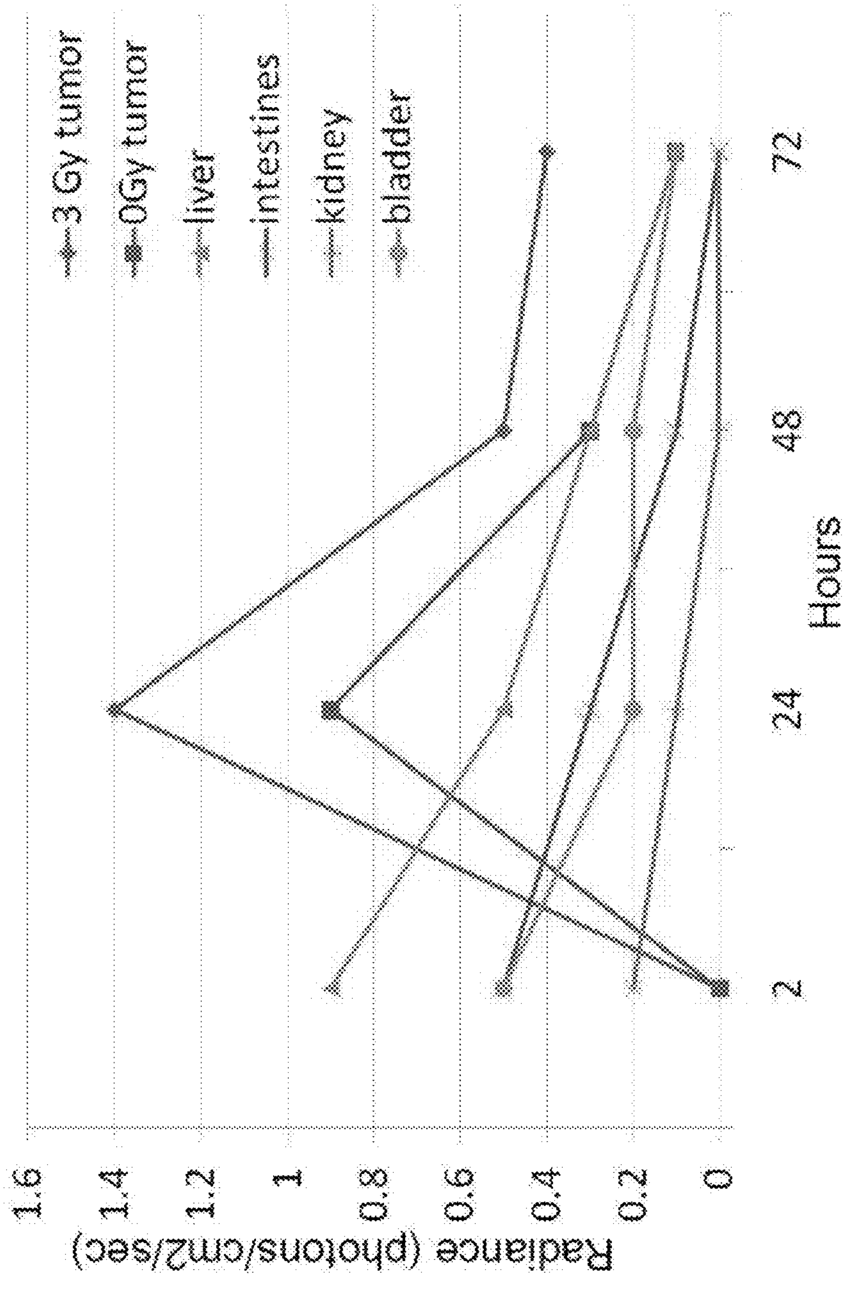
FIG. 21 depicts a graph showing the radiance emitted from the anti-TIP-1 scFv antibody TE11 over time.
Figure 23A:
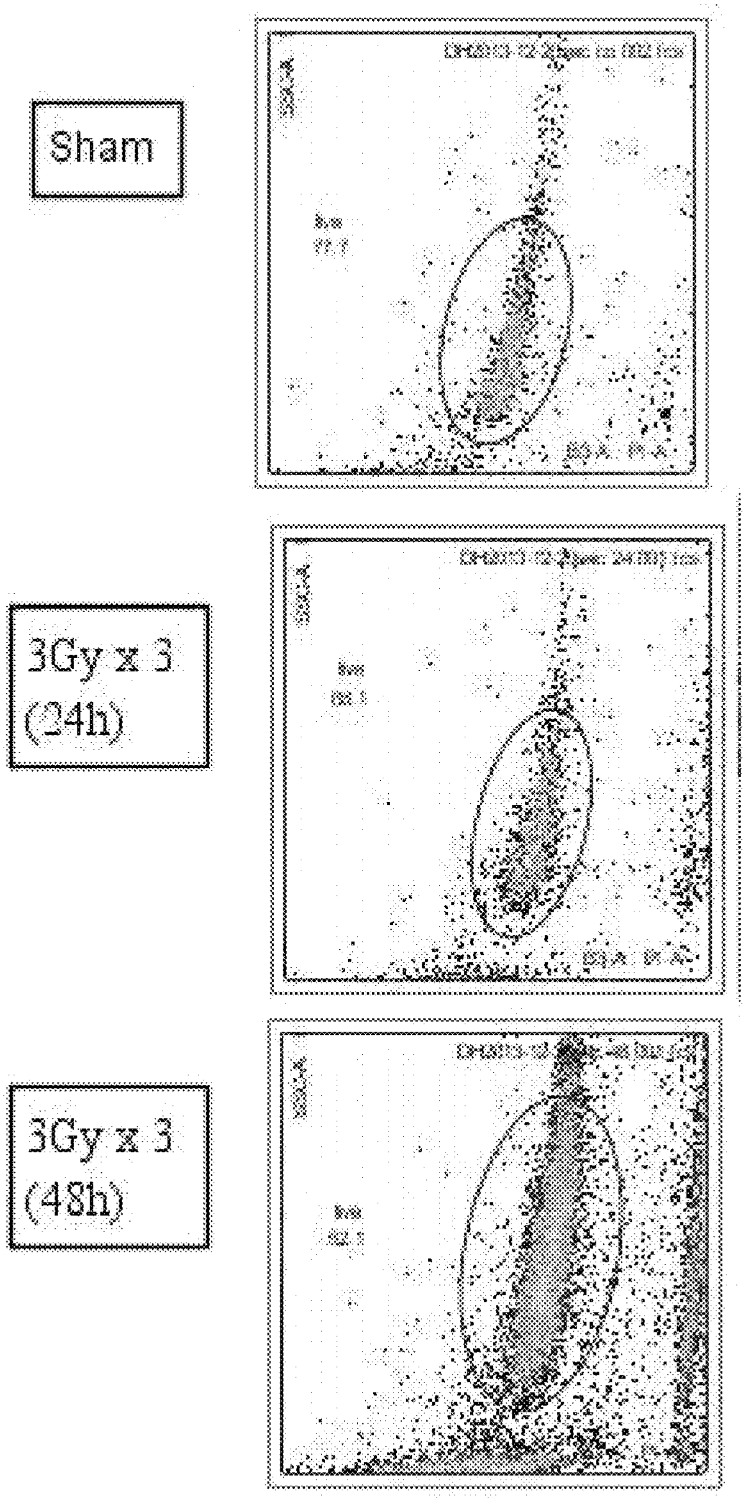
FIG. 23 depicts flow cytometry analysis of anti-TIP-1 monoclonal antibody, 2C6F3, binding on human glioblastoma D54 (WHO grade IV). (A) Depicts the cell population with the gated cells encircled. The top panel is sham treated cells, the middle panel is 3Gy×3 treated cells at 24h, the bottom panel is 3Gy×3 treated cells at 48 h. (B) Depicts the cell population stained with the secondary antibody. The top panel is sham treated cells, the middle panel is 3Gy×3 treated cells at 24h, the bottom panel is 3Gy×3 treated cells at 48 h. (C) Depicts the cell population stained with a commercial Tip-1 mAb. The top panel is sham treated cells, the middle panel is 3Gy×3 treated cells at 24h, the bottom panel is 3Gy×3 treated cells at 48 h. (D) Depicts the cell population stained with the 2C6F3 Ab. The top panel is sham treated cells, the middle panel is 3Gy×3 treated cells at 24h, the bottom panel is 3Gy×3 treated cells at 48 h.
Figure 23B:
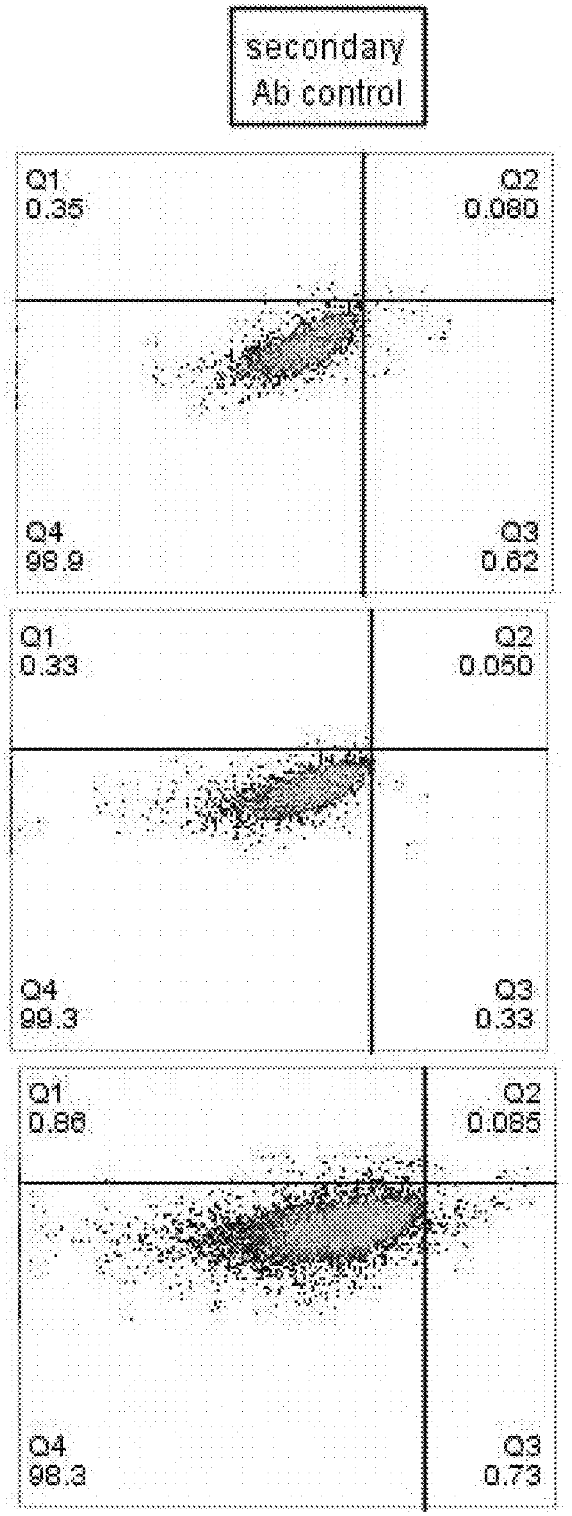
Figure 23C:
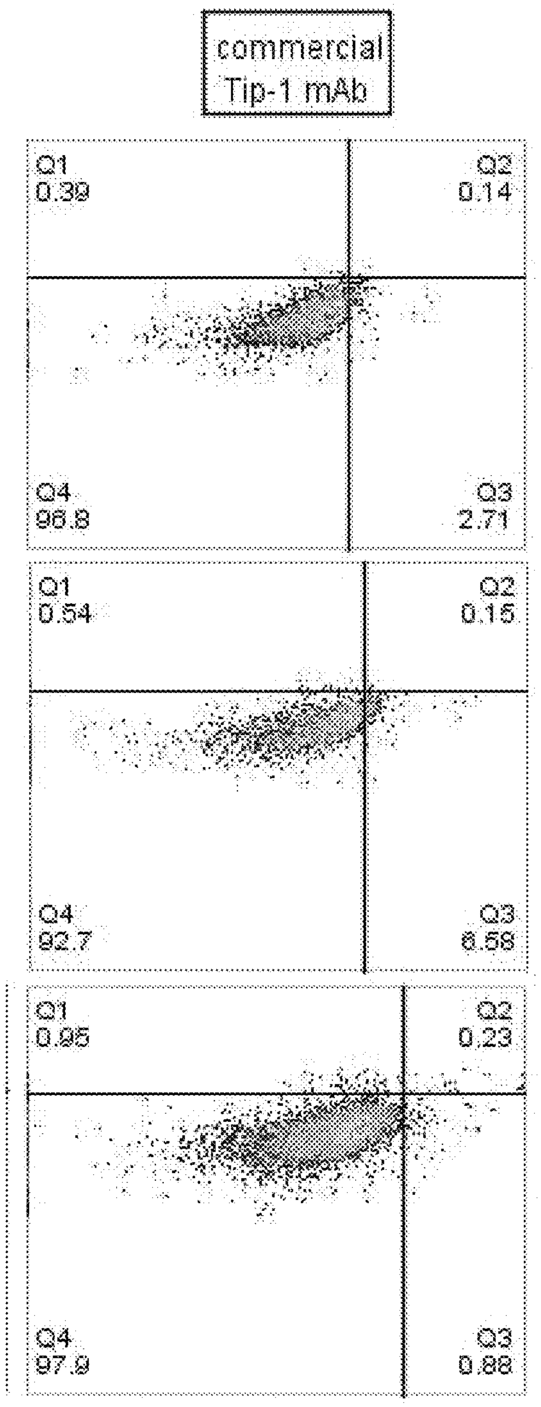
Figure 23D:
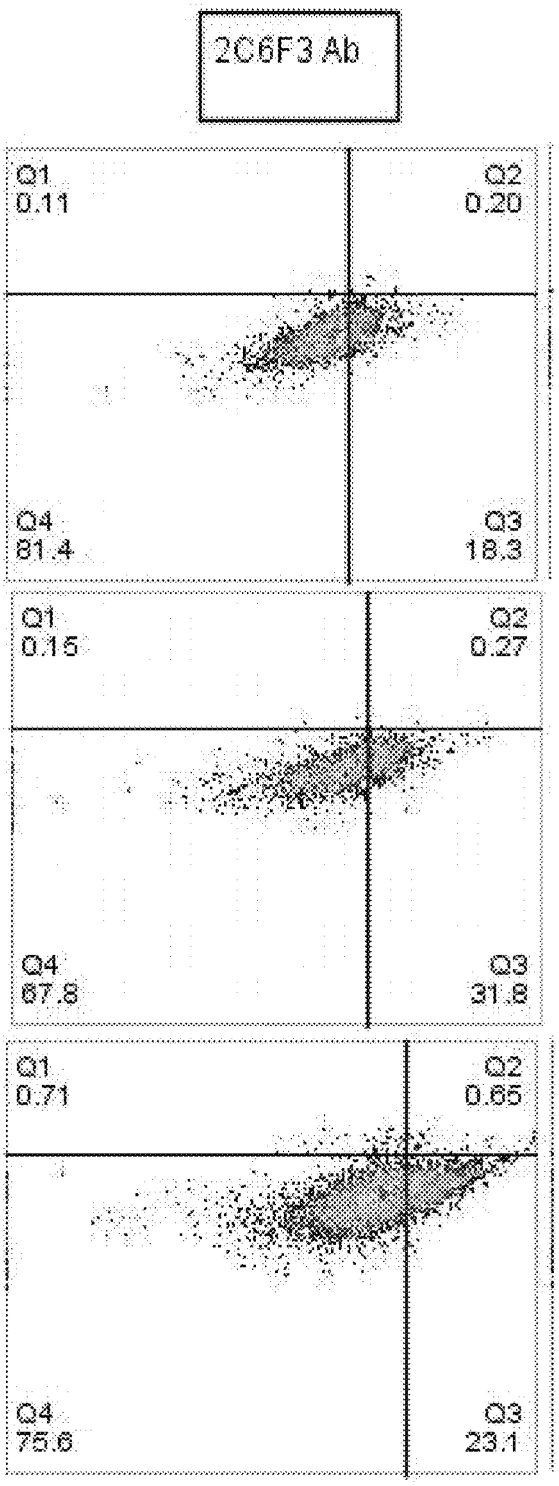

The anti-TIP-1 scFv antibody TE11 (FIG. 19) recognized tumor cells that were exposed to radiation, but a control scFv antibody did not (FIG. 20). See also FIG. 21.

Example 8

Humanizing Anti-TIP1 Antibody 2C6F3

The heavy chain (HC) and light chain (LC) sequences of 2C6F3, a murine antibody to TIP-1, were synthesized. The HC nucleic acid sequence is SEQ ID NO:24 and the amino acid sequence is SEQ ID NO:25 (Table C). The LC nucleic acid sequence is SEQ ID NO:26 and the amino acid sequence is SEQ ID NO:27 (Table C). According to the sequences, two plasmids for expressing murine HC and LC separately were constructed. The HC and LC genes were cloned into the plasmid under the control of PCMV promoter. The endotoxin free plasmids were isolated and transiently transfected into 293 cells. The antibody present in the supernatant was then tested by ELISA. Results showed the recombinant murine 2C6F3 antibody (2C6F3 rmlgG) binds to antigen as well as the original 2C6F3 antibody (2C6F3 mAb) (Table 6). The CDRs of the murine antibody are then cloned to a selected matching human IgG1 backbone.

TABLE 6

Quality control ELISA of 2C6F3 rmIgG in the TGE supernatant

| Antibody | $OD_{490}$ |
|---|---|
| 2C6F3 mAb | 1.398 |
| 2C6F3 rmIgG | 0.913 |
| Medium | 0.053 |
| PBS | 0.054 |

What is claimed is:

1. An isolated antibody that binds to Tax1-binding protein 3 (TIP-1), wherein the antibody comprises a heavy chain variable domain comprising a CDR1, CDR2, and a CDR3, wherein the heavy chain variable domain CDR1 comprises SEQ ID NO:28, the heavy chain variable region CDR2 comprises SEQ ID NO:29, and the heavy chain variable region CDR3 comprises SEQ ID NO:30; and a light chain variable domain comprising a CDR1, CDR2, and a CDR3, wherein the light chain variable domain CDR1 comprises SEQ ID NO:31, the light chain variable region domain CDR2 comprises SEQ ID NO:32, and the light chain variable region domain CDR3 comprises SEQ ID NO:33.

2. The antibody of claim 1, wherein the antibody is selected from the group consisting of a humanized antibody, a single chain variable fragment (scFv) antibody, an antigen-binding fragment, or a chimeric antibody.

3. The antibody of claim 1, wherein the antibody comprises a heavy chain variable region comprising SEQ ID NO:25 and a light chain variable region comprising SEQ ID NO:27.

4. The antibody of claim 1, wherein the antibody recognizes the epitope of SEQ ID NO:21.

5. The antibody of claim 1, wherein the antibody is conjugated directly or indirectly to a payload selected from the group consisting of a therapeutic agent, an imaging agent, or a combination thereof.

6. A method of enhancing radiotherapy in a subject, the method comprising administering a pharmacologically effective amount of an antibody of claim 5 to the subject, such that radiotherapy is enhanced.

7. The method of claim 6, further comprising administering ionizing radiation to the subject.

8. The method of claim 6, further comprising imaging the subject.

* * * * *

SEQUENCE LISTING

```
<160> NUMBER OF SEQ ID NOS: 33

<210> SEQ ID NO 1
<211> LENGTH: 10
<212> TYPE: PRT
<213> ORGANISM: Homo sapiens

<400> SEQUENCE: 1
```

-continued

```
Met Leu Leu Leu Leu Ser Ala Ala Arg Ala
1               5                   10


<210> SEQ ID NO 2
<211> LENGTH: 10
<212> TYPE: PRT
<213> ORGANISM: Homo sapiens

<400> SEQUENCE: 2

Met Lys Leu Ser Leu Val Ala Ala Met Leu
1               5                   10


<210> SEQ ID NO 3
<211> LENGTH: 18
<212> TYPE: PRT
<213> ORGANISM: Homo sapiens

<400> SEQUENCE: 3

Met Lys Leu Ser Leu Val Ala Ala Met Leu Leu Leu Leu Ser Ala Ala
1               5                   10                  15

Arg Ala


<210> SEQ ID NO 4
<211> LENGTH: 10
<212> TYPE: PRT
<213> ORGANISM: Homo sapiens

<400> SEQUENCE: 4

Glu Lys Asn Ile Leu Val Phe Asp Leu Gly
1               5                   10


<210> SEQ ID NO 5
<211> LENGTH: 354
<212> TYPE: DNA
<213> ORGANISM: Mus musculus

<400> SEQUENCE: 5

gaggttcagc tgcagcagtc tggacctgag ctggtgaagc ctggggcttc agtgaagata      60

tcctgcaagg cttctggtta ctcatttact ggctacttta tgaactgggt gaagcagagc     120

catggaaaga gccttgagtg gattggacgt attgatcctt acaatggtaa tattttctac     180

aaccagaagt tcaagggcaa ggccacattg actgtggaca aatcctctag cacagcccac     240

acggagctcc tgagcctgac atctgaggac tctgcagtct attattgtgg aaggtcctat     300

ggtaactatg ctttggacta ctggggtcaa ggaacctcag tcaccgtctc ctca           354


<210> SEQ ID NO 6
<211> LENGTH: 118
<212> TYPE: PRT
<213> ORGANISM: Mus musculus

<400> SEQUENCE: 6

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Phe Met Asn Trp Val Lys Gln Ser His Gly Lys Ser Leu Glu Trp Ile
        35                  40                  45

Gly Arg Ile Asp Pro Tyr Asn Gly Asn Ile Phe Tyr Asn Gln Lys Phe
    50                  55                  60

Lys Gly Lys Ala Thr Leu Thr Val Asp Lys Ser Ser Ser Thr Ala His
```

-continued

```
65                  70                  75                  80

Thr Glu Leu Leu Ser Leu Thr Ser Glu Asp Ser Ala Val Tyr Tyr Cys
                85                  90                  95

Gly Arg Ser Tyr Gly Asn Tyr Ala Leu Asp Tyr Trp Gly Gln Gly Thr
            100                 105                 110

Ser Val Thr Val Ser Ser
        115


<210> SEQ ID NO 7
<211> LENGTH: 321
<212> TYPE: DNA
<213> ORGANISM: Mus musculus

<400> SEQUENCE: 7

gatgtccaga taacccagtc tccatcttat cttgctgcat ctcctggaga aaccattact      60

attaattgca gggcaagtaa gagcattagc aaatatttag cctggtatca agagaaacct     120

gggaaaacta ataagcttct tatctacttt ggatccactt tgcaatctgg gattccatca     180

aggttcagtg gcagtggatc tggtacagat ttcactctca ccatcagtag cctggagcct     240

gaagattttg caatgtattt ctgtcaacag cataatgaat acccgtacac gttcggaggg     300

gggaccaagc tggaaatgaa a                                               321


<210> SEQ ID NO 8
<211> LENGTH: 107
<212> TYPE: PRT
<213> ORGANISM: Mus musculus

<400> SEQUENCE: 8

Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
            20                  25                  30

Leu Ala Trp Tyr Gln Glu Lys Pro Gly Lys Thr Asn Lys Leu Leu Ile
        35                  40                  45

Tyr Phe Gly Ser Thr Leu Gln Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Phe Cys Gln Gln His Asn Glu Tyr Pro Tyr
                85                  90                  95

Thr Phe Gly Gly Gly Thr Lys Leu Glu Met Lys
            100                 105


<210> SEQ ID NO 9
<211> LENGTH: 10
<212> TYPE: PRT
<213> ORGANISM: Homo sapiens

<400> SEQUENCE: 9

Gln Asn Pro Phe Ser Glu Asp Lys Thr Asp
1               5                   10


<210> SEQ ID NO 10
<211> LENGTH: 10
<212> TYPE: PRT
<213> ORGANISM: Homo sapiens

<400> SEQUENCE: 10
```

-continued

```
Ile Asp Gln Asp Pro Ser Gln Asn Pro Phe
1               5                   10


<210> SEQ ID NO 11
<211> LENGTH: 16
<212> TYPE: PRT
<213> ORGANISM: Homo sapiens

<400> SEQUENCE: 11

Ile Asp Gln Asp Pro Ser Gln Asn Pro Phe Ser Glu Asp Lys Thr Asp
1               5                   10                  15


<210> SEQ ID NO 12
<211> LENGTH: 10
<212> TYPE: PRT
<213> ORGANISM: Homo sapiens

<400> SEQUENCE: 12

Glu Ile Ala Gly Leu Gln Ile Gly Asp Lys
1               5                   10


<210> SEQ ID NO 13
<211> LENGTH: 10
<212> TYPE: PRT
<213> ORGANISM: Homo sapiens

<400> SEQUENCE: 13

Ile Gly Asp Lys Ile Met Gln Val Asn Gly
1               5                   10


<210> SEQ ID NO 14
<211> LENGTH: 16
<212> TYPE: PRT
<213> ORGANISM: Homo sapiens

<400> SEQUENCE: 14

Glu Ile Ala Gly Leu Gln Ile Gly Asp Lys Ile Met Gln Val Asn Gly
1               5                   10                  15


<210> SEQ ID NO 15
<211> LENGTH: 8
<212> TYPE: PRT
<213> ORGANISM: Mus musculus

<400> SEQUENCE: 15

Ser Phe Thr Gly Tyr Phe Met Asn
1               5


<210> SEQ ID NO 16
<211> LENGTH: 15
<212> TYPE: PRT
<213> ORGANISM: Mus musculus

<400> SEQUENCE: 16

Ile Gly Arg Ile Asp Pro Tyr Asn Gly Asn Ile Phe Tyr Asn Gln
1               5                   10                  15


<210> SEQ ID NO 17
<211> LENGTH: 12
<212> TYPE: PRT
<213> ORGANISM: Mus musculus

<400> SEQUENCE: 17

Ala Val Tyr Tyr Cys Gly Arg Ser Tyr Gly Asn Tyr
1               5                   10
```

<210> SEQ ID NO 18
<211> LENGTH: 10
<212> TYPE: PRT
<213> ORGANISM: Mus musculus

<400> SEQUENCE: 18

Gly Glu Thr Ile Thr Ile Asn Cys Arg Ala
1 5 10

<210> SEQ ID NO 19
<211> LENGTH: 12
<212> TYPE: PRT
<213> ORGANISM: Mus musculus

<400> SEQUENCE: 19

Lys Pro Gly Lys Thr Asn Lys Leu Leu Ile Tyr Phe
1 5 10

<210> SEQ ID NO 20
<211> LENGTH: 15
<212> TYPE: PRT
<213> ORGANISM: Mus musculus

<400> SEQUENCE: 20

Glu Pro Glu Asp Phe Ala Met Tyr Phe Cys Gln Gln His Asn Glu
1 5 10 15

<210> SEQ ID NO 21
<211> LENGTH: 10
<212> TYPE: PRT
<213> ORGANISM: Homo sapiens

<400> SEQUENCE: 21

Gln Pro Val Thr Ala Val Val Gln Arg Val
1 5 10

<210> SEQ ID NO 22
<211> LENGTH: 251
<212> TYPE: PRT
<213> ORGANISM: Mus musculus

<400> SEQUENCE: 22

Phe Phe Gly Asp Phe Gln Arg Glu Lys Ile Ile Ile Arg Asn Ser Phe
1 5 10 15

Ser Cys Ser Phe Leu Cys Gly Pro Ala Gly His Gly Pro Gly Glu Thr
20 25 30

Ala Ala Val Trp Gly Gln Gly Thr Thr Val Thr Val Ser Ser Gly Gly
35 40 45

Gly Gly Ser Gly Gly Gly Gly Ser Gly Gly Gly Gly Ser Asp Ile Glu
50 55 60

Leu Thr Gln Ser Pro Ser Thr Met Thr Ala Ser Pro Gly Glu Lys Val
65 70 75 80

Thr Ile Thr Cys Arg Ala Ser Ser Ser Val Ser Tyr Met His Trp Tyr
85 90 95

Gln Gln Lys Pro Gly Ala Ser Pro Lys Pro Trp Ile Tyr Asp Thr Ser
100 105 110

Lys Leu Ala Ser Gly Val Pro Asp Arg Phe Ser Gly Ser Gly Ser Gly
115 120 125

Thr Ser Tyr Ser Leu Thr Ile Asn Asn Met Glu Ala Glu Asp Ala Ala
130 135 140

```
Thr Tyr Tyr Cys Gln Gln Trp Asn Tyr Pro Ser Thr Phe Gly Ala Gly
145                 150                 155                 160

Thr Lys Leu Glu Ile Lys Pro Ala Ala Ala Gly Ala Pro Gly Val Pro
                165                 170                 175

Tyr Pro Asp Pro Leu Glu Pro Arg Ala Ala Thr Val Glu Ser Cys Leu
            180                 185                 190

Ala Lys Pro His Thr Glu Asn Ser Phe Thr Asn Val Trp Lys Asp Asp
        195                 200                 205

Lys Thr Leu Asp Arg Tyr Ala Asn Tyr Glu Gly Cys Leu Trp Asn Ala
    210                 215                 220

Thr Gly Val Val Val Cys Thr Gly Asp Glu Thr Gln Cys Tyr Gly Thr
225                 230                 235                 240

Trp Val Pro Ile Gly Leu Ala Ile Pro Glu Asn
                245                 250


<210> SEQ ID NO 23
<211> LENGTH: 239
<212> TYPE: PRT
<213> ORGANISM: Mus musculus

<400> SEQUENCE: 23

Phe Gln Arg Glu Lys Ile Ile Ile Arg Asn Ser Phe Ser Cys Ser Phe
1               5                   10                  15

Leu Cys Gly Pro Ala Gly His Gly Pro Gly Glu Thr Ala Ala Val Trp
            20                  25                  30

Gly Gln Gly Thr Thr Val Thr Val Ser Ser Gly Gly Gly Gly Ser Gly
        35                  40                  45

Gly Gly Gly Ser Gly Gly Gly Gly Ser Asp Ile Glu Leu Thr Gln Ser
    50                  55                  60

Pro Ser Thr Met Thr Ala Ser Pro Gly Glu Lys Val Thr Ile Thr Cys
65                  70                  75                  80

Arg Ala Ser Ser Ser Val Ser Tyr Met His Trp Tyr Gln Gln Lys Pro
                85                  90                  95

Gly Ala Ser Pro Lys Pro Trp Ile Tyr Asp Thr Ser Lys Leu Ala Ser
            100                 105                 110

Gly Val Pro Asp Arg Phe Ser Gly Ser Gly Ser Gly Thr Ser Tyr Ser
        115                 120                 125

Leu Thr Ile Asn Asn Met Glu Ala Glu Asp Ala Ala Thr Tyr Tyr Cys
    130                 135                 140

Gln Gln Trp Asn Tyr Pro Ser Thr Phe Gly Ala Gly Thr Lys Leu Glu
145                 150                 155                 160

Ile Lys Pro Ala Ala Ala Gly Ala Pro Val Pro Tyr Pro Asp Pro Leu
                165                 170                 175

Glu Pro Arg Ala Ala Thr Val Glu Ser Cys Leu Ala Lys Pro His Thr
            180                 185                 190

Glu Asn Ser Phe Thr Asn Val Trp Lys Asp Asp Lys Thr Leu Asp Arg
        195                 200                 205

Tyr Ala Asn Tyr Glu Gly Cys Leu Trp Asn Ala Thr Gly Val Val Val
    210                 215                 220

Cys Thr Gly Asp Glu Thr Gln Cys Tyr Gly Thr Trp Val Pro Ile
225                 230                 235


<210> SEQ ID NO 24
<211> LENGTH: 360
<212> TYPE: DNA
```

<213> ORGANISM: Mus musculus

<400> SEQUENCE: 24
gaagtgaagc ttgaggagtc tggaggaggc ttggtgcaac ctggaggatc catgaaactc 60
tcctgtgttg cctctggatt cactttcagt aactactgga tgaactgggt ccgccagtct 120
ccagagaagg ggcttgagtg ggttgctcaa attagattga aatctgataa ttatgcaaca 180
cattatgcgg agtctgtgaa agggaggttc accatctcaa gagatgattc caaaagtagt 240
gtctacctgc aaatgaacaa cttaagggct gaagacactg gaatttatta ctgcttactt 300
tactacggtc ctagcgggac tgcttactgg ggccaaggga ctctggtcac tgtctctgca 360

<210> SEQ ID NO 25
<211> LENGTH: 120
<212> TYPE: PRT
<213> ORGANISM: Mus musculus

<400> SEQUENCE: 25

Glu Val Lys Leu Glu Glu Ser Gly Gly Gly Leu Val Gln Pro Gly Gly
1 5 10 15

Ser Met Lys Leu Ser Cys Val Ala Ser Gly Phe Thr Phe Ser Asn Tyr
20 25 30

Trp Met Asn Trp Val Arg Gln Ser Pro Glu Lys Gly Leu Glu Trp Val
35 40 45

Ala Gln Ile Arg Leu Lys Ser Asp Asn Tyr Ala Thr His Tyr Ala Glu
50 55 60

Ser Val Lys Gly Arg Phe Thr Ile Ser Arg Asp Asp Ser Lys Ser Ser
65 70 75 80

Val Tyr Leu Gln Met Asn Asn Leu Arg Ala Glu Asp Thr Gly Ile Tyr
85 90 95

Tyr Cys Leu Leu Tyr Tyr Gly Pro Ser Gly Thr Ala Tyr Trp Gly Gln
100 105 110

Gly Thr Leu Val Thr Val Ser Ala
115 120

<210> SEQ ID NO 26
<211> LENGTH: 339
<212> TYPE: DNA
<213> ORGANISM: Mus musculus

<400> SEQUENCE: 26
gatgttgtga tgacccaaac tccactctcc ctgcctgtca gtcttggaga tcaagcctcc 60
atctcttgca gatctagtca gagccttgta cacagtaatg gaaacaccta tttacattgg 120
tacctgcaga agccaggcca gtctccaaag ctcctgatct acaaagtttc caaccgattt 180
tctggggtcc cagacaggtt cagtggcagt ggatcaggga cagatttcac actcaagatc 240
agcagagtgg aggctgagga tctgggagtt tatttctgct ctcaaagtac acatgttcct 300
cggacgttcg gtggaggcac caagctggaa atcaaacgg 339

<210> SEQ ID NO 27
<211> LENGTH: 113
<212> TYPE: PRT
<213> ORGANISM: Mus musculus

<400> SEQUENCE: 27

Asp Val Val Met Thr Gln Thr Pro Leu Ser Leu Pro Val Ser Leu Gly
1 5 10 15

```
Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Arg Thr Phe Gly Gly Gly Thr Lys Leu Glu Ile Lys
            100                 105                 110

Arg


<210> SEQ ID NO 28
<211> LENGTH: 6
<212> TYPE: PRT
<213> ORGANISM: Mus musculus

<400> SEQUENCE: 28

Ser Asn Tyr Trp Met Asn
1               5


<210> SEQ ID NO 29
<211> LENGTH: 13
<212> TYPE: PRT
<213> ORGANISM: Mus musculus

<400> SEQUENCE: 29

Gln Ile Arg Leu Lys Ser Asp Asn Tyr Ala Thr His Tyr
1               5                   10


<210> SEQ ID NO 30
<211> LENGTH: 9
<212> TYPE: PRT
<213> ORGANISM: Mus musculus

<400> SEQUENCE: 30

Gly Ile Tyr Tyr Cys Leu Leu Tyr Tyr
1               5


<210> SEQ ID NO 31
<211> LENGTH: 9
<212> TYPE: PRT
<213> ORGANISM: Mus musculus

<400> SEQUENCE: 31

Ser Gln Ser Leu Val His Ser Asn Gly
1               5


<210> SEQ ID NO 32
<211> LENGTH: 11
<212> TYPE: PRT
<213> ORGANISM: Mus musculus

<400> SEQUENCE: 32

Lys Leu Leu Ile Tyr Lys Val Ser Asn Arg Phe
1               5                   10


<210> SEQ ID NO 33
<211> LENGTH: 9
<212> TYPE: PRT
```

-continued

```
<213> ORGANISM: Mus musculus

<400> SEQUENCE: 33

Gly Val Tyr Phe Cys Ser Gln Ser Thr
1               5
```